United States Patent
Baldwin et al.

(10) Patent No.: US 12,310,660 B2
(45) Date of Patent: May 27, 2025

(54) OCULAR HYDRATION SENSOR

(71) Applicant: Meta Platforms Technologies, LLC, Menlo Park, CA (US)

(72) Inventors: Leo Baldwin, Seattle, WA (US); Mantas Zurauskas, Redmond, WA (US)

(73) Assignee: Meta Platforms Technologies, LLC, Menlo Park, CA (US)

( * ) Notice: Subject to any disclaimer, the term of this patent is extended or adjusted under 35 U.S.C. 154(b) by 0 days.

(21) Appl. No.: 18/468,069

(22) Filed: Sep. 15, 2023

(65) Prior Publication Data

US 2025/0090014 A1    Mar. 20, 2025

(51) Int. Cl.
  *A61B 3/10* (2006.01)
  *G02B 27/01* (2006.01)
  *G06F 3/01* (2006.01)
  *G06T 19/00* (2011.01)

(52) U.S. Cl.
  CPC .......... *A61B 3/101* (2013.01); *G02B 27/0172* (2013.01); *G06F 3/013* (2013.01); *G06T 19/006* (2013.01)

(58) Field of Classification Search
  CPC ....... A61B 3/101; A61B 3/113; A61B 5/6803; A61B 5/1455; A61B 5/0059; G02B 27/0172; G02B 27/0093; G02B 27/017; G02B 2027/0178; G06F 3/013; G02C 7/027; G02C 7/12
  See application file for complete search history.

(56) References Cited

U.S. PATENT DOCUMENTS

| | | | |
|---|---|---|---|
| 2020/0359886 A1* | 11/2020 | Azar | G02B 27/0172 |
| 2021/0093193 A1* | 4/2021 | Birkner | G06T 7/0012 |
| 2021/0217286 A1* | 7/2021 | Peyrard | G08B 21/0492 |
| 2022/0125299 A1* | 4/2022 | Abou Shousha | A61B 3/0025 |
| 2022/0155860 A1* | 5/2022 | Tzvieli | A61B 5/1455 |
| 2022/0217325 A1* | 7/2022 | Lee | G06V 40/19 |
| 2023/0092611 A1* | 3/2023 | Rafferty | B60H 1/00871 454/75 |
| 2023/0111835 A1* | 4/2023 | Balsam | A61B 3/10 345/589 |
| 2023/0410405 A1* | 12/2023 | Meina | G02B 27/0172 |

* cited by examiner

*Primary Examiner* — Xuemei Zheng
(74) *Attorney, Agent, or Firm* — Greenberg Traurig, LLP

(57) ABSTRACT

Apparatuses, methods, and systems for an ocular hydration sensor/reflectometer system in a near-eye display device are described. In one aspect, a near-eye display device may include a projector to project light onto a user's eye, a photodetector to receive reflections from the tear film of the user's eye (e.g., the tear glints), and a controller to make ocular hydration measurements from the received reflections. The ocular hydration measurements may be used to (1) re-calibrate an eye tracking system of the near-eye display device (by changing parameters such as, e.g., light intensity and/or exposure time); (2) prompt the user to take remedial action; and/or (3) keep track of the user's eye health over time. The projector, photodetector, and/or controller may be integrated into, separate from, or partially integrated/partially separate from the eye tracking system. Collective die-on-wafer processing, embedded motheye lens structures, and adaptive thermal management using thermoelectric coolers are also described.

20 Claims, 36 Drawing Sheets

Polarized Source and Polarization Sensitive Detector

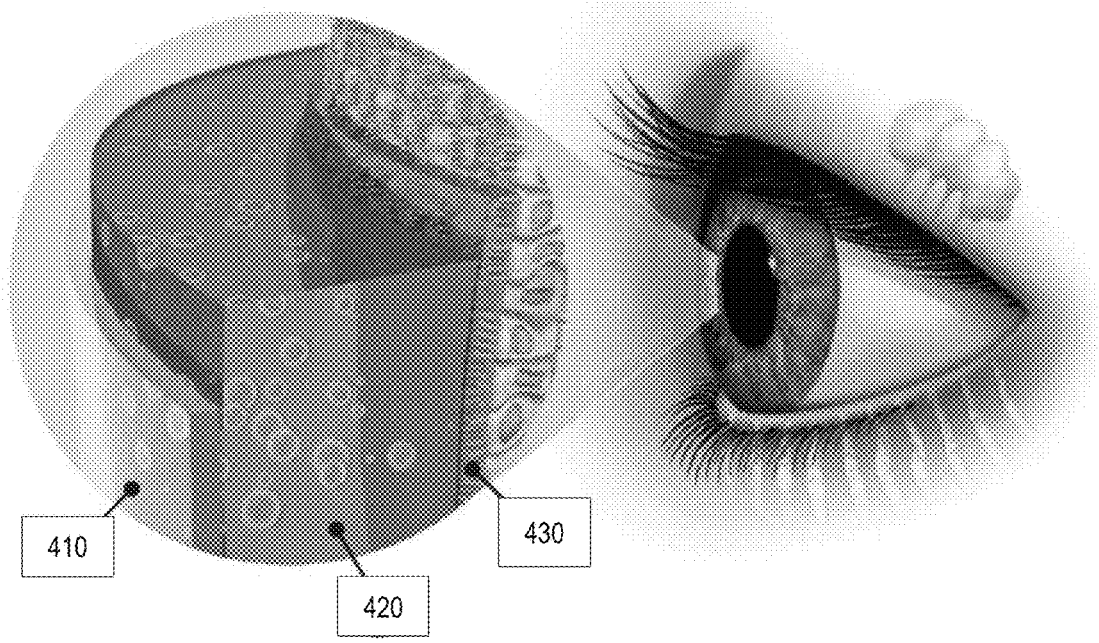

410 – Lipid Layer

Located on the outermost part of the tear film, the lipid (oil) layer stabilizes the tear film. When you have Meibomian Gland Dysfunction (the most common type of dry eye) your tear film has less oil, so your tears evaporate too quickly.

420 – Aqueous Layer

The Aqueous Layer is the largest portion of your tear film, responsible for supplying the moisture your eyes need to be comfortable. If you have Aqueous Layer Deficiency, your eyes don't produce enough of the watery component of tears, which makes it harder for your eyes to stay moist.

430 – Mucin Layer

This innermost layer consists of proteins called mucins that coat the eye and allow the Aqueous Layer to "stick" to the otherwise water-repellent cornea.

All three layers are necessary to create an ideal tear film for moist, healthy eyes. If any layer becomes depleted, the tear film cannot properly coat your eyes and dry spots can form. This causes your eyes to become symptomatic and uncomfortable.

FIG. 4

Reflectometer integrated with
Eye Tracking System

Polarized Source and
Polarization Sensitive Detector

Ocular Hydration Sensor Light Source
is the AR/VR Display

Ocular Hydration Sensor Light Source(s) integrated into AR/VR Display

Ocular Hydration Sensor Light Source
Is a Diffuse Light Source

Proposed Architecture

Proposed Alternative Architecture

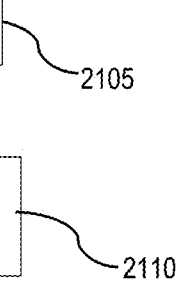
2100
Fabricating a micro-thermoelectric cooler (mTEC) in a substrate — 2105
Fabricating a micro-light emitting diode (mLED) into/above the substrate with the micro-thermoelectric cooler (mTEC) — 2110
FIG. 21
2200
Fabricating a micro-light emitting diode (mLED) — 2210
Fabricating a micro-thermoelectric cooler (mTEC) above the micro-light emitting diode (mLED) — 2215
FIG. 22

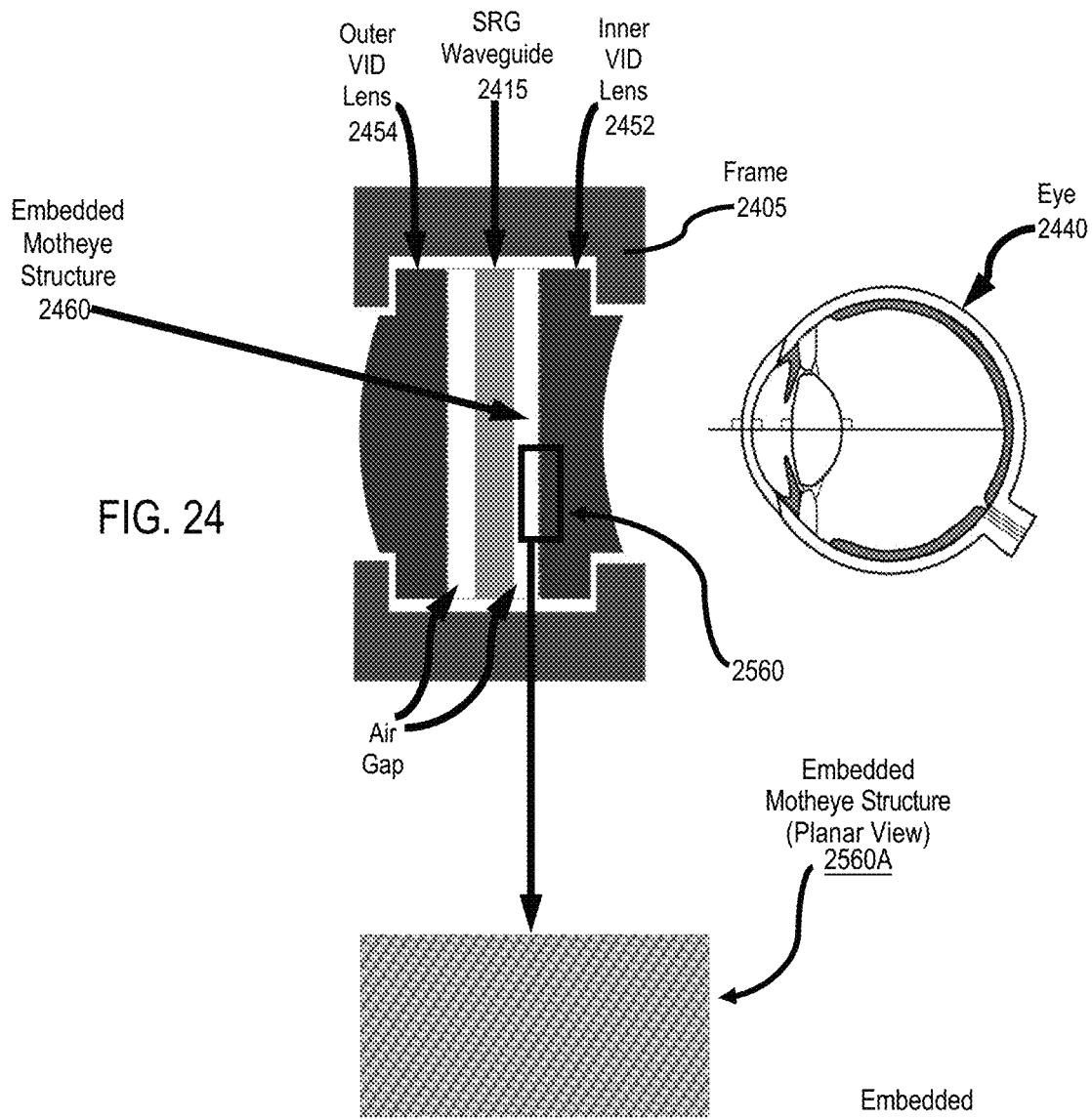
FIG. 24
FIG. 25
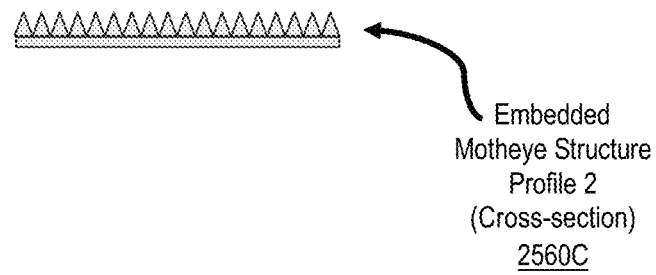

Manufacturing process description

Micro/nano replication

1. Master structure by diamond turning or lithography/etching to create motheye structure on metal mold

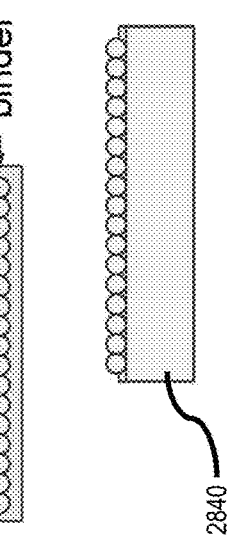

2. Replicate the motheye structure from metal mold to plastic VID lenses using cost-effective approaches like injection molding, or compression molding, UV casting or hot imprinting

FIG. 26

Plasma etch for surface roughening

1. Plasma etch for surface roughening

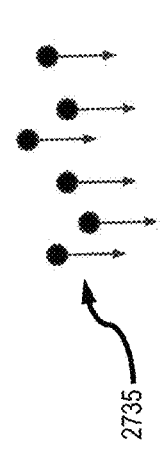

2. Optional transfer to other surfaces by replication

FIG. 27

Direct coating

FIG. 28

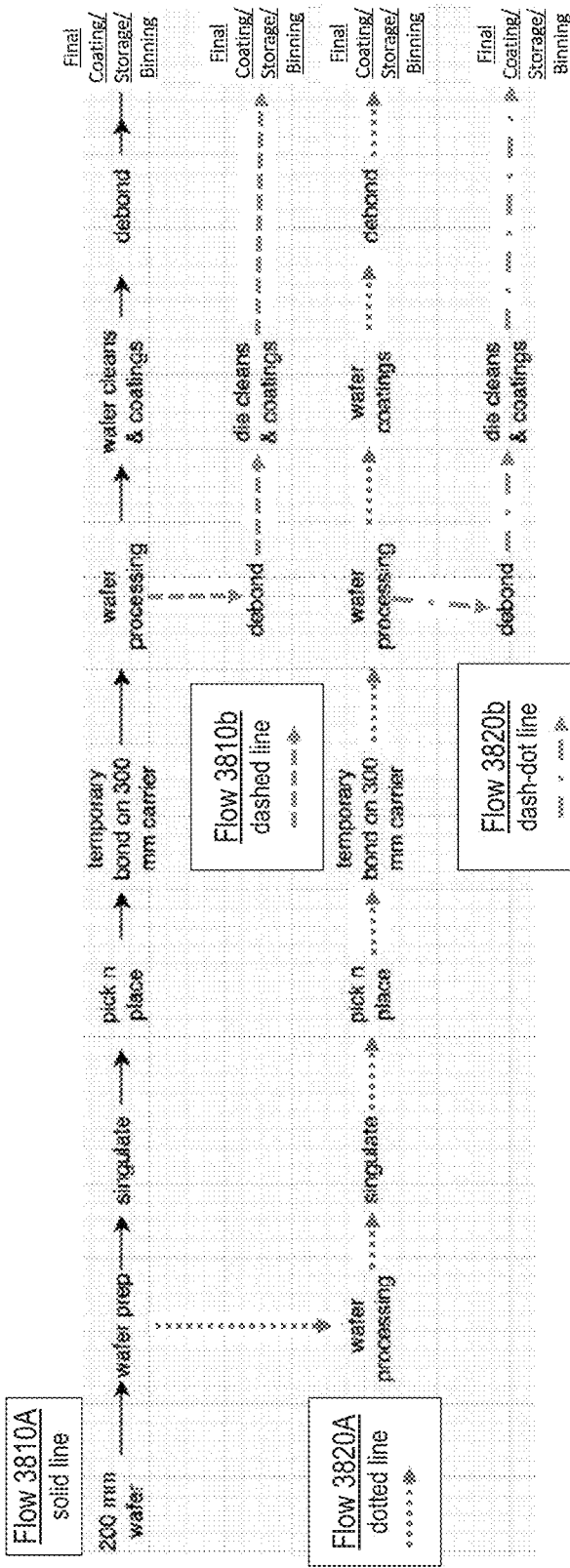
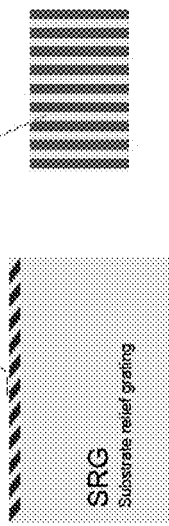
FIG. 38

OCULAR HYDRATION SENSOR

TECHNICAL FIELD

This provisional patent application relates generally to user comfort and the performance of a near-eye display device, and more specifically, to providing an ocular hydration sensor and system for a near-eye display device.

BACKGROUND

With recent advances in technology, the prevalence and proliferation of content creation and delivery has increased greatly in recent years. In particular, interactive content such as virtual reality (VR) content, augmented reality (AR) content, mixed reality (MR) content, and content within and associated with a real and/or virtual environment (e.g., a "metaverse") has become appealing to consumers.

To facilitate delivery of this and other related content, service providers have endeavored to provide various forms of wearable display systems. One such example may be a near-eye display device, such as, e.g., a wearable headset or head-mounted display (HMD) device, a wearable eyewear, or eyeglasses (e.g., "smartglasses"). In some examples, the head-mounted display (HMD) device may project or direct light to may display virtual objects or combine images of real objects with virtual objects, as in virtual reality (VR), augmented reality (AR), or mixed reality (MR) applications. For example, in an augmented reality (AR) system, a user may view both images of virtual objects (e.g., computer-generated images (CGIs)) and the surrounding environment. Head-mounted display (HMD) devices may also present interactive content, where a user's (wearer's) gaze may be used as input for the interactive content.

Wearable display devices, such as virtual reality (VR), augmented reality (AR), and/or mixed reality (MR) glasses, may require increasingly complex and intricate lens assembly structures for display, as well as increasingly complex and intricate electronic structures for generating and providing virtual reality (VR), augmented reality (AR), and/or mixed reality (MR) content, etc., thereby complicating, inter alia, the manufacturing process. Moreover, the need for both electronics and optics to have a relatively small size and negligible weight for portability and user comfort, as well as the ability to operate in a wide variety of environments, produces a host of challenges and competing concerns, in areas such as, for example, the hydration of the user's eyes (ocular hydration).

BRIEF DESCRIPTION OF DRAWINGS

Features of the present disclosure are illustrated by way of example and not limited in the following figures, in which like numerals indicate like elements. One skilled in the art will readily recognize from the following that alternative examples of the structures and methods illustrated in the figures can be employed without departing from the principles described herein.

FIG. 4 illustrates the outer layers of the surface of the eye relevant to the problems ameliorated by systems, apparatuses, and methods according to examples of the present disclosure.

FIGS. 11 to 22 illustrate aspects concerning Section II-Adaptive Thermal Management using Micro-Thermoelectric Coolers (MTECs) and Artificial Intelligence (AI), of the present disclosure.

FIGS. 23 to 30 illustrate aspects concerning Section III-Embedded Motheye Structure, of the present disclosure.

FIGS. 31 to 40 illustrate aspects concerning Section IV-Collective Die-on-Wafer Processing, of the present disclosure.

DETAILED DESCRIPTION

Figure 1:
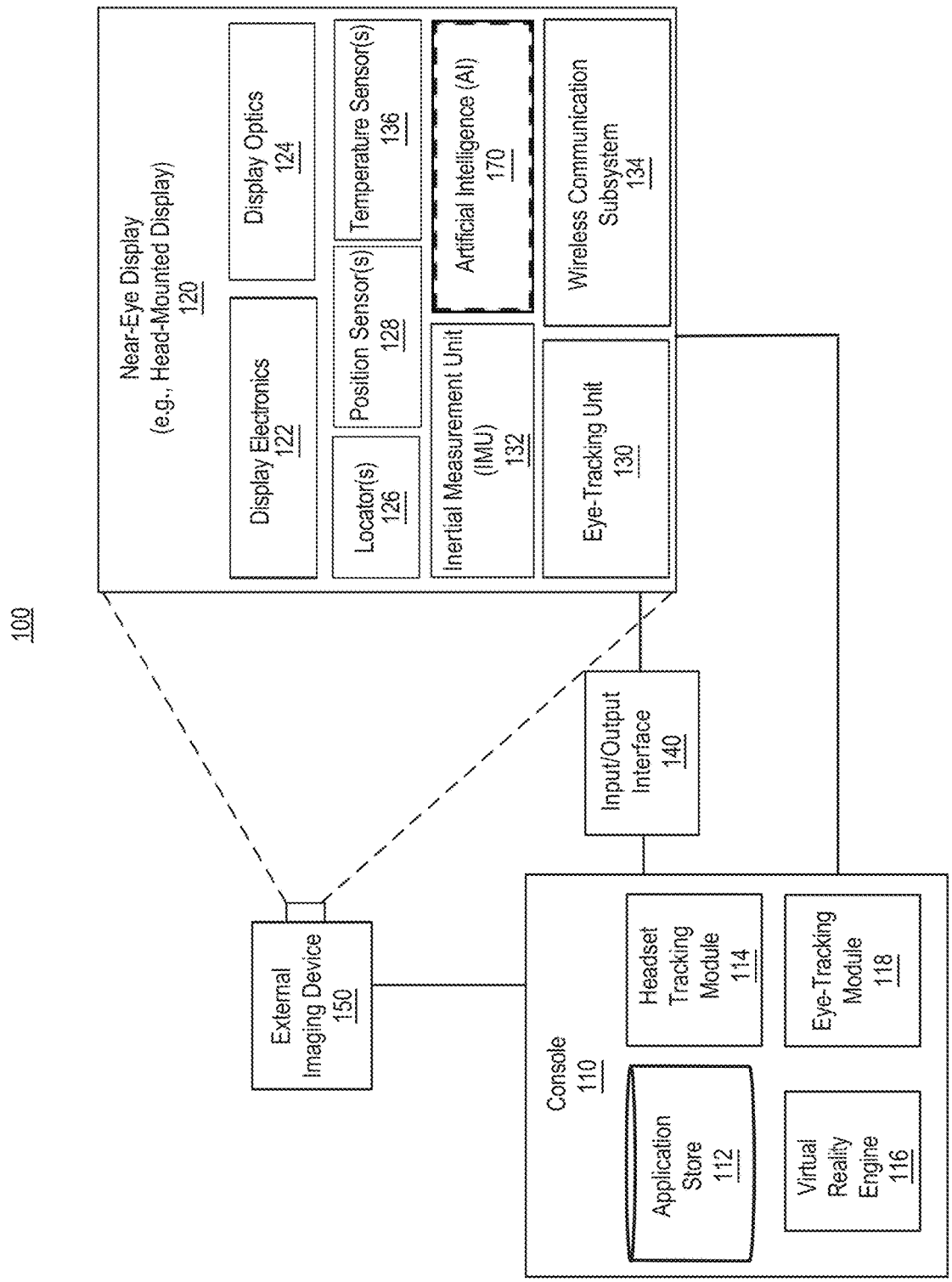
FIG. 1 illustrates a block diagram of an artificial reality system environment including a near-eye display device, according to an example.

For simplicity and illustrative purposes, the present application is described by referring mainly to examples thereof. In the following description, numerous specific details are set forth in order to provide a thorough understanding of the present application. It will be readily apparent, however, that the present application may be practiced without limitation to these specific details. In other instances, some methods and structures readily understood by one of ordinary skill in the art have not been described in detail so as not to unnecessarily obscure the present application. As used herein, the terms "a" and "an" are intended to denote at least one of a particular element, the term "includes" means includes but not limited to, the term "including" means including but not limited to, and the term "based on" means based at least in part on.

As used herein, a "near-eye display device" may refer to any display device (e.g., an optical device) that may be in close proximity to a user's eye. Accordingly, a near-eye display device may be a head-mounted display (HMD) device, such as a wearable eyewear, a wearable headset, and/or "smartglasses," which may be used for interacting with virtual reality (VR), augmented reality (AR), and/or mixed reality (MR) environments, or any environment of real and virtual elements, such as a "metaverse." As used herein, a "wearable device" may refer to any portable electronic device that may be worn on any body part of a user and used to present audio and/or video content, control other devices, monitor bodily functions, and perform similar actions. As used herein, a "user" may refer to a user or wearer of a "near-eye display device" and/or a "wearable display."

As mentioned above, user comfort and the user experience (UX) are a challenge and concern in terms of providing virtual reality (VR), augmented reality (AR), and/or mixed reality (MR) content, etc., in a near-eye display device. One concern/challenge is the hydration of the user's eyes (ocular hydration) which may fundamentally affect whether the eye tracking capabilities of the near-eye display device as well as whether the user has a positive or negative UX.

According to examples of the present disclosure, apparatuses, systems, and/or methods for an ocular hydration sensor/reflectometer system are presented. In some examples, an ocular hydration sensor/reflectometer system projects light onto an eye of a user of a near-eye display device, receives light reflected from a tear film of the eye, measures ocular hydration using the received reflected light, and re-calibrates eye tracking parameters of an eye tracking system of the near-eye display device based on the ocular hydration measurements. In some examples, a projector of a near-eye display device projects light onto an eye of a user, a photodetector receives reflections of the projected light from the tear film of the user's eye, a controller performs one or more reflectometric measurements of ocular hydration using the received reflections as input from the photodetector, and an eye tracking system of the near-eye display device is re-calibrated based on the one or more reflectometric measurements.

While some advantages and benefits of the present disclosure are discussed herein, there are additional benefits and advantages which would be apparent to one of ordinary skill in the art.

FIG. 1 illustrates a block diagram of an artificial reality system environment 100 including a near-eye display device, according to an example. As used herein, a "near-eye display device" may refer to a device (e.g., an optical device) that may be in close proximity to a user's eye. As used herein, "artificial reality" may refer to aspects of, among other things, a "metaverse" or an environment of real and virtual elements and may include use of technologies associated with virtual reality (VR), augmented reality (AR), and/or mixed reality (MR). As used herein a "user" may refer to a user or wearer of a "near-eye display device."

As shown in FIG. 1, the artificial reality system environment 100 may include a near-eye display device 120, an optional external imaging device 150, and an optional input/output interface 140, each of which may be coupled to an optional console 110. The optional console 110 may be optional in some instances where functions of the optional console 110 may be integrated into the near-eye display device 120. In some examples, the near-eye display device 120 may be implemented in any suitable form-factor, including a head-mounted display (HMD), a pair of glasses, or other similar wearable eyewear or device. In some examples, the near-eye display device 120 may include one or more rigid bodies, which may be rigidly or non-rigidly coupled to each other. In some examples, a rigid coupling between rigid bodies may cause the coupled rigid bodies to act as a single rigid entity, while in other examples, a non-rigid coupling between rigid bodies may allow the rigid bodies to move relative to each other. Specific examples of the near-eye display device 120 are described further below with respect to FIGS. 2A-2C and 3A-3B.

In some examples, the near-eye display device 120 may be a head-mounted display (HMD) that presents content to a user, including, for example, audio/visual content, such as, e.g., virtual reality (VR), augmented reality (AR), and/or mixed reality (MR) content. Additionally, in some examples, the functionality described herein may be used in a head-mounted display (HMD) or headset that may combine images of an environment external to the near-eye display device 120 and artificial reality content (e.g., computer-generated images). Therefore, in some examples, the near-eye display device 120 may augment images of a physical, real-world environment external to the near-eye display device 120 with generated and/or overlaid digital content (e.g., images, video, sound, etc.) to present an augmented reality to a user.

In some examples, the near-eye display device 120 may include any one or more of display electronics 122, display optics 124, one or more locators 126, one or more position sensors 128, an eye tracking unit 130, an inertial measurement unit (IMU) 132, a wireless communication subsystem 134, one or more temperature sensor(s) 136, and/or an (optional) artificial intelligence (AI) module 170. In some examples, the near-eye display device 120 may include additional components; in other examples, the near-eye display device 120 may omit any one or more of the one or more locators 126, the one or more position sensors 128, the eye tracking unit 130, the inertial measurement unit (IMU) 132, the wireless communication subsystem 134, the one or more temperature sensor(s) 136, and/or the artificial intelligence (AI) module 170.

In some examples, the display electronics 122 may display or facilitate the display of images to the user according to data received from control electronics such as, for example, the optional console 110, a virtual reality engine (such as, for example, the virtual reality engine 116 described below), etc. In some examples, the display electronics 122 may include one or more display panels, and may include and/or be operationally connected to the display optics 124. In some examples, the display electronics may include one or more of a liquid crystal display (LCD) and/or a light-emitting diode (LED). In some examples, the display electronics 122 may include any number of pixels to emit light of a predominant color such as red, green, blue, white, or yellow. In some examples, the display electronics 122 may display a three-dimensional (3D) image, e.g., using stereoscopic effects produced by two-dimensional panels, to create a subjective perception of image depth.

In some examples, the display electronics 122 may include one or more projectors (not shown), which may form an image in angular domain for direct observation by a viewer's eye through a pupil. In some examples, the same projector(s) or a different projector(s) may be used to project a fringe pattern on the eye, which may be captured by a camera and analyzed (e.g., by the eye tracking unit 130) to determine a position of the eye (the pupil), a gaze, etc. In some examples, a location of any of the one or more projectors may be adjusted to enable any number of design modifications. For example, in some instances, a projector may be located in front of a viewer's eye (e.g., "front-mounted" placement). In a front-mounted placement, in some examples, a projector of a display system may be located away from a user's eyes (e.g., "world-side"). In some examples, a head-mounted display (HMD) device may utilize a front-mounted placement to propagate light towards a user's eye(s) to project an image.

In some examples, the one or more projectors in the display electronics 122 may employ a controllable light source (e.g., a laser) and a micro-electromechanical system (MEMS) beam scanner to create a light field from, for example, a collimated light beam. In some examples, the light source of the one or more projectors may include one or more of a liquid crystal display (LCD), a light emitting diode (LED) or micro-light emitting diode (mLED), an organic light emitting diode (OLED), an inorganic light emitting diode (ILED), an active-matrix organic light emitting diode (AMOLED), a transparent organic light emitting diode (TLED), any other suitable light source, and/or any combination thereof. In some examples, the one or more projectors may comprise a single electronic display or multiple electronic displays (e.g., one for each eye of the user).

In some examples, the display optics 124 may project, direct, and/or otherwise display image content optically and/or magnify image light received from the display electronics 122, correct optical errors associated with the image light, and/or present the (corrected) image light to a user of the near-eye display device 120. In some examples, the display optics 124 may also be designed to correct one or more types of optical errors, such as two-dimensional optical errors, three-dimensional optical errors, or any combination thereof. Examples of two-dimensional errors may include barrel distortion, pincushion distortion, longitudinal chromatic aberration, and/or transverse chromatic aberration. Examples of three-dimensional errors may include spherical aberration, chromatic aberration field curvature, and astigmatism.

In some examples, the display optics 124 may include an optical element or any number of combinations of various optical elements as well as mechanical couplings to, for example, maintain relative spacing and orientation of the optical elements in the combination. In some examples, one or more optical elements in the display optics 124 may include an aperture, a Fresnel lens, a refractive lens, a reflective mirror, a diffractive element, a waveguide, a filter, or any other optical element suitable for affecting and/or otherwise manipulating light emitted from the display electronics 122. In some examples, one or more optical elements in the display optics 124 may have an optical coating, such as an anti-reflective coating, a reflective coating, a filtering coating, and/or a combination of different optical coatings.

In some examples, the display optics 124 may be used to combine the view of an environment external to the near-eye display device 120 and artificial reality content (e.g., computer-generated images) generated by, e.g., the virtual reality engine 116 in the console 110, and projected by, e.g., the display electronics 122. In such examples, the display optics 124 may augment images of a physical, real-world environment external to the near-eye display device 120 with generated and/or overlaid digital content (e.g., images, video, sound, etc.) projected by the display electronics 122 to present an augmented reality (AR) to a user.

In some examples, the one or more locators 126 may be objects located in specific positions relative to one another and relative to a reference point on the near-eye display device 120. In some examples, the optional console 110 may identify the one or more locators 126 in images captured by the optional external imaging device 150 to determine the artificial reality headset's position, orientation, or both. The one or more locators 126 may each be a light-emitting diode (LED), a corner cube reflector, a reflective marker, a type of light source that contrasts with an environment in which the near-eye display device 120 operates, or any combination thereof.

In some examples, the external imaging device 150 may include one or more cameras, one or more video cameras, any other device capable of capturing images including the one or more locators 126, or any combination thereof. The optional external imaging device 150 may detect light emitted or reflected from the one or more locators 126 in a field of view of the optional external imaging device 150.

In some examples, the one or more position sensors 128 may sense motion of the near-eye display device 120 and, in response, generate one or more measurement signals and/or data. Examples of the one or more position sensors 128 may include any number of accelerometers, gyroscopes, magnetometers, and/or other motion-detecting or error-correcting sensors, or any combination thereof.

In some examples, the inertial measurement unit (IMU) 132 may be an electronic device that generates fast calibration data based on measurement signals received from the one or more position sensors 128. The one or more position sensors 128 may be located external to the inertial measurement unit (IMU) 132, internal to the inertial measurement unit (IMU) 132, or any combination thereof. Based on the one or more measurement signals from the one or more position sensors 128, the inertial measurement unit (IMU) 132 may generate fast calibration data indicating an estimated position of the near-eye display device 120. Estimated positions may be of a reference point on the near-eye display device 120, and estimated positions may be, for example, relative to an initial position of the near-eye display device 120, relative to other objects in an external environment, relative to virtual objects in an artificial environment or augmented/mixed reality, etc., as would be understood by one of ordinary skill in the art. For example, the inertial measurement unit (IMU) 132 may integrate measurement signals received from accelerometers over time to estimate a velocity vector and integrate the velocity vector over time to determine an estimated position of the near-eye display device 120. Alternatively, the inertial measurement unit (IMU) 132 may provide the sampled measurement signals to the optional console 110, which may determine the fast calibration data.

The eye tracking unit 130 may include one or more eye tracking systems. As used herein, "eye tracking" may refer to determining an eye's position or relative position, including orientation, location, and/or gaze of a user's eye. In some examples, an eye tracking system may include an imaging system that captures one or more images of an eye and may optionally include a light emitter, which may generate light (e.g., a fringe pattern) that is directed to an eye such that light reflected by the eye may be captured by the imaging system (e.g., a camera). In other examples, the eye tracking unit 130 may capture reflected radio waves emitted by a miniature radar unit. These data associated with the eye may be used to determine or predict eye position, orientation, movement, location, and/or gaze.

In some examples, the wireless communication subsystem 134 may include an ultra-wide band (UWB) transceiver. Ultra-wide band (UWB) wireless communication technology is used for short-range, fast, and secure data transmission environments. Ultra-wide band (UWB) wireless communication technology provides high transmission speed, low power consumption, and large bandwidth, in addition to the ability to co-exist with other wireless transmission technologies. The ultra-wide band (UWB) transceiver may be used to detect another user (head-mounted display (HMD) device) within range of communication and within an angle-of-arrival (AoA), then establish line-of-sight (LoS) communication between the two users. The communication may be in audio mode only or in audio/video mode. In other examples, the ultra-wide band (UWB) transceiver may be used to detect the other user, but a different communication technology (transceiver) such as WiFi or Bluetooth Low Energy (BLE) may be used to facilitate the line-of-sight (LoS) communication. In some cases, multiple wireless communication transceivers may be available and one with lowest power consumption, highest communication quality (e.g., based on interfering signals), or user choice may be used. For example, the communication technology may be selected based on a lowest power consumption for a given range.

In some examples, the one or more temperature sensor(s) 136 may be located in specific positions on/in the near-eye display device 120 suitable for determining the temperature of the user, the external environment, and/or components within the near-eye display device 120. In some examples, the one or more temperature sensor(s) 136 may be located in specific positions suitable for determining the temperature of any one or more of the display electronics 122 of the near-eye display device 120, such as, e.g., the one or more projectors which may form images for direct observation by the user.

In some examples, the artificial intelligence (AI) module 170 may be employed as an ocular hydration sensor/reflectometer system controller according to the present disclosure. In some examples, the artificial intelligence (AI) module 170 may receive input, store and process data, and/or control the eye tracking unit 130 in accordance with received input and/or stored/processed data in order to maintain optimal operating conditions of one or more components in the near-eye display device 120.

In some examples, the near-eye display device 120 may include any number of processors and non-transitory computer-readable storage media storing instructions executable by the processor(s). The processor(s) may include multiple processing units executing instructions in parallel. The non-transitory computer-readable storage medium/media may be any memory, such as a hard disk drive, a removable memory, or a solid-state drive (e.g., flash memory or dynamic random access memory (DRAM)). In some examples, one or more processors in the near-eye display device 120 may perform one or more functions; in some examples, one or more non-transitory computer-readable storage media in the near-eye display device 120 may store instructions that, when executed by the one or more processors, cause the one or more processors to perform any of the functions described herein and/or to control any of the components described herein. In some examples, functions such as those described below in reference to the optional console 110 (e.g., eye-tracking, headset tracking, and the generation of virtual reality images) may be performed by one or more processors integrated with or wired/wirelessly connected to the near-eye display device 120.

In some examples, the input/output interface 140 may be a device that allows a user to send action requests to the optional console 110 and/or the near-eye display device 120. As used herein, an "action request" may be a request to perform a particular action. For example, an action request may be to start or to end an application or to perform a particular action within the application. The input/output interface 140 may include one or more input devices. Example input devices may include a keyboard, a mouse, a game controller, a glove, a button, a touch screen, or any other suitable device for receiving action requests and communicating the received action requests to the optional console 110. In some examples, an action request received by the input/output interface 140 may be communicated to the optional console 110 and/or the near-eye display device 120, either or both of which may perform an action corresponding to the requested action.

In some examples, the optional console 110 may provide content to the near-eye display device 120 for presentation to the user in accordance with information received from one or more of the near-eye display device 120, the input/output interface 140, and/or the external imaging device 150. For example, as shown in the example of FIG. 1, the optional console 110 may include an application store 112, a headset tracking module 114, a virtual reality engine 116, and an eye tracking module 118. In some examples, the optional console 110 may include different or additional modules than those described herein, and the functions described further below may be distributed among the components of the optional console 110 in a different manner than is described here (or may be distributed, in part or whole, in one or more components in the near-eye display device 120).

In some examples, the optional console 110 may include a processor and a non-transitory computer-readable storage medium storing instructions executable by the processor. The processor may include multiple processing units executing instructions in parallel. The non-transitory computer-readable storage medium may be any memory, such as a hard disk drive, a removable memory, or a solid-state drive (e.g., flash memory or dynamic random access memory (DRAM)). In some examples, the modules of the optional console 110 described in conjunction with FIG. 1 may be encoded as instructions in the non-transitory computer-readable storage medium that, when executed by the processor, cause the processor to perform the functions further described below. It should be appreciated that the optional console 110 may or may not be needed, or the optional console 110 may be integrated, in whole or in part, with the input/output interface 140 and/or the near-eye display device 120, or the optional console 110 may be separate from the input/output interface 140 and/or the near-eye display device 120.

In some examples, the application store 112 may store one or more applications for execution by the optional console 110. An application may include a group of instructions that, when executed by a processor, generates content for presentation to the user. Examples of the applications may include gaming applications, conferencing applications, video playback application, or other suitable applications.

In some examples, the virtual reality engine 116 may execute applications within the artificial reality system environment 100 and receive position information of the near-eye display device 120, acceleration information of the near-eye display device 120, velocity information of the near-eye display device 120, predicted future positions of the near-eye display device 120, or any combination thereof from the headset tracking module 114. In some examples, the virtual reality engine 116 may also receive estimated eye position and orientation information from the eye tracking module 118. Based on the received information, the virtual reality engine 116 may determine content including, e.g., virtual reality images, to provide to the near-eye display device 120 for presentation to the user.

In some examples, the eye tracking module 118, which may be implemented as a processor, may receive eye tracking data from the eye tracking unit 130 and determine the position of the user's eye based on the eye tracking data. In some examples, the position of the eye may include an eye's orientation, location, or both relative to the near-eye display device 120 or any element thereof. So, in these examples, because the eye's axes of rotation change as a function of the eye's location in its socket, determining the eye's location in its socket may allow the eye tracking module 118 to more accurately determine the eye's orientation.

Figure 2A:
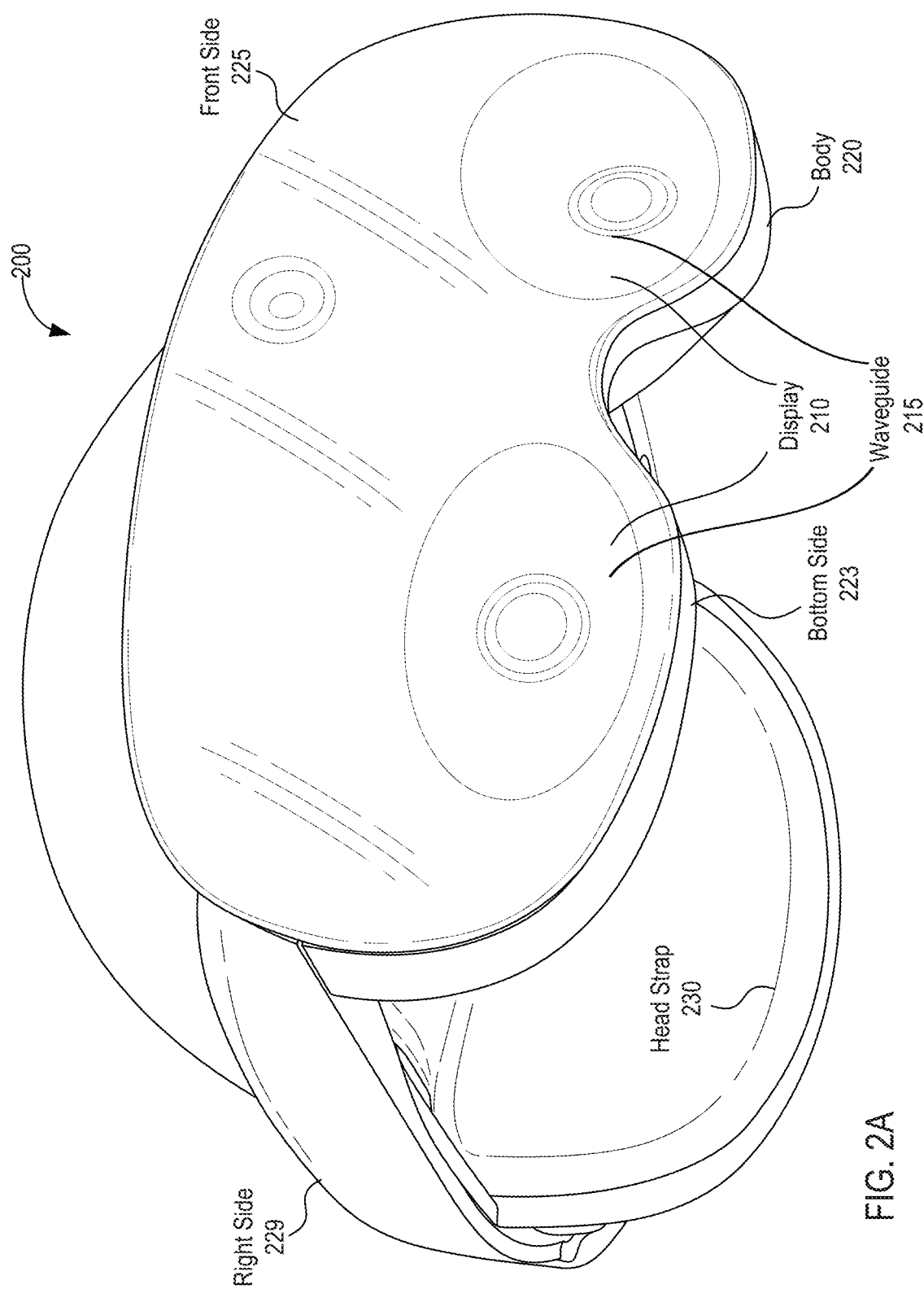
FIGS. 2A through 2C illustrate various views of a near-eye display device in the form of a head-mounted display (HMD) device, according to an example.
Figure 2B:
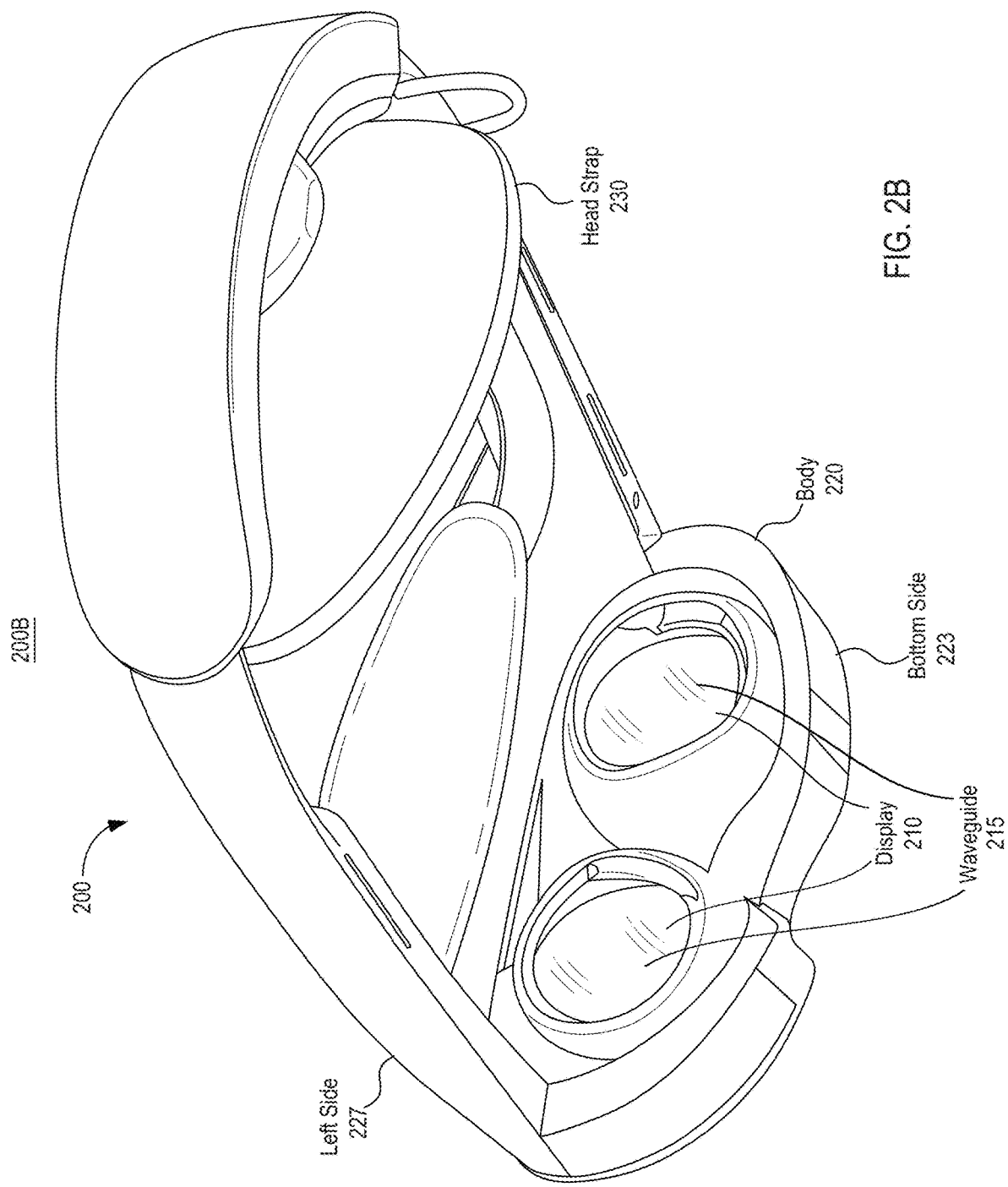
Figure 2C:
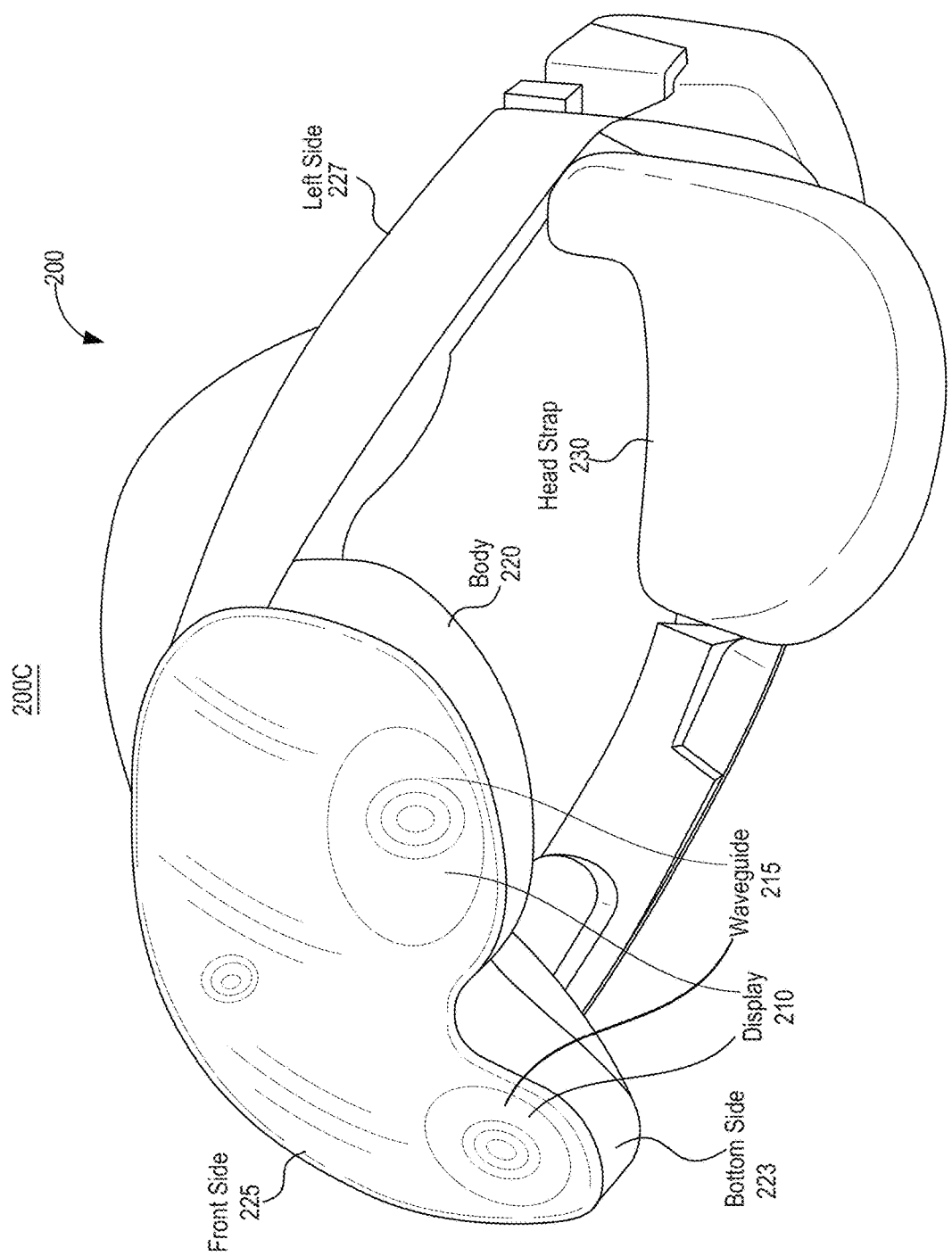

FIGS. 2A through 2C illustrate various views of a near-eye display device in the form of a head-mounted display (HMD) device 200, according to an example. In some examples, the head-mounted display (HMD) device 200 may be a specific implementation of the near-eye display 120 of FIG. 1, and may be configured to operate as a virtual reality (VR) system, an augmented reality (AR) system, a mixed reality (MR) system, and/or as part of any such system that uses displays or wearables, or any combination thereof. In some examples, the head-mounted display (HMD) device 200 may include a display 210, a body 220 and a head strap 230. In some examples, the head-mounted display (HMD) device 200 may include additional, fewer, and/or different components than shown and/or described in reference to FIGS. 2A-2C.

FIG. 2A is a frontal prospective view 200A showing a front side 225, a bottom side 223, and a right side 229 of the body 220, as well as the display 210 and the head strap 230 of the head-mounted display (HMD) device 200. FIG. 2B is a bottom rear prospective view 200B showing the bottom side 223, the front side 225, and a left side 227 of the body 220, as well as the display 210 and the head strap 230 of the head-mounted display (HMD) device 200. FIG. 2C is a front rear prospective view 200C showing the bottom side 223, the front side 225, and the left side 227 of the body 220, as well as the display 210 and the head strap 230 of the head-mounted display (HMD) device 200.

In some examples, the head strap 230 may have an adjustable or extendible length. In particular, in some examples, there may be a sufficient space between the body 220 and the head strap 230 of the head-mounted display (HMD) device 200 for allowing a user to mount the head-mounted display (HMD) device 200 onto the user's head. For example, the length of the head strap 230 may be adjustable to accommodate a range of user head sizes.

In some examples, the display 210 may include one or more display assemblies and present, to a user (wearer), media or other digital content including virtual and/or augmented views of a physical, real-world environment with computer-generated elements. Examples of the media or digital content presented by the head-mounted display (HMD) device 200 may include images (e.g., two-dimensional (2D) or three-dimensional (3D) images), videos (e.g., 2D or 3D videos), audio, or any combination thereof. In other examples, the display 210 may include one or more projectors, which may form an image for observation by the user by projecting the image directly on the user's eye.

In some examples, the head-mounted display (HMD) device 200 and the display 210 may include any number of display electronics and display optics similar to the display electronics 122 and display optics 124 described in reference to FIG. 1. In some examples, the display electronics may display or facilitate the display of images to the user according to data received from, for example, control electronics such as a virtual reality engine (such as, for example, the virtual reality engine 116 described in reference to FIG. 1). In some examples, the display electronics may display a three-dimensional (3D) image, e.g., using stereoscopic effects produced by two-dimensional panels, to create a subjective perception of image depth. In some examples, the display optics in the head-mounted display (HMD) device 200 may include a single optical element or any number of combinations of various optical elements, such as waveguides, gratings, optical lenses, optical couplers, mirrors, etc., as well as mechanical couplings to maintain relative spacing and orientation of the optical elements in the combination, such as are described above in reference to the display optics 124 in FIG. 1.

As shown in FIGS. 2A-2C, the display 210 may include waveguide 215. In some examples, the waveguide 215 may be coupled to display electronics (similar to the display electronics 122 in FIG. 1) which may project an augmented reality (AR) display and/or a mixed reality (MR) image through the waveguide 315 to be projected onto the user's eyes. In some examples, light from a surrounding environment of the near-eye display device 200 may traverse a "see-through" region of the waveguide 215 in the display 210 to reach the user's eyes, while images are also projected by the coupled display electronics for the user to see as part of an augmented reality (AR) display and/or a mixed reality (MR) display. In such examples, the light of images projected by the display electronics may be coupled into a transparent substrate of the waveguide 215, propagate within the waveguide 215, be coupled with light from the user's actual environment, and be directed out of the waveguide 215 at one or more locations towards the user's eyes. Waveguides such as the waveguide 215 are described in greater detail below in reference to FIGS. 3A and 3B.

In some examples, the display electronics and/or the display 210 may include one or more projectors, which may project an image for direct observation by the user's eye. In some examples, the one or more projectors included in the display electronics and/or the display 210 may include one or more of a liquid crystal display (LCD) and/or a light-emitting diode (LED); more specifically, the one or more projectors may include, e.g., one or more of a liquid crystal display (LCD), a light emitting diode (LED) or micro-light emitting diode (mLED), an organic light emitting diode (OLED), an inorganic light emitting diode (ILED), an active-matrix organic light emitting diode (AMOLED), a transparent organic light emitting diode (TLED), any other suitable light source, and/or any combination thereof. It should be appreciated that in some examples, the one or more projectors may be placed near and/or closer to a user's eye (e.g., "eye-side"). It should be appreciated that, in some instances, utilizing a back-mounted projector placement may help to reduce size or bulkiness of any required housing required for a display system, which may also result in a significant improvement in user experience for a user.

In some examples, the head-mounted display (HMD) device 200 may also include an eye-tracking system, one or more locators, one or more position sensors, and an inertial measurement unit (IMU) similar to the eye-tracking unit 130, the one or more locators 126, the one or more position sensors 128, and the inertial measurement unit (IMU) 132 described in reference to FIG. 1. In some examples, the head-mounted display (HMD) device 100 may include various other sensors, such as depth sensors, motion sensors, image sensors, light sensors, and/or the like. Some of these sensors may sense any number of projected structured or unstructured light patterns for any number of purposes, including, e.g., sensing, eye-tracking, and/or the creation of virtual reality (VR) content.

In some examples, the head-mounted display (HMD) device 200 may include a virtual reality engine (not shown), similar to the virtual reality engine 116 described in reference to FIG. 1, that may execute applications within the head-mounted display (HMD) device 200 and receive depth information, position information, acceleration information, velocity information, predicted future positions, or any combination thereof of the head-mounted display (HMD) device 200 from the various sensors. In some examples, the information received by the virtual reality engine may be used for producing a signal (e.g., display instructions) to the one or more display assemblies. In some examples, the head-mounted display (HMD) device 200 may include locators (not shown), similar to the one or more locators 126 described in reference to FIG. 1, which may be located in fixed positions on the body 220 of the head-mounted display (HMD) device 200 relative to one another and relative to a reference point. Each of the locators may emit light that is detectable by an external imaging device. This may be useful for the purposes of head tracking or other movement/ orientation. It should be appreciated that other elements or components may also be used in addition or in lieu of such locators.

As stated above, the head-mounted display (HMD) device 200 may include additional, fewer, and/or different components than shown and/or described in reference to FIGS. 2A-2C. In some examples, the head-mounted display (HMD) device 200 may include an input/output interface (similar to the input/output interface 140 in FIG. 1), a console (similar to the console 110 described in reference to FIG. 1), and/or a camera to capture images or videos of the user's environment to present the user with, e.g., augmented reality (AR)/virtual reality (VR) content.

Figure 3A:
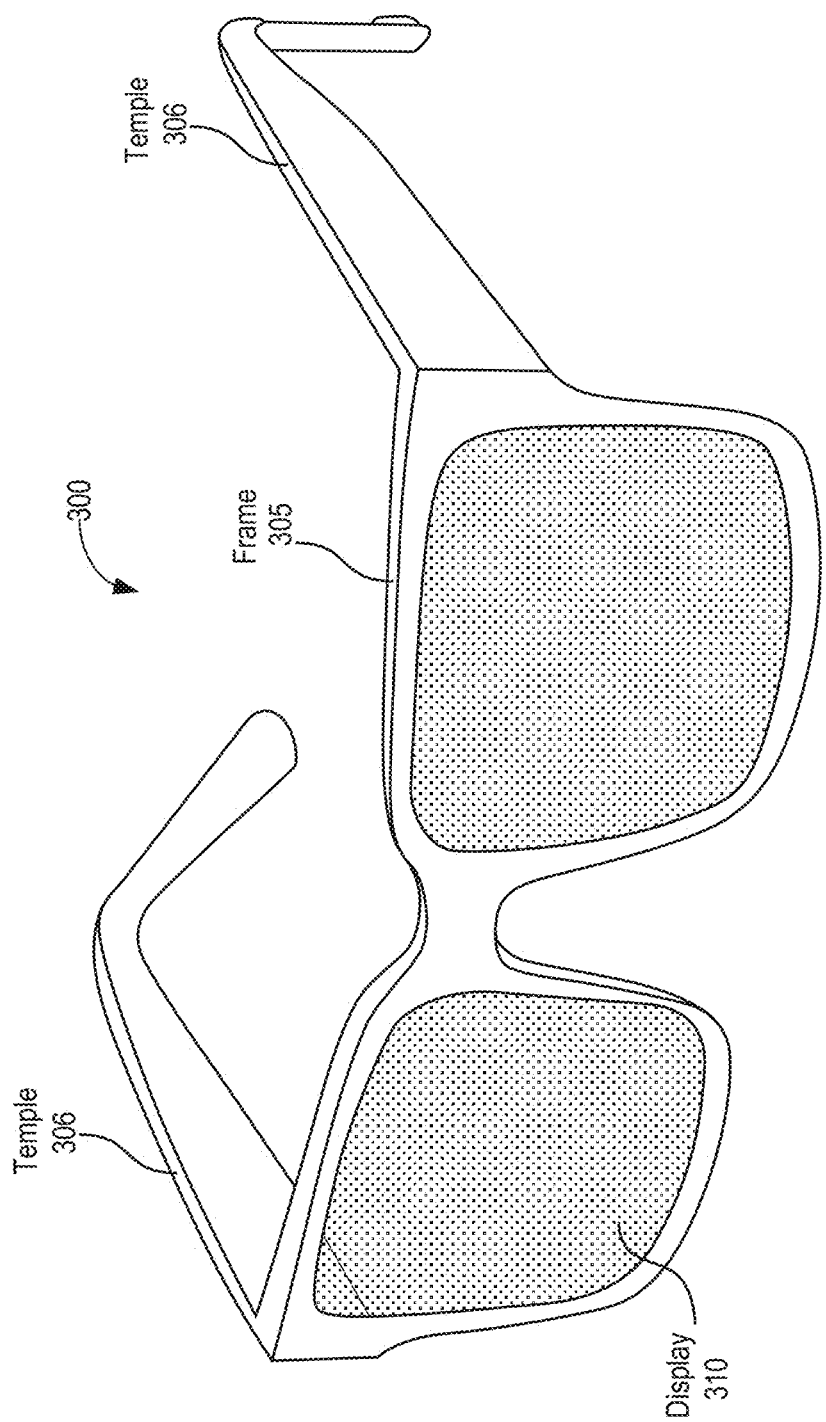
FIGS. 3A and 3B illustrate various views of a near-eye display device in the form of a pair of glasses, according to an example.
Figure 3B:
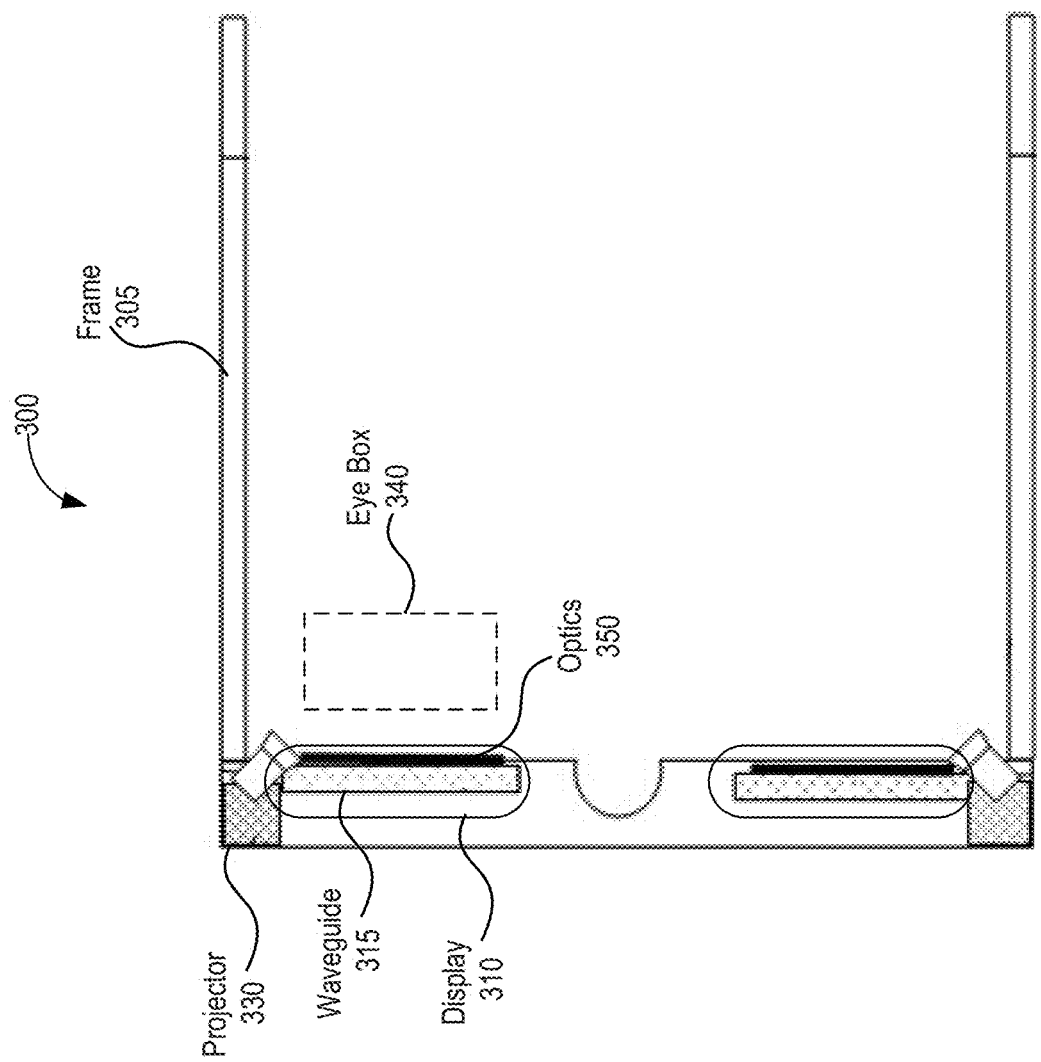

FIGS. 3A and 3B illustrate various views of a near-eye display device 300 in the form of a pair of glasses (or other similar eyewear), according to an example. FIG. 3A is a perspective view, and FIG. 3B is a top view, of the near-eye display device 300 in the form of a pair of glasses (or other similar eyewear), according to an example. In some examples, the near-eye display device 300 may be a specific implementation of the near-eye display 120 of FIG. 1, and may be configured to operate as a virtual reality (VR) system, an augmented reality (AR) system, a mixed reality (MR) system, and/or as part of any such system that uses displays or wearables, or any combination thereof.

As shown in FIG. 3A, in some examples, the near-eye display device 300 may include a frame 305, a display 310, and two temples 306. In some examples, the display 310 may be configured to present media or other content to a user. In some examples, the display 310 may include display electronics and/or display optics, similar to components described with respect to FIGS. 1 and 2A-2C. For example, as described above with respect to the near-eye display 120 of FIG. 1, the display 310 may include a liquid crystal display (LCD) display panel, a light-emitting diode (LED) display panel, or an optical display panel (e.g., a waveguide display assembly). In some examples, the display 310 may also include any number of optical components, such as waveguides, gratings, lenses, mirrors, etc.

In some examples, the near-eye display device 300 may further include various sensors on or within a frame 305, such as, e.g., any number of depth sensors, motion sensors, position sensors, inertial sensors, and/or ambient light sensors. In some examples, the various sensors may include any number of image sensors configured to generate image data representing different fields of views in one or more different directions. In some examples, the various sensors may be used as input devices to control or influence the displayed content of the near-eye display device 300, and/or to provide an interactive virtual reality (VR), augmented reality (AR), and/or mixed reality (MR) experience to a user of the near-eye display device 300. In some examples, the various sensors may also be used for stereoscopic imaging or other similar application.

In some examples, the near-eye display device 300 may further include one or more illuminators to project light into a physical environment. The projected light may be associated with different frequency bands (e.g., visible light, infra-red light, ultra-violet light, etc.), and may serve various purposes. In some examples, the one or more illuminators may be used as locators, such as the one or more locators 126 described above with respect to FIG. 1. In some examples, the near-eye display device 300 may also include a camera or other image capture unit. The camera, for instance, may capture images of the physical environment in the field of view. In some instances, the captured images may be processed, for example, by a virtual reality engine (such as, e.g., the virtual reality engine 116 of FIG. 1) to add virtual objects to the captured images or modify physical objects in the captured images, and the processed images may be displayed to the user by the display 310 for augmented reality (AR) and/or mixed reality (MR) applications.

In some examples, a majority of electronic components of the near-eye display device 300 in the form of a pair of glasses may be included in the frame 305 of the glasses (e.g., a top bar, a bridge, a rim, a lens, etc.). Examples of such electronic components include, but are not limited to, a camera, a projector, a speaker, a battery, a microphone, and a battery management unit (BMU). In some examples, a battery management unit (BMU) may be an electronic system that may be used to manage charging and discharging of a battery (e.g., a lead acid battery). In some examples, the battery management unit (BMU) may, among other things, monitor a state of the battery, determine and report data associated with the battery, and provide environmental control(s) for the battery.

In some examples, the temples 306 may be provided with a tapering profile, based on design considerations for the specific implementation. In such examples, the tapered temples may be utilized to house various electronic components. For example, in some cases, a microphone or speaker may often be placed towards a rear of a temple arm, near a user's ear, and as such, in many cases, a battery may be more likely to be placed near a front of the temple arm.

In some examples, the functionality described herein may be used to combine the view of an environment external to the near-eye display device 300 and artificial reality content (e.g., computer-generated images). In such examples, the near-eye display device 300 may augment images of a physical, real-world environment external to the near-eye display device 300 with generated and/or overlaid digital content (e.g., images, video, sound, etc.) to present an augmented reality to a user.

As shown in FIG. 3B, in some examples, the near-eye display device 300 may include a frame 305 and a display 310 having a waveguide 315 coupled to a projector 330 and optics 350. In some examples, light from a surrounding environment of the near-eye display device 300 may traverse a "see-through" region of the waveguide 315 in the display 310 to reach a user's eyes (located somewhere within an eye box 340), while images are also projected for the user to see as part of an augmented reality (AR) display and/or a mixed reality (MR) display. In such examples, the light of images projected by the projector 330 may be coupled into a transparent substrate of the waveguide 315, propagate within the waveguide 315, be coupled with light from the user's actual environment, and be directed out of the waveguide 315 at one or more locations towards a user's eye(s) located within the eye box 340.

Also as shown in FIG. 3B, the eye box 340 may be a two-dimensional box that may indicate the various possible positions of the user's eye from which a displayed image from an image source may be viewed. In some instances, for a near-eye display system, it may generally be desirable to expand an eye box, reduce display haze, improve image quality (e.g., resolution and contrast), reduce physical size, increase power efficiency, and increase or expand field of view (FOV). As used herein, "field of view" (FOV) may refer to an angular range of an image as seen by a user, which is typically measured in degrees as observed by one eye (for a monocular head-mounted display (HMD)) or both eyes (for binocular head-mounted displays (HMDs)).

In various examples according to the present disclosure, the waveguide 315 may be geometric, reflective, refractive, polarized, diffractive, and/or holographic, as would be understood of one of ordinary skill in the art, and may use any one or more of macro optics (such as, e.g., traditional optics, freeform prisms, and geometrical waveguide techniques, which may be based on Snell's law of reflection and refraction), micro optics (such as, e.g., diffractive grating techniques), and/or nano optics (such as, e.g., metalenses and/or metasurfaces, which may be based on the phase modulation effects of nanoscale structures).

Generally speaking, a diffractive waveguide system may comprise a light source, such as the projector 330, and a planar waveguide element, such as the waveguide 315, that integrates an in-coupling diffractive grating and an out-coupling diffractive grating, as well as optics, such as optics 350, for projecting both the virtual image and the "see-through" real world scene to the user's eye. In such examples, the waveguide 315 may use the in-coupling diffractive grating to receive the light projected by the projector 330, and the received light may propagate through the waveguide 315, bouncing between the inner surfaces of the waveguide 315 via total internal reflection (TIR), before exiting through the out-coupling diffractive grating and being projected into the user's eye through the optics 350. In some examples, the diffractive gratings may have a periodic structural form and may be, for example, surface relief gratings (SRG), volume hologram gratings (VHG), and/or polarization volume gratings (PVG). In various examples of the present disclosure, the projector 330, the waveguide 315, and/or the optics 350 may be integrated, in whole or in part, into a single module or assembly.

In some examples, the waveguide 315 may be comprised of two parallel transparent/semi-transparent elements between which a liquid crystal forms a thin film. In some examples, the liquid crystal may be a nematic liquid crystal, a cholesteric liquid crystal, or any liquid crystal capable of manipulation by the application of an electric field, as would be understood by one of skill in the art. In some examples, light sources/emitters may be positioned adjacent to the liquid crystal such that their light is refracted through the liquid crystal medium, to which an electric field is applied by a thin film of electrically conductive and semi-transparent material to manipulate the liquid crystal and thusly the light being projected therethrough. In other examples, at least one transparent layer in the waveguide 315 may be formed of optical polymers, plastic, glass, transparent wafers (e.g., silicon carbide (SiC) wafers), amorphous silicon, silicon oxide (SiO$_2$), silicon nitride (SiN), titanium oxide (TiO), and/or any other transparent materials used for such a purpose, as would be understood by one of ordinary skill in the art.

In some examples, the projector 330 may include any suitable light source configured to generate a coherent or partially coherent light, such as, e.g., a laser diode, a vertical cavity surface emitting laser (VCSEL), a light emitting diode (LED), or any combination thereof. In some examples, the light source may be a panel, such as a liquid crystal display (LCD) panel, a liquid-crystal-on-silicon (LCoS) display panel, an organic light-emitting diode (OLED) display panel, a micro light-emitting diode (micro-LED) display panel, a digital light processing (DLP) display panel, a laser scanning display panel, or any combination thereof. In some embodiments, the projector 330 may include a self-emissive panel, external source, a micro-light emitting diodes (mLED), and/or a display panel of mLEDs.

In some examples, the optics 350 may be formed of optical polymers, plastic, glass, transparent wafers (e.g., silicon carbide (SiC) wafers), amorphous silicon, silicon oxide (SiO$_2$), silicon nitride (SiN), titanium oxide (TiO), optical nylon, carbon-polymers, and/or any other suitably optically transparent materials used for such a purpose, as would be understood by one of ordinary skill in the art. In some examples, the optics 350, alone or in combination with other components (e.g., the waveguide 315 and/or the projector 330) may operate and/or be constructed similarly to the display optics 124 in FIG. 1 and/or the display optics discussed in reference to FIGS. 2A-2C.

In a near-eye display device, such as, e.g., the near-eye display device 300 in the form of a pair of glasses in FIGS. 3A-3B, the near-eye display device in the form of a head-mounted display (HMD) device 200 in FIGS. 2A-2C, and/or the near-eye display device 120 which is part of the artificial reality system 100 in FIG. 1, the user experience (UX) in terms of, for example, blurry vision and general discomfort/fatigue, etc., and equipment performance in terms of, for example, effective eye tracking, etc., may be greatly affected by deficient ocular hydration. For instance, the reflections used by the eye tracking system may be deleteriously affected by the dryness of the user's eyes, thereby degrading the performance of the eye tracking system.

FIG. 4 illustrates the tear film layers of the surface of the eye relevant to the problems ameliorated by systems, apparatuses, and methods according to examples of the present disclosure. As used herein, the term "tear film" may refer to the fluid layer(s) covering the ocular surface, which is responsible for ocular surface comfort, mechanical, environmental, and immune protection, and epithelial health, as well as serving forming a smooth refractive surface for vision. In FIG. 4, an eye is shown with a close-up of a portion of the eye, where three layers are identified, starting from the outermost layer: a lipid layer 410, an aqueous layer 420, and a mucin layer. In the lipid layer 410, lipids/oils may stabilize the tear film. Many forms of dry eye are caused by the lack of sufficient lipids in the lipid layer 410, which may result in the eye's moisture evaporating too quickly. The aqueous layer 420 is the largest portion of the tear film, responsible for supplying the moisture the eye needs to be comfortable. The mucin layer 430 is the innermost layer of the tear film and consists of proteins called mucins that coat the eye and allow the aqueous layer 420 to the otherwise water-repellent cornea of the eye. All three layers are important and crucial for creating an ideal tear film for moist, healthy eyes. If any of the three layers become depleted, the tear film cannot properly coat the eye and dry spots may form, causing discomfort.

Figure 5:
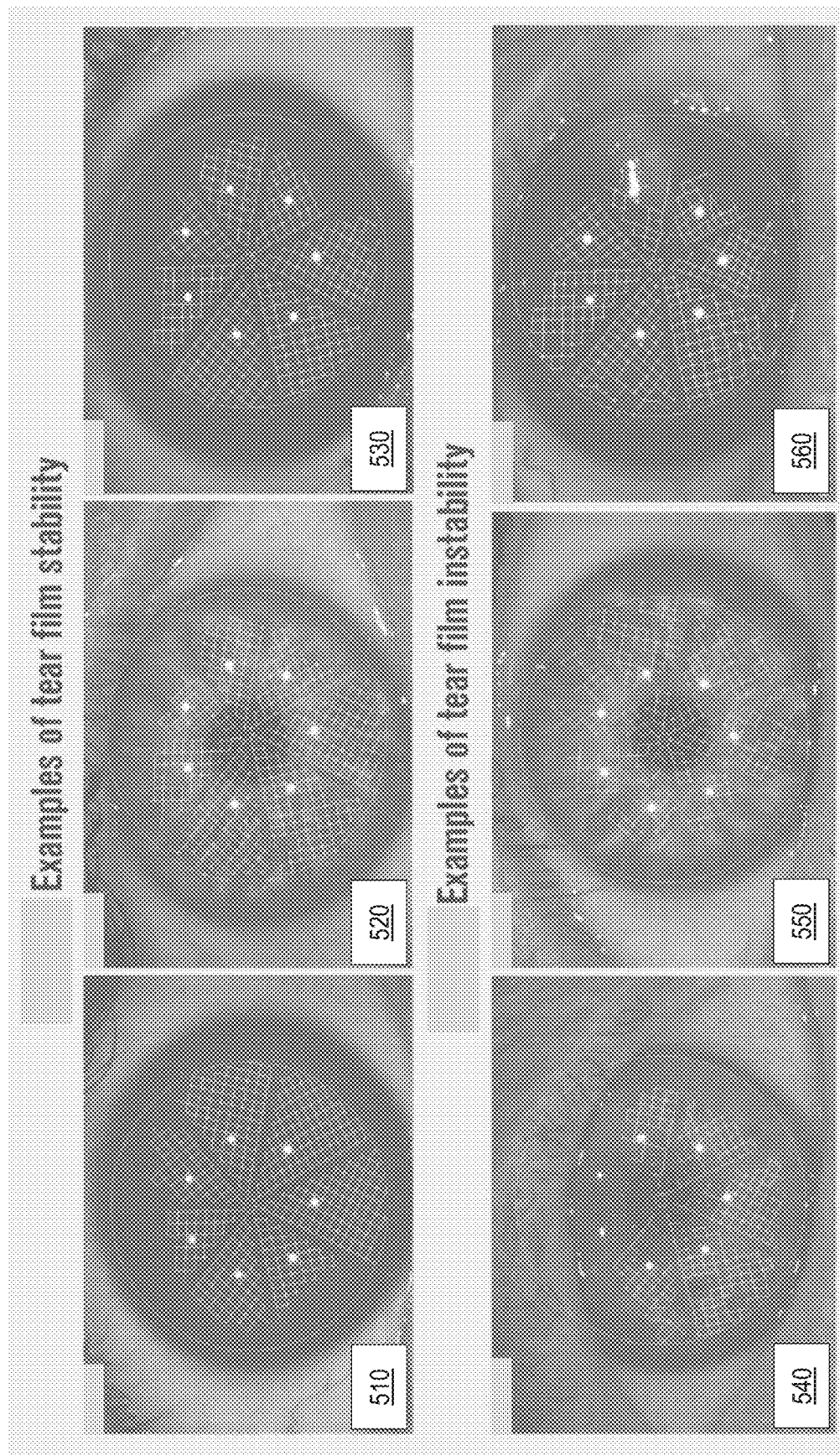
FIG. 5 illustrates examples of tear film stability and tear film instability, the which may be ameliorated by systems, apparatuses, and methods according to examples of the present disclosure.

FIG. 5 illustrates examples of tear film stability and tear film instability, the which may be ameliorated by systems, apparatuses, and methods according to examples of the present disclosure. In each of the photos in FIG. 5, the surface of an eye is mapped with seven topographical "pie slices," each shown by a grid pattern with a centroid in the form of a white dot. In FIG. 5, pictures 510, 520, and 530 illustrate examples of tear film stability, while pictures 540, 550, and 560 illustrate examples of tear film instability. As shown in pictures 510, 520, and 530 of FIG. 5, the topographical pie slices mapping the surface of the eye are relatively whole, continuous, and uniform, indicating well hydrated eye surfaces, i.e., tear film stability. As shown in pictures 540, 550, and 560 of FIG. 5, the topographical pie slices mapping the surface of the eye are relatively ragged/partial/missing large sections, not continuous, and non-uniform, indicating eye surfaces which are not well hydrated, i.e., tear film instability.

Tear film instability may have a detrimental effect on the eye tracking system of a near-eye display device, particularly in an eye tracking system employing Photosensor Oculography (PSOG). In PSOG, one or more photosensors may measure the amount of reflected light or "glints" when the eye rotates. More specifically, the photosensors may measure the size, shape, location, intensity, and/or positioning of the glints in order to determine where the user's eye is presently directed/focused. Both the intensity and shape of the glints may be affected by the quality of the tear film and the hydration of the eye, thereby reducing the accuracy and overall performance of the eye tracking system, which may in turn detrimentally affect the UX. Moreover, as discussed above, ocular dehydration may have more fundamental effects on the UX of a user wearing a near-eye display device. Such effects may range from mild discomfort to dry eyes, blurry vision, and/or more general discomfort and user fatigue. As used herein, "dry eye(s)," "tear film instability," "lack of ocular hydration," "ocular dehydration," "poor tear film quality," and/or any other terms indicating an inadequate, insufficient, unsatisfactory, and/or otherwise deficient condition of the quality of the tear film which may thereby affect eye tracking and/or the UX may be used interchangeably.

According to examples of the present disclosure, a near-eye display device, such as, e.g., the near-eye display device 120 which is part of the artificial reality system 100 in FIG. 1, the near-eye display device in the form of the head-mounted display (HMD) device 200 in FIGS. 2A-2C, and/or the near-eye display device 300 in the form of a pair of glasses in FIGS. 3A-3B, may have an ocular hydration sensor/reflectometer system for continuous measurement of ocular hydration and tear film stability levels. In some examples, the ocular hydration sensor/reflectometer system for continuous measurement of ocular hydration and tear film stability levels operates in conjunction with the eye tracking system of the near-eye display device. In some examples, the ocular hydration sensor/reflectometer system is integrated into the eye tracking system of the near-eye display device. In other examples, part(s) or all of the ocular hydration sensor/reflectometer system may be separate from the eye tracking system and may instead be integrated with other components/systems of the near-eye device, such as, e.g., the AR/VR display system, the waveguide, and/or the LCD backlight of the display. In yet further examples, part(s) or all of the ocular hydration sensor/reflectometer system may be separate and independent components/system on the near-eye display device, such as, e.g., a separate/independent diffuse light source which may flood the surface area of the eye.

In some examples, an ocular hydration sensor/reflectometer system may be coupled to an eye tracking system of a near-eye display device for continuous measurement of ocular hydration/tear film stability levels, ensuring that the conditions for measurement are normalized to account for environment light, pupil dilation, and eye position in respect to the ocular hydration sensor/reflectometer system. In some examples, the ocular hydration sensor/reflectometer system may measure one or more hydration-related biomarkers, which may be used with tear film reflectivity-related metrics to determine whether to prompt the user to take action such as, for example, to blink or to take a break. In some examples, the ocular hydration sensor/reflectometer system may measure reflection efficiency, which then may be used to re-calibrate parameters of the eye tracking system such as, for example, adjusting the exposure timing of the eye tracking camera, adjusting the power of the eye tracking projector, etc., as would be understood by one of ordinary skill in the art. In some examples, the one or more hydration-related biomarkers may include, e.g., tear film thickness (and/or the thickness of one of its component layers), the capillary pattern on the sclera (e.g., red eye), and/or any other indicators/signals of hydration levels (whether measured roughly instantaneously or over time), as would be understood by one of ordinary skill in the art.

Figure 6:
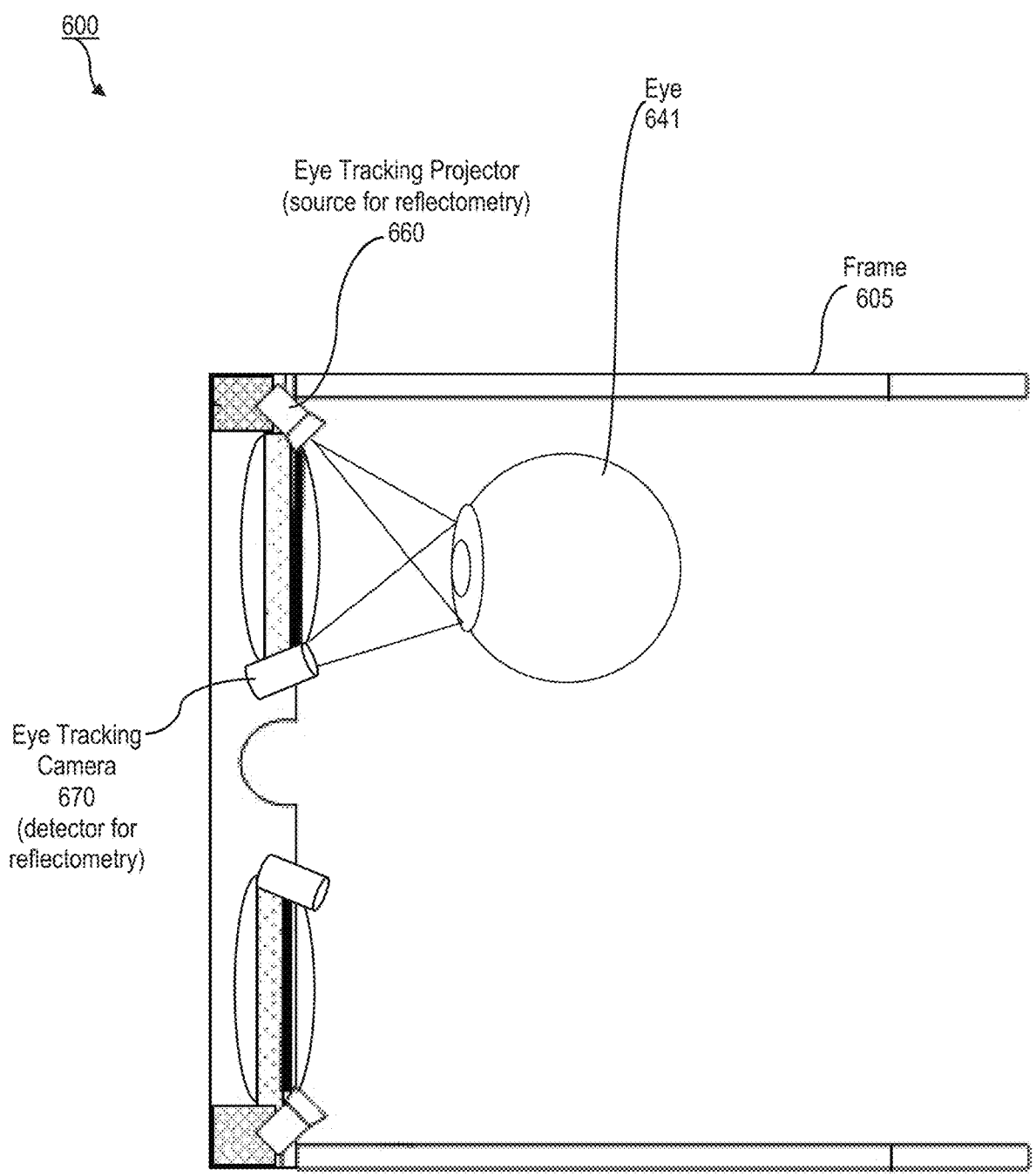
FIG. 6 illustrates a reflectometer integrated into an eye tracking system acting as an ocular hydration sensor/reflectometer system in a near-eye display device according to an example.

FIG. 6 illustrates a reflectometer integrated into an eye tracking system acting as an ocular hydration sensor/reflectometer system in a near-eye display device according to an example. In FIG. 6, a near-eye display device 600 takes the form of a pair of eyeglasses with an eye tracking system which may include an eye tracking projector 660 and an eye tracking camera 670 disposed in a frame 605 of the detector. The eye tracking projector 660 may project light onto an eye 641, the eye tracking camera 670 may receive the reflections from the eye 641 of that projected light, and an eye tracking system (such as, for example, the eye tracking unit 130 and/or the eye tracking module 118 of FIG. 1) tracks where a pupil of the eye 641 is directed. Accordingly, the eye tracking projector 660 may be performing a dual role of both eye tracking and illuminating the eye for purposes of reflectometric measurements.

In some examples, a reflectometer may be integrated into the eye tracking projector 660 as an illumination source for the reflectometry and the eye tracking camera 670 as a photodetector for the reflectometry. In some examples, signal processing for the reflectometry may be performed, wholly or in part, by the eye tracking system (such as, e.g., the eye tracking unit 130 and/or the eye tracking module 118 of FIG. 1). In some examples, signal processing for the reflectometry may be performed, wholly or in part, by a separate and independent microprocessor and/or other pre-existing processing components disposed in the frame 605 of the near-eye display device 600.

In some examples, the eye tracking system may be used to ensure consistent measuring conditions, such as, e.g., maintaining approximately the same gaze angle, checking that the eye remains open, etc., as would be understood by one of ordinary skill in the art. Accordingly, the ocular hydration sensor/reflectometer may measure the intensity of the reflection from the eye of the projected light while the eye 641 is open and remains in the same position. In some examples, the ocular hydration sensor/reflectometer measures the efficiency of the reflection and how it changes over time and, in examples where the eye tracking camera 670 is the photodetector, the ocular hydration sensor/reflectometer may also measure the shape of any glints to measure the surface texture of the tear film. In some examples, the measurements from the ocular hydration sensor/reflectometer are used to adjust the intensity of illumination of the eye tracking projector 660 and/or the exposure time of the eye tracking camera 670 in order to optimize the performance of the eye tracking system.

In some examples, the ocular hydration sensor/reflectometer may measure the tear film reflectance as a function of wavelength and then the tear film thickness may be determined by best-fitting the reflectance-wavelength curve. In some examples, interferometry may be used to estimate the tear film thickness based on surface reflection patterns and dynamics. In some examples, meibography, i.e., using images of the meibomian gland structure to make a quantitative analysis, may be employed to determine the tear film thickness.

In some examples, measurement(s) from the ocular hydration sensor/reflectometer may be combined with measurements from other health sensors to determine whether the user should be prompted to change behavior, e.g., by blinking or taking a break. In some examples, measurement(s) from the ocular hydration sensor/reflectometer may be collected and analyzed over time in order to monitor the health of the user's eyes.

As mentioned above and discussed in reference to further examples below, the light source for the reflectometer according to the present disclosure may include other light sources besides the eye tracking projector 660, and the photodetector for the reflectometer according to the present disclosure may include other photodetectors besides the eye tracking camera 670. For example, the light source for the reflectometer may be a point source or an array of spatially distributed light sources, and the photodetector for the reflectometer may be single, simple photodetector or an array of photodetectors, which also may be spatially distributed. As stated above, in some examples, the reflectometry processing/measurement may be performed, wholly or in part, by the eye tracking system (such as, e.g., the eye tracking unit 130 and/or the eye tracking module 118 of FIG. 1), by a separate and independent microprocessor, and/or by another pre-existing processing component disposed in the near-eye display device 600.

Figure 7:
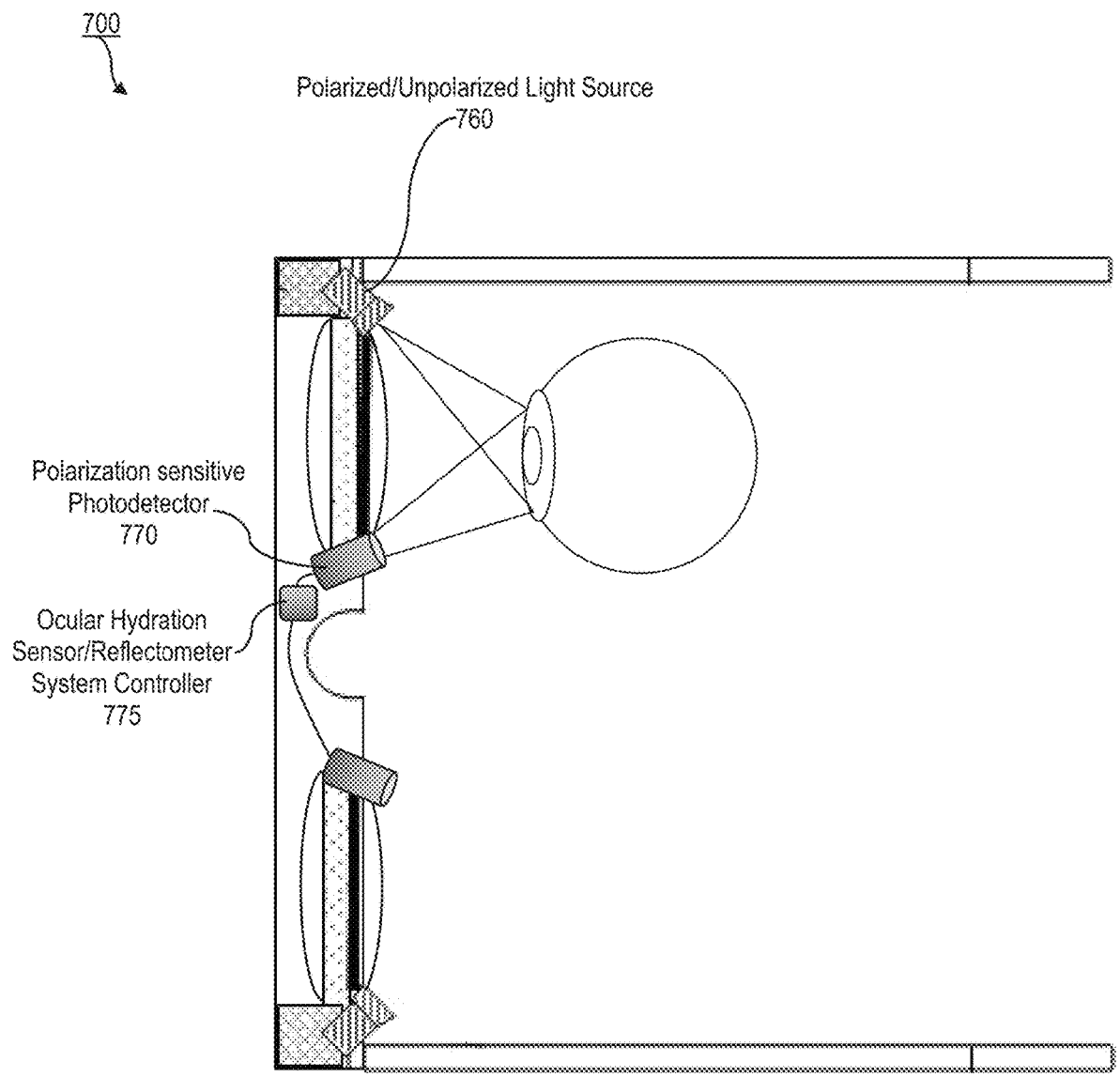
FIG. 7 illustrates an ocular hydration sensor/reflectometer system implemented at least in part as a polarization sensitive photodetector in a near-eye display device according to an example.

FIG. 7 illustrates an ocular hydration sensor/reflectometer system implemented at least in part as a polarization sensitive photodetector in a near-eye display device according to an example. In FIG. 7, a near-eye display device 700 takes the form of a pair of eyeglasses which may include a polarized/unpolarized light source 760, a polarization sensitive photodetector 770, and an ocular hydration sensor/reflectometer system controller 775.

In FIG. 7, as long as the type of polarization of the polarized/unpolarized light source 760 is known (e.g., linearly polarized, circularly polarized, or unpolarized), the polarization sensitive photodetector 770 may de-couple specular reflections (which are from the tear film) and diffuse reflections (which are from the sub-surface, i.e., the physical surface of the eye, which may be monitored for eye tracking). This ability to separate out the two types of reflection results in much more accurate measurements (of both the tear film and the eye's physical surface). Similarly to FIG. 6, the polarization sensitive photodetector 770 of the ocular hydration sensor/reflectometer system in FIG. 7 may receive reflections from the projected light on the tear film of the eye, and may provide that as input to the ocular hydration sensor/reflectometer system controller 775 which takes measurements which may be used to adjust the intensity of illumination of the eye tracking projector and/or the exposure time of the eye tracking camera in order to optimize the performance of the eye tracking system.

In some examples, the polarized/unpolarized light source 760 may be further modulated in time and the polarization sensitive photodetector 770 may further be a high-speed detector with frequency lock-in detection. In such examples, the additional modulation and detection may provide increased robustness by allowing the ocular hydration sensor/reflectometer system to separate out light noise from the local environment. In some examples, the polarized/unpolarized light source 760 may include any of the projectors described in reference to the near-eye display device 120 in FIG. 1, the head-mounted display (HMD) device 200 in FIGS. 2A-2C, and/or the near-eye display device 300 in FIGS. 3A-3B, or an added separate and independent light source such as the polarized/unpolarized light source 760 shown in the near-eye display device 700. Similarly, in some examples the polarization sensitive photodetector 770 may include any camera (such as, e.g., the eye tracking camera 670 in FIG. 6), photodetector, or suitable sensor described in reference to the near-eye display device 120 in FIG. 1, the head-mounted display (HMD) device 200 in FIGS. 2A-2C, and/or the near-eye display device 300 in FIGS. 3A-3B, instead of, or in addition to, the added separate and independent polarization sensitive photodetector 770 such as shown in the near-eye display device 700.

In some examples, the ocular hydration sensor/reflectometer system controller 775 of the ocular hydration sensor/reflectometer system of FIG. 7 may be implemented, in whole or in part, in the eye tracking system in a manner similar to the system shown in FIG. 6 and/or in another pre-existing processing component disposed in the near-eye display device 700. In examples according to the present disclosure, the reflectometry processing/measurement (whether performed, in whole or in part, by the ocular hydration sensor/reflectometer system controller 775 or another component of the near-eye display device 700) may be implemented by at least one of any type of application, program, library, script, task, service, process, or any type or form of executable instructions executed on hardware such as circuitry that may include digital and/or analog elements (e.g., one or more transistors, logic gates, registers, memory devices, resistive elements, conductive elements, capacitive elements, and/or the like, as would be understood by one of ordinary skill in the art). In some examples, the hardware and data processing components used to implement the various processes, operations, logic, and circuitry described in connection with the examples described herein may be implemented with a general purpose single- and/or multi-chip processor, a single- and/or multi-core processor, a digital signal processor (DSP), an application specific integrated circuit (ASIC), a field programmable gate array (FPGA), or other programmable logic device, discrete gate or transistor logic, discrete hardware components, and/or any combination thereof suitable to perform the functions described herein. A general purpose processor may be any conventional processor, microprocessor, controller, microcontroller, and/or state machine. In some examples, the memory/storage may include one or more components (e.g., random access memory (RAM), read-only memory (ROM), flash or solid state memory, hard disk storage, etc.) for storing data and/or computer-executable instructions for completing and/or facilitating the processing and storage functions described herein. In some examples, the memory/storage may be volatile and/or non-volatile memory, and may include database components, object code components, script components, or any other type of information structure suitable for implementing the various activities and storage functions described herein.

Figure 8A:
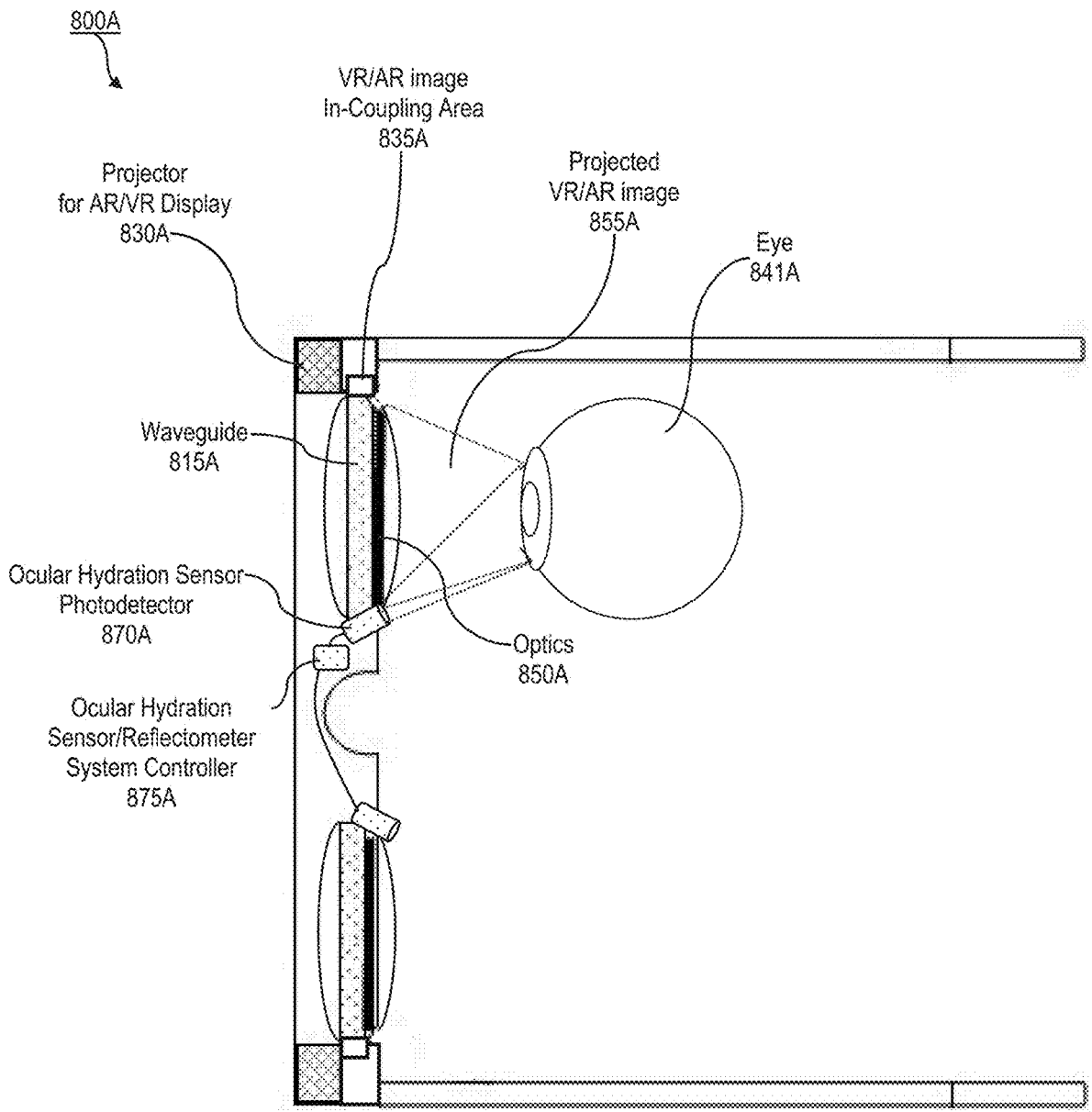
FIG. 8A illustrates an ocular hydration sensor/reflectometer system where the light source is an AR/VR display of a near-eye display device according to an example.

FIG. 8A illustrates an ocular hydration sensor/reflectometer system where the light source is an AR/VR display of a near-eye display device according to an example. In FIG. 8A, a near-eye display device 800A takes the form of a pair of eyeglasses which includes a projector 830A for AR/VR display, an ocular hydration sensor photodetector 870A, and an ocular hydration sensor/reflectometer system controller 875A. Similarly to the projector 330 discussed above in reference to FIG. 3B, the AR/VR image display projector 830A may project light directly into an in-coupling grating of a waveguide 815A in an VR/AR image in-coupling area 835A, and then the projected light propagates may propagate internally in the waveguide 815A until exiting through an out-coupling grating into optics 850A, which projects the light as a generated VR/AR image 855A to a user's eye 841A.

In some examples, the reflections of the projected AR/VR image 855A—i.e., reflections from the eye 841A of the displayed AR/VR content itself—may be received by the ocular hydration sensor photodetector 870A and then may be used by the ocular hydration sensor/reflectometer system controller 875A to take glint measurements of the tear film. In some examples, hidden frames and/or non-visible light may be projected with the projected AR/VR image 855A and the reflections from the projected hidden frames and/or non-visible light may be received by the ocular hydration sensor photodetector 870A and then used by the ocular hydration sensor/reflectometer system controller 875A to take glint measurements of the tear film. In examples using hidden frames/non-visible light and/or the displayed content itself, the expected reflection pattern is known (based on the known projection) and thus glint measurements may be made by the ocular hydration sensor/reflectometer system controller 875A. In examples where the light source for the AR/VR image display projector 830A is an LCD, the polarization of the LCD may be used by the ocular hydration sensor photodetector 870A and/or the ocular hydration sensor/reflectometer system controller 875A to selectively isolate glint reflections from other light noise. In some examples, the light source for the AR/VR image projector 830A may be a laser scanning source for retinal projection.

In some examples, the ocular hydration sensor photodetector 870A of the ocular hydration sensor/reflectometer system of FIG. 8A may be any camera, photodetector, or suitable sensor described in reference to the near-eye display device 120 in FIG. 1, the head-mounted display (HMD) device 200 in FIGS. 2A-2C, and/or the near-eye display device 300 in FIGS. 3A-3B, instead of, or in addition to, the added separate and independent ocular hydration sensor photodetector 870A shown in FIG. 8A. Similarly to FIGS. 6 and 7, the ocular hydration sensor photodetector 870A of the ocular hydration sensor/reflectometer system in FIG. 8A receives reflections from the tear film, and provides that input to the ocular hydration sensor/reflectometer system controller 875A to take measurements which may be used to adjust the intensity of illumination of the eye tracking projector and/or the exposure time of the eye tracking camera in order to optimize the performance of the eye tracking system. Similarly to FIGS. 6 and 7, the ocular hydration sensor/reflectometer system controller 875 of the ocular hydration sensor/reflectometer system of FIG. 8A may be implemented, in whole or in part, in an eye tracking system in a manner similar to the system shown in FIG. 6, in another pre-existing processing component disposed in the near-eye display device 800A, and/or in an independent and separate processor such as the ocular hydration sensor/reflectometer system controller 875 shown in FIG. 8A.

Figure 8B:
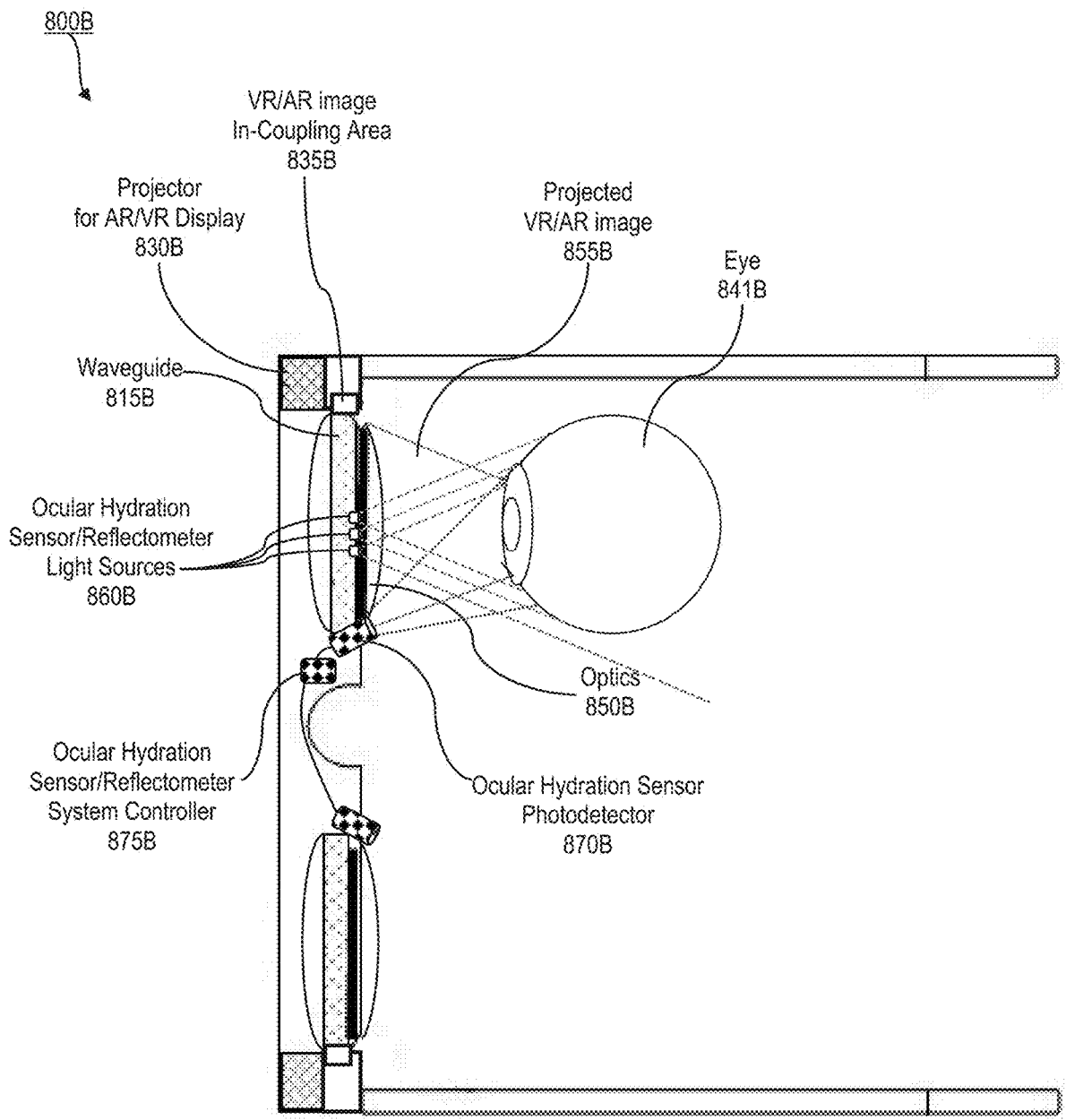
FIG. 8B illustrates an ocular hydration sensor/reflectometer system where the light source is integrated at least in part into an AR/VR display of a near-eye display device according to an example.

FIG. 8B illustrates an ocular hydration sensor/reflectometer system where the light source is integrated at least in part into an AR/VR display of a near-eye display device according to an example. In FIG. 8B, a near-eye display device 800B takes the form of a pair of eyeglasses which may include a projector 830B for AR/VR display, ocular hydration sensor/reflectometer light sources 860B, an ocular hydration sensor photodetector 870B, and an ocular hydration sensor/reflectometer system controller 875B. Similarly to the AR/VR image display projector 830A discussed in FIG. 8A above, the AR/VR image display projector 830B may project light directly into an in-coupling grating of a waveguide 815B in an VR/AR image in-coupling area 835B, and then the projected light may propagate internally in the waveguide 815B until exiting through an out-coupling grating into optics 850B, which projects the light as a generated VR/AR image 855B to a user's eye 841B.

In various examples, the ocular hydration sensor/reflectometer system light sources 860B may be integrated into the AR/VR image display projector 830B, the display waveguide 815B, the optics 850B, and/or any other component of the AR/VR image display system in the near-eye display device 800B. In some examples, as shown in FIG. 8B, the ocular hydration sensor/reflectometer light sources 860B may be integrated directly into the waveguide 815B by being directly embedded into the transparent element facing the eye 841B. Similarly to FIGS. 6, 7, and 8A, the ocular hydration sensor photodetector 870B of the ocular hydration sensor/reflectometer system in FIG. 8B receives reflections from the tear film and provides that input to the ocular hydration sensor/reflectometer system controller 875A which uses the input to take measurements which may be used to adjust the intensity of illumination of the eye tracking projector and/or the exposure time of the eye tracking camera in order to optimize the performance of the eye tracking system.

In some examples, a separate infrared (IR) channel may be projected by a light source located adjacent/within the AR/VR image display projector 830B onto the eye 841B. In some examples, a few pixels of the light display source of the AR/VR image display projector 830B for the projected AR/VR image 855B may be used to project IR or near-IR (NIR) light. In such examples, reflections of the projected IR/NIR light from the tear film of the eye 841B may be received by an ocular hydration sensor photodetector 870B and then may be used by an ocular hydration sensor/reflectometer system controller 875B to take glint measurements of the tear film. In some examples, sparse IR LEDs may be integrated with the LCD backlight of the AR/VR display in order to project IR light to be reflected by the tear film of the eye 841B.

In some examples, the ocular hydration sensor photodetector 870B of the ocular hydration sensor/reflector system of FIG. 8B may be any camera, photodetector, or suitable sensor described in reference to the near-eye display device 120 in FIG. 1, the head-mounted display (HMD) device 200 in FIGS. 2A-2C, and/or the near-eye display device 300 in FIGS. 3A-3B, instead of, or in addition to, the added separate and independent ocular hydration sensor photodetector 870A shown in FIG. 8A. Similarly to FIGS. 6, 7, and 8A, the ocular hydration sensor/reflectometer system controller 875B of the ocular hydration sensor/reflectometer system of FIG. 8B may be implemented, in whole or in part, in an eye tracking system in a manner similar to the system shown in FIG. 6, in another pre-existing processing component disposed in the near-eye display device 800B, and/or in an independent and separate processor such as the ocular hydration sensor/reflectometer system controller 87B shown in FIG. 8B.

Figure 9:
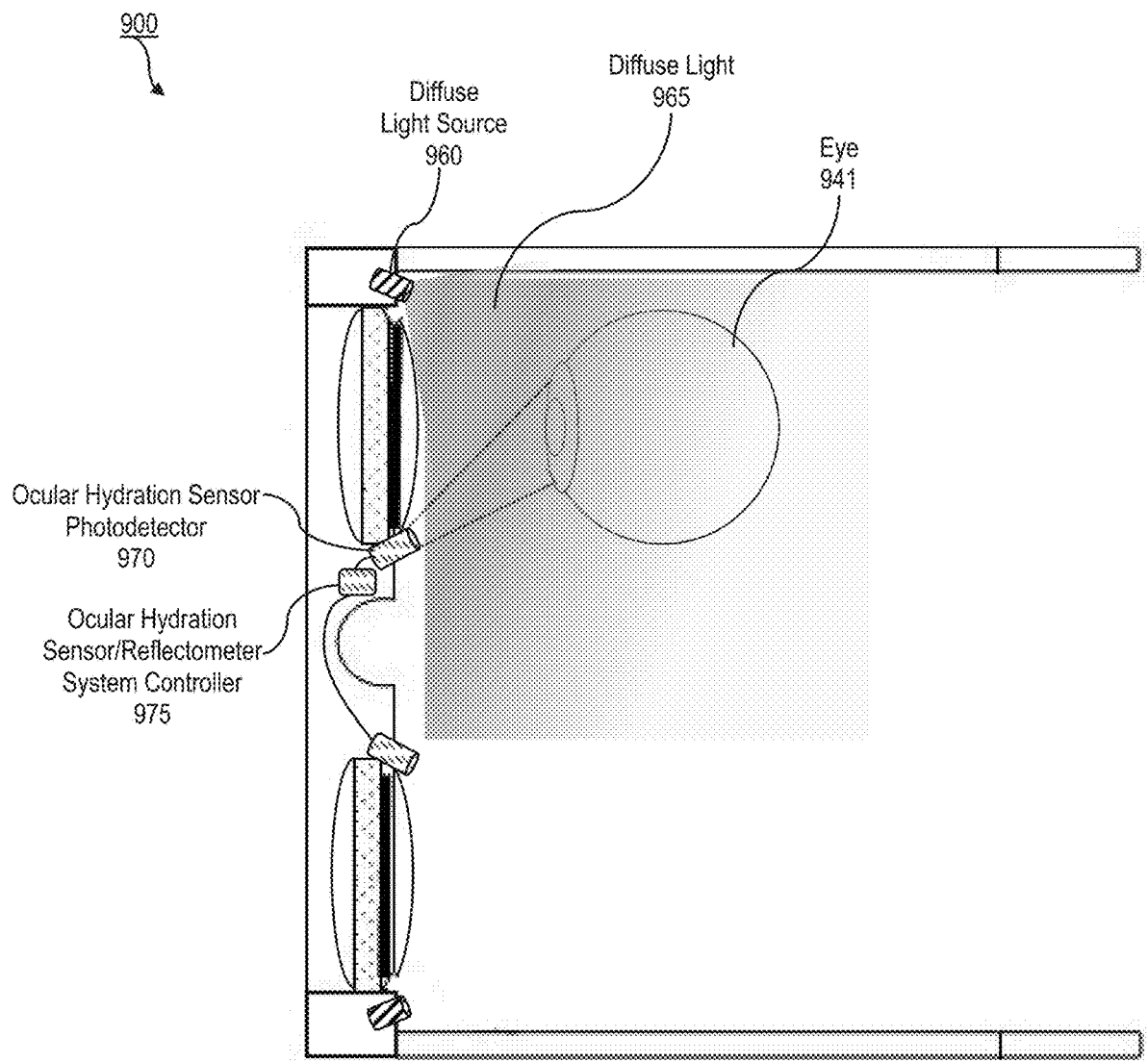
FIG. 9 illustrates an ocular hydration sensor/reflectometer system which uses a diffuse light source in a near-eye display device according to an example.

FIG. 9 illustrates an ocular hydration sensor/reflectometer system which uses a diffuse light source in a near-eye display device according to an example. In FIG. 9, a near-eye display device 900 takes the form of a pair of eyeglasses which may include a diffuse light source 960, an ocular hydration sensor photodetector 970, and an ocular hydration sensor/reflectometer system controller 975. In FIG. 9, the diffuse light source 960 projects diffuse light 965 towards an eye 941. In some examples, reflections from the tear film of the eye 941 may take the form of lines rather than the eye glints which reflect when using non-diffuse light sources. In some examples, the diffuse light source 960 may include one or more outfield light sources, and may project light separated either temporally (e.g., periodically, sequentially, intermittently, etc.) or spectrally (e.g., by wavelength) in order that their reflections be selectively isolated by the ocular hydration sensor photodetector 970 from reflections from other light sources. In some examples, the diffuse light source 960 may include a light pipe, or a multitude of LEDs which flood the eye box area with diffuse light.

Similarly to FIGS. 6 and 7, the ocular hydration sensor photodetector 970 of the ocular hydration sensor/reflectometer system in FIG. 9 may receive reflections of the projected diffuse light 965 from the tear film of the eye, and may provide that as input to the ocular hydration sensor/reflectometer system controller 975 which takes measurements which may be used to adjust the intensity of illumination of the eye tracking projector and/or the exposure time of the eye tracking camera in order to optimize the performance of the eye tracking system. Similarly to FIGS. 6, 7, 8A, and 8B, the ocular hydration sensor/reflectometer system controller 975 of the ocular hydration sensor/reflectometer system of FIG. 9 may be implemented, in whole or in part, in an eye tracking system in a manner similar to the system shown in FIG. 6, in another pre-existing processing component disposed in the near-eye display device 900, and/or as an independent and separate processor such as the ocular hydration sensor/reflectometer system controller 975 shown in FIG. 9. In some examples, the ocular hydration sensor photodetector 970 of the ocular hydration sensor/reflectometer system of FIG. 9 may be any camera, photodetector, or suitable sensor described in reference to the near-eye display device 120 in FIG. 1, the head-mounted display (HMD) device 200 in FIGS. 2A-2C, and/or the near-eye display device 300 in FIGS. 3A-3B, instead of, or in addition to, the added separate and independent ocular hydration sensor photodetector 970 shown in FIG. 9.

Figure 10:
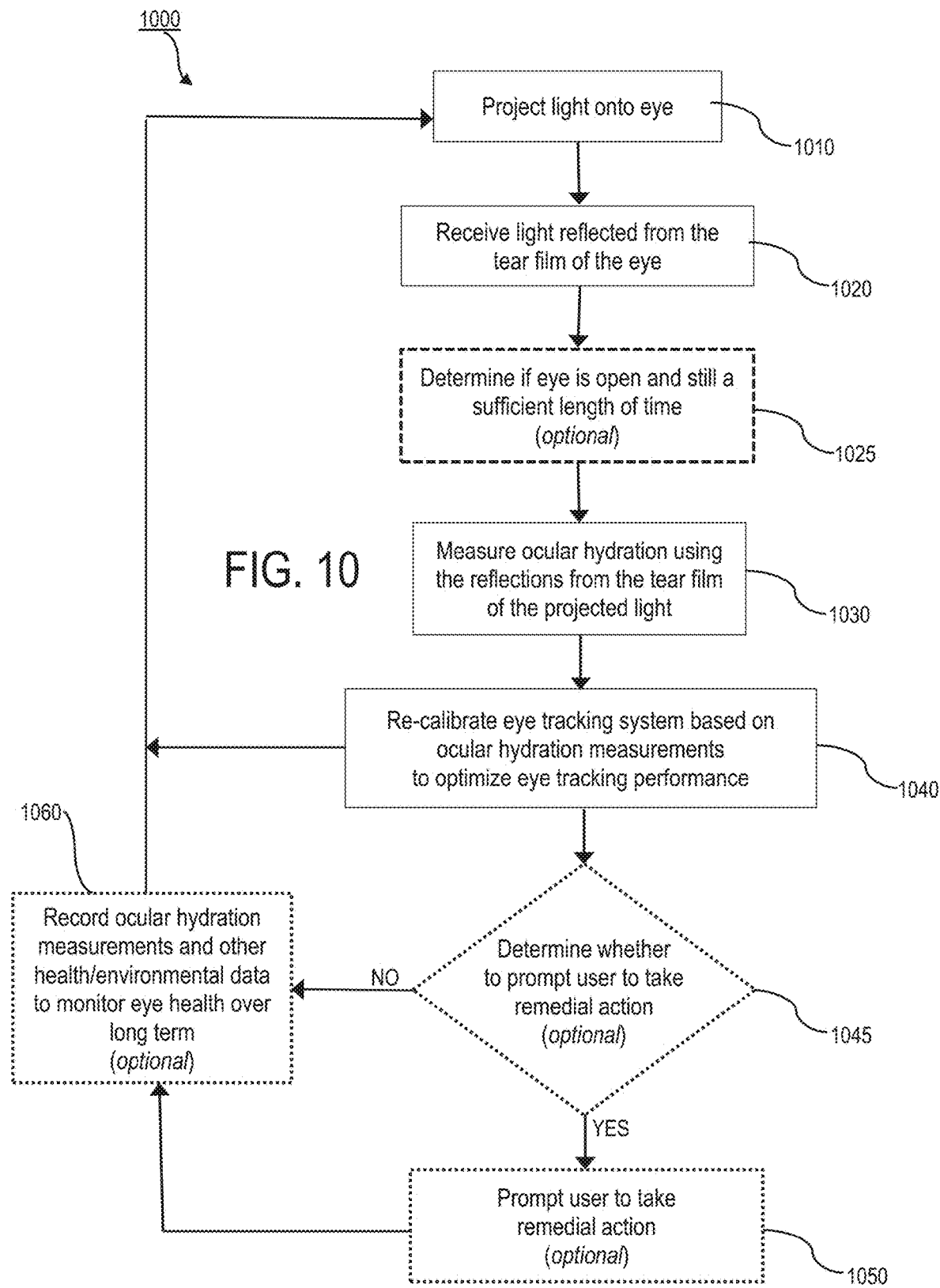
FIG. 10 illustrates a flow diagram for a method of ocular hydration sensing in a near-eye display device, according to an example.

FIG. 10 illustrates a flow diagram for a method of ocular hydration sensing in a near-eye display device, according to an example. The method 1000 shown in FIG. is provided by way of example and may only be one part of an entire process/procedure. The method 1000 may further omit parts of the method not germane to the present disclosure, as would be understood by one of ordinary skill in the art. Each block shown in FIG. 10 may further represent one or more steps, processes, methods, or subroutines, as would be understood by one of ordinary skill in the art. For the sake of convenience and ease of explanation, the blocks in FIG. 10 may refer to the components and/or descriptions of the other figures described herein; however, the method 1000 is not limited in any way to the components, apparatuses, and/or constructions shown in any of the figures described herein. Moreover, in some examples, the components for implementing the ocular hydration sensor/reflectometer system may be located, in whole or in part, in the near-eye display device and/or externally to the near-eye display device (such as, for example, in the input/output interface 140 and/or the console 110 in FIG. 1). In some examples, the ocular hydration sensor/reflectometer system may be implemented/integrated, in whole or in part, in the operating system of the near-eye display device.

At block 1010, an ocular hydration sensor/reflectometer system according to examples of the present disclosure may project light upon a user's eye in a near-eye display device. In some examples, the light source of the ocular hydration sensor/reflectometer system may be, for example, the eye tracking projector 660 of FIG. 6, the polarized/unpolarized light source 760 of FIG. 7, the AR/VR image display projector 830A of FIG. 8A, the ocular hydration sensor/reflectometer light sources 860B of FIG. 8B, and/or the diffuse light source 960 of FIG. 9. In other examples, other light sources may be used, as would be understood by one of ordinary skill in the art.

At block 1020, the ocular hydration sensor/reflectometer system may receive light reflected from the user's eye in block 1010. In some examples, the photodetector of the ocular hydration sensor/reflectometer system may be, for example, the eye tracking camera 670 of FIG. 6, the polarization sensitive photodetector 770 of FIG. 7, the ocular hydration sensor photodetector 870A of FIG. 8A, the ocular hydration sensor photodetector 870B of FIG. 8B, and/or the ocular hydration sensor photodetector 970 of FIG. 9. In other examples, other photodetectors may be used, as would be understood by one of ordinary skill in the art.

Optionally in block 1025 in some examples, the ocular hydration sensor/reflectometer system may determine whether the user's eye is open and motionless long enough to take readings suitable for ocular hydration sensor measurements. In various examples, block 1025 may occur before, after, or during either of blocks 1020 or 1030. In some examples, the eye tracking system may determine whether the user's eye is open and stationary a sufficient length of time. In other examples, an ocular hydration sensor/reflectometer system controller separate from the eye tracking system (such as, e.g. the ocular hydration sensor/reflectometer system controller 775 of FIG. 7; the ocular hydration sensor/reflectometer system controller 875A of FIG. 8A; the ocular hydration sensor/reflectometer system controller 875B of FIG. 8B; or the ocular hydration sensor/reflectometer system controller 975 of FIG. 9) may determine the user's eye has been stationary for the sufficient length of time.

In some examples, the length of time the eye must be stationary may vary according to the specific components and parameters of the near-eye display device being employed. In some examples, the length of time may depend on how many images the ocular hydration sensor photodetector may take in a series in a certain amount of time. For instance, if the ocular hydration sensor photodetector may take a few dozen images in less than a second while the eye is stationary, this may be adequate to perform the following steps in the method 1000. As used herein, 10 to 100 milliseconds of stationary state of the pupil may be sufficient in some cases. In other cases, a small amount (e.g., a few degrees) of motion of the eye ball may be correctible by computer vision algorithms. Thus, such small movements may also be considered as stationary enough in terms of block 1025.

At block 1030, the ocular hydration sensor/reflectometer system may take measurements using the received reflected light from block 1020. In some examples, an ocular hydration sensor/reflectometer system controller may perform these measurements and/or more. Such an ocular hydration sensor/reflectometer system controller may be, for example, the ocular hydration sensor/reflectometer system controller 775 of FIG. 7; the ocular hydration sensor/reflectometer system controller 875A of FIG. 8A; the ocular hydration sensor/reflectometer system controller 875B of FIG. 8B; or the ocular hydration sensor/reflectometer system controller 975 of FIG. 9.

At block 1040, an eye tracking system of the near-eye display device may re-calibrate one or more parameters based on the measurements taken in block 1030 to optimize eye tracking performance. In some examples, the one or more parameters may be, for example, the intensity of illumination of the eye tracking projector and/or the exposure time of the eye tracking camera. In some examples, the ocular hydration sensor/reflectometer system controller determines the one or more re-calibration parameter values and sends them to the eye tracking system; in other examples, the ocular hydration sensor/reflectometer system controller merely provides the calculated measurements to the eye tracking system, which determines the one or more re-calibration parameter values itself.

Optionally, in block 1045 in some examples, the measurements from the ocular hydration sensor/reflectometer system may assist in determining whether to prompt the user of the near-eye display device to take some sort of remedial action regarding the hydration of the user's eyes. In some examples, the measurements from the ocular hydration sensor/reflectometer system may be combined with data from other health sensors to determine whether to prompt the user to take remedial action. In some examples, the ocular hydration sensor/reflectometer system may make this determination; in some examples, the eye tracking system may make this determination; in some examples, another pre-existing processing component disposed in the near-eye display device may make this determination; and/or in some examples, a dedicated health/welfare processing unit may make this determination.

Optionally, if the determination is YES in block 1045, the near-eye display device in block 1050 may prompt the user to take remedial action. In some examples, the prompted remedial action may be to blink and/or to take a break. Optionally, if the determination is NO in block 1045 or after block 1050 is performed, the near-eye display device in block 1060 may record the ocular hydration measurements and, optionally, other health and/or environmental data as part of a longer-term eye health monitoring system/functionality. In some examples, the ocular hydration sensor/reflectometer system may perform block 1060; in some examples, the eye tracking system may perform block 1060; in some examples, another pre-existing processing component disposed in the near-eye display device may perform block 1060; in some examples, the AI module 170 of FIG. 1 may perform block 1060; and/or in some examples, a dedicated health/welfare processing unit may perform block 1060.

In all examples according to the present disclosure, and as indicated by the arrows back from blocks 1040, 1045, 1050, and 1060 back to block 1010 in FIG. 10, the method 1000 may be continuously performed. In some examples, blocks 1010, 1020, 1025, 1030, 1040, 1045, 1050, and 1060 may be performed roughly/approximately simultaneously as well as continuously.

According to examples, an ocular hydration sensor/reflectometer system of a near-eye display device, as well as methods of manufacturing an ocular hydration sensor/reflectometer system of a near-eye display device, are described herein. According to examples, methods, systems, and apparatuses for an ocular hydration sensor/reflectometer system of a near-eye display device are also described herein. A non-transitory computer-readable storage medium may have an executable stored thereon, which when executed instructs a processor to perform the methods described herein.

In the foregoing description, various inventive examples are described, including devices, systems, methods, and the like. For the purposes of explanation, specific details are set forth in order to provide a thorough understanding of examples of the disclosure. However, it will be apparent that various examples may be practiced without these specific details. For example, devices, systems, structures, assemblies, methods, and other components may be shown as components in block diagram form in order not to obscure the examples in unnecessary detail. In other instances, well-known devices, processes, systems, structures, and techniques may be shown without necessary detail in order to avoid obscuring the examples.

The figures and description are not intended to be restrictive. The terms and expressions that have been employed in this disclosure are used as terms of description and not of limitation, and there is no intention in the use of such terms and expressions of excluding any equivalents of the features shown and described or portions thereof. The word "example" is used herein to mean "serving as an example, instance, or illustration." Any embodiment or design described herein as an "example" is not necessarily to be construed as preferred or advantageous over other embodiments or designs.

II. Adaptive Thermal Management Using Integrated Microthermoelectric Coolers (mTECS) and Artificial Intelligence (AI)

II.1

This portion of the present disclosure relates generally to thermal management of a near-eye display device, and more specifically, to providing adaptive thermal management for a near-eye display device using integrated thermoelectric coolers (mTECs) and artificial intelligence (AI).

II.2

Wearable display devices, such as virtual reality (VR), augmented reality (AR), and/or mixed reality (MR) glasses, may require increasingly complex and intricate lens assembly structures for display, as well as increasingly complex and intricate electronic structures for generating and providing virtual reality (VR), augmented reality (AR), and/or mixed reality (MR) content, etc., thereby complicating, inter alia, the manufacturing process. Moreover, the need for both electronics and optics to have a relatively small size and negligible weight for portability and user comfort, as well as the ability to operate in a wide variety of environments, produces a host of challenges and competing concerns, in areas such as, for example, the thermal management of the multitude of electronics in close proximity to the user's head.

II.3

Features of this portion of the present disclosure (II. Adaptive Thermal Mgmt using MTECs & AI) are illustrated by way of example and not limited in the following figures, in which like numerals indicate like elements. One skilled in the art will readily recognize from the following that alternative examples of the structures and methods illustrated in the figures can be employed without departing from the principles described herein.

FIG. 1 illustrates a block diagram of an artificial reality system environment including a near-eye display device, according to an example.

FIGS. 2A through 2C illustrate various views of a near-eye display device in the form of a head-mounted display (HMD) device, according to an example.

FIGS. 3A and 3B illustrate various views of a near-eye display device in the form of a pair of glasses, according to an example.

Figure 11:
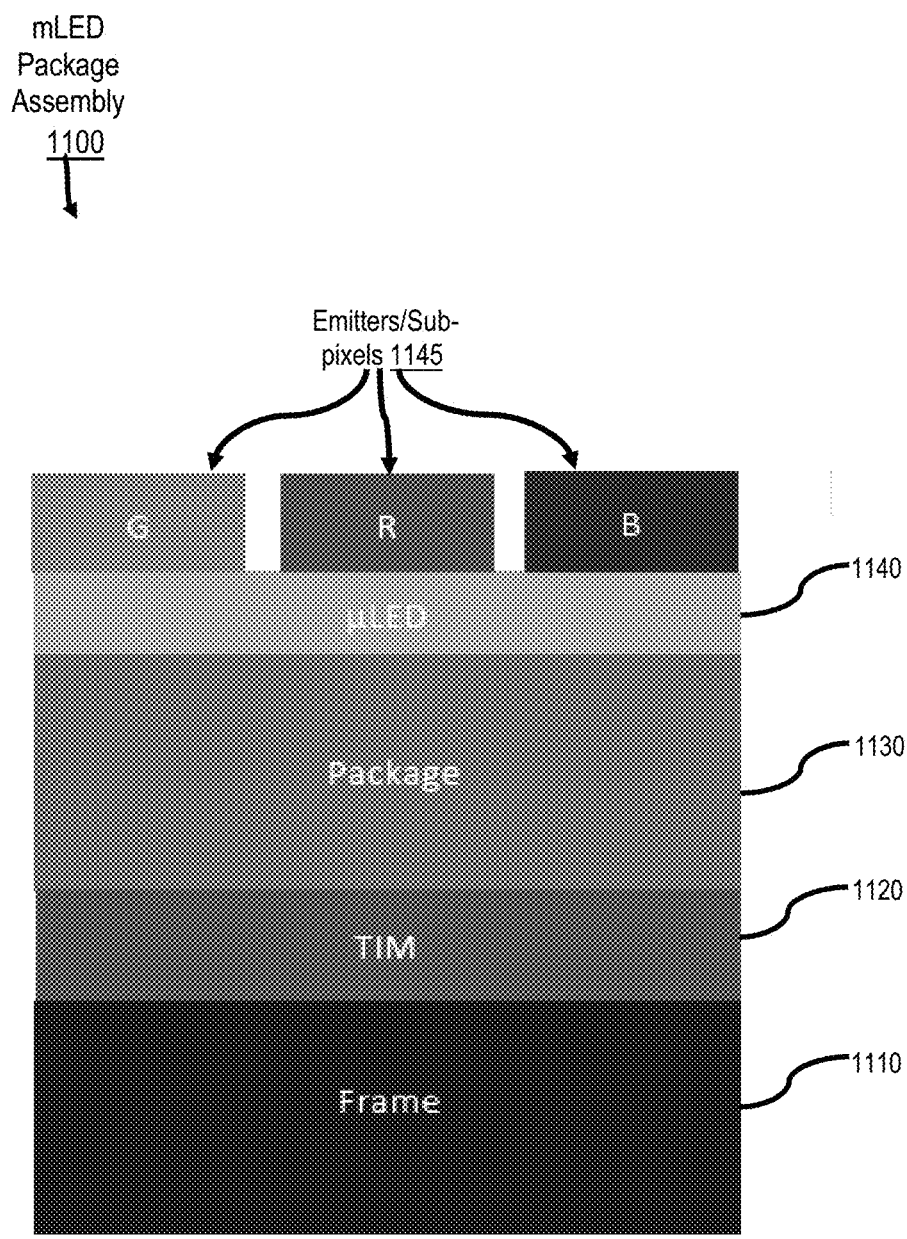

FIG. 11 illustrates a cross-section of a photonic integrated circuit (PIC)—specifically, a micro-light emitting diode (mLED)—in a near-eye display system, to which examples of this portion of this portion of the present disclosure (II. Adaptive Thermal Mgmt using MTECs & AI) may be applied.

Figure 12:
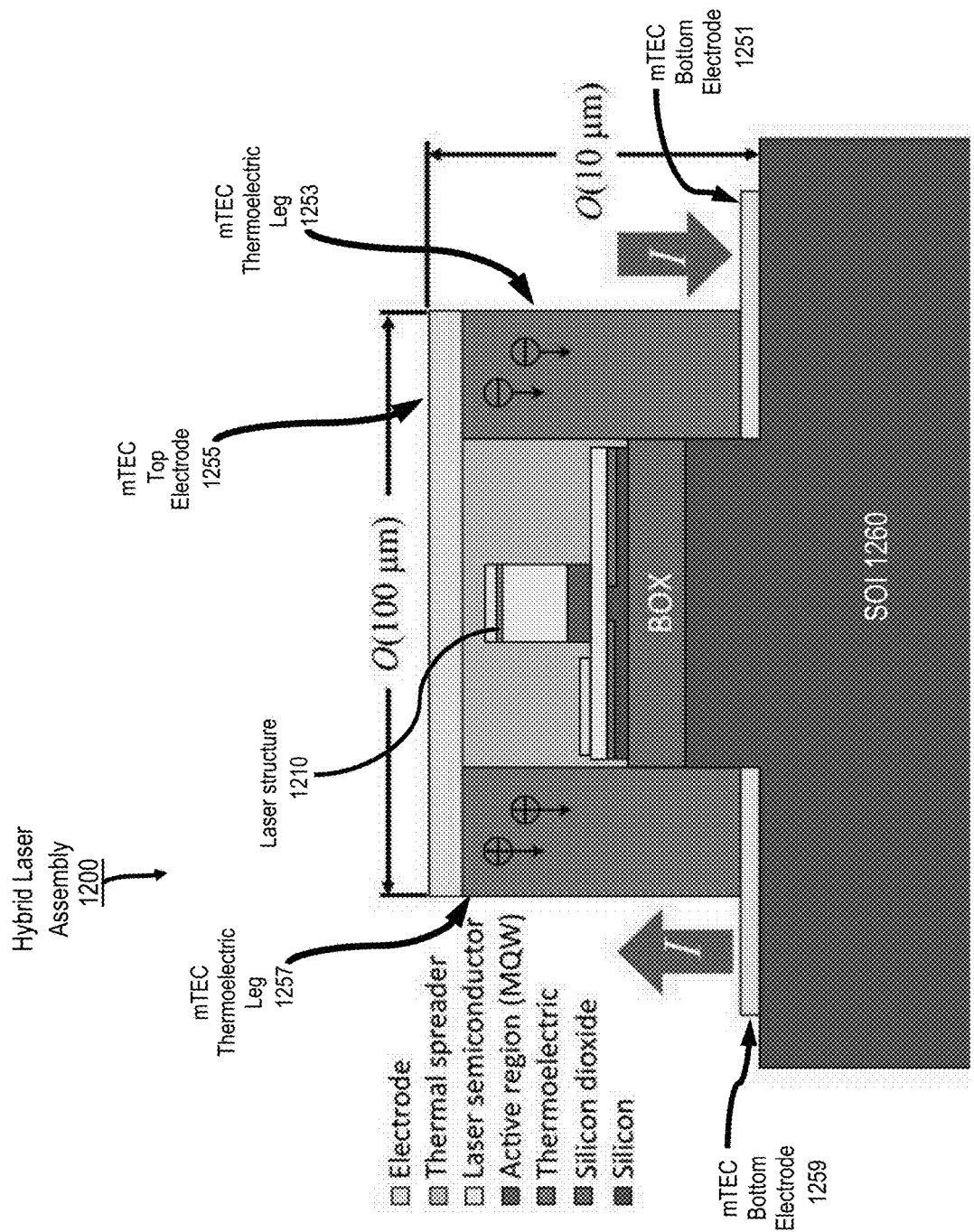

FIG. 12 illustrates a cross-section of a photonic integrated circuit (PIC)—specifically, a hybrid laser assembly-having an integrated micro-thermoelectric cooler (mTEC), in accordance with examples of this portion of the present disclosure (II. Adaptive Thermal Mgmt using MTECs & AI).

Figure 13:
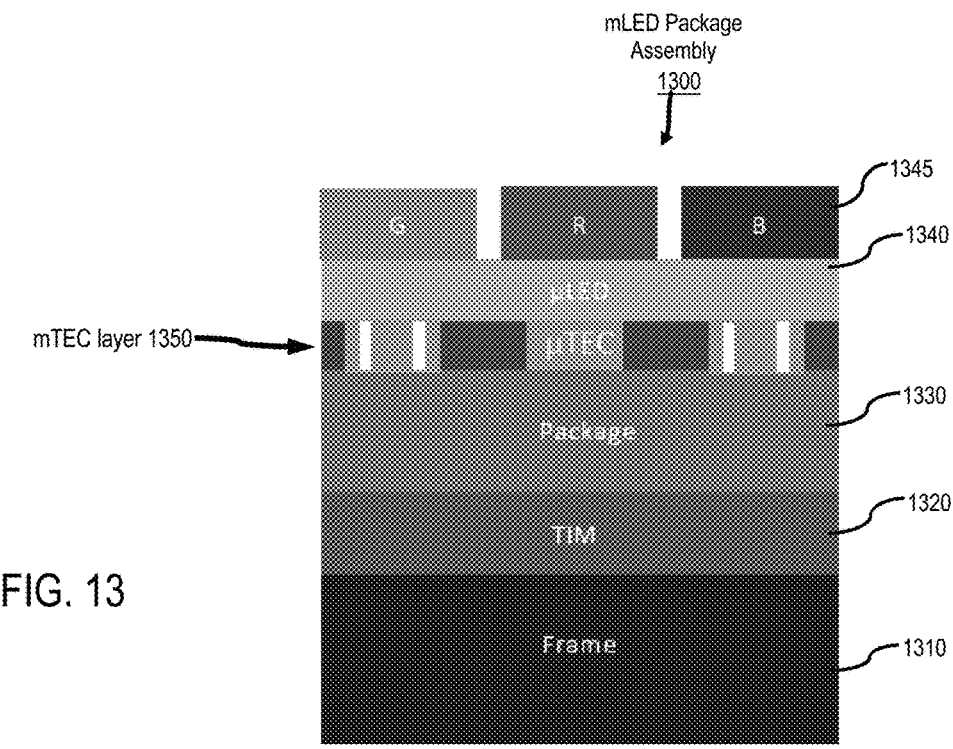

FIG. 13 illustrates a cross-section of a proposed architecture of a micro-light emitting diode (mLED) package assembly having an integrated micro-thermoelectric cooler (mTEC), according to an example of this portion of the present disclosure (II. Adaptive Thermal Mgmt using MTECs & AI).

Figure 14:
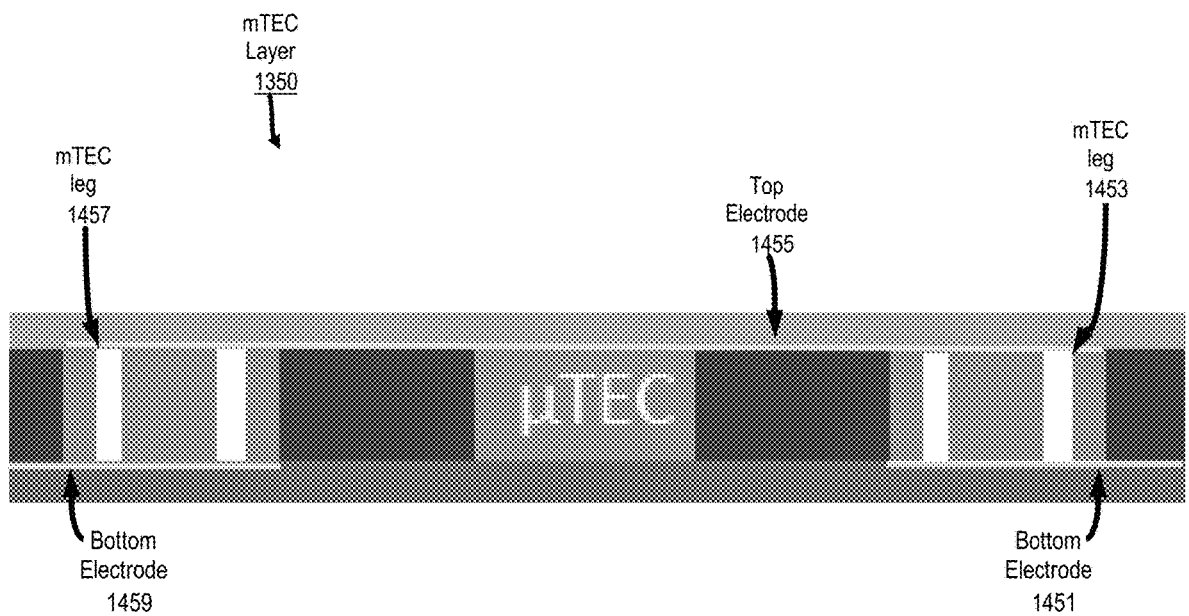

FIG. 14 illustrates a close-up of a cross-section of the integrated micro-thermoelectric cooler (mTEC) layer 1350 in FIG. 13, according to an example of this portion of the present disclosure (II. Adaptive Thermal Mgmt using MTECs & AI).

Figure 15:
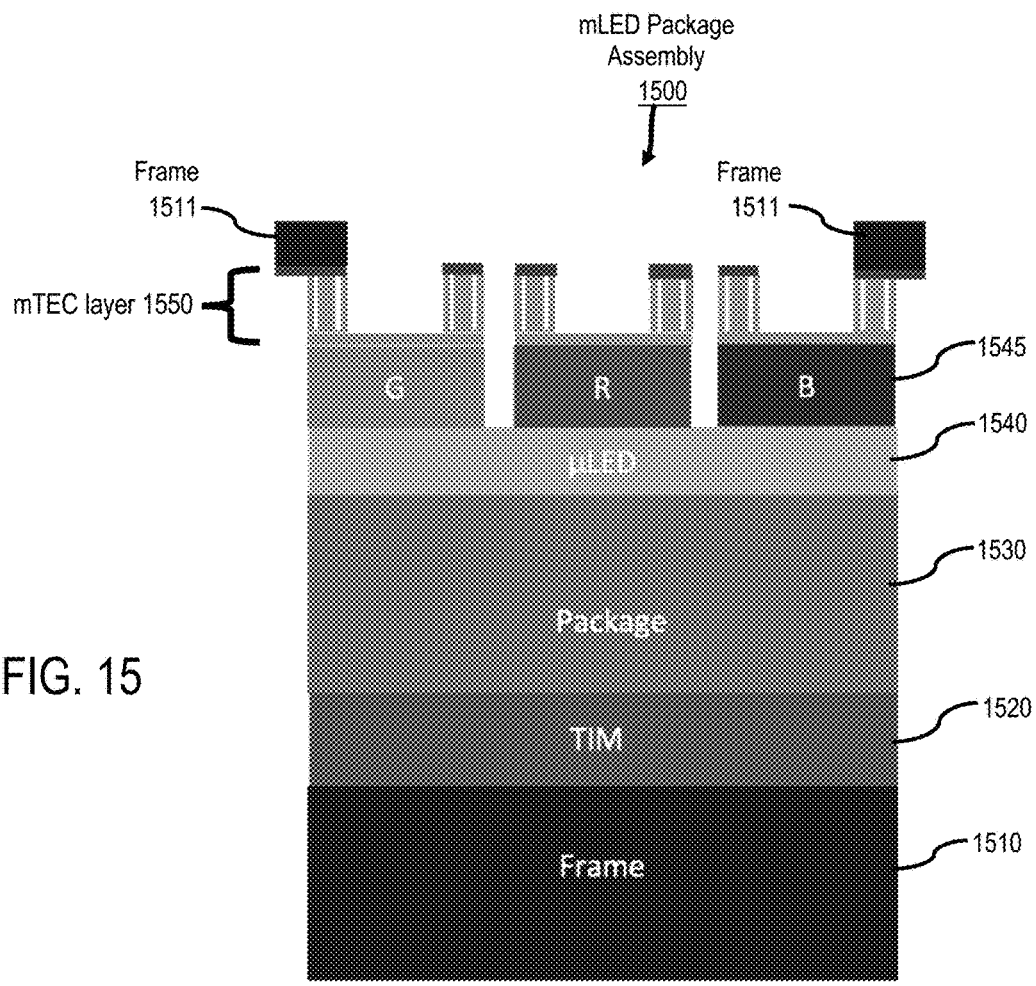

FIG. 15 illustrates a cross-section of an alternate proposed architecture of a micro-light emitting diode (mLED) package assembly having integrated micro-thermoelectric coolers (mTECs), according to an example of this portion of the present disclosure (II. Adaptive Thermal Mgmt using MTECs & AI).

Figure 16:
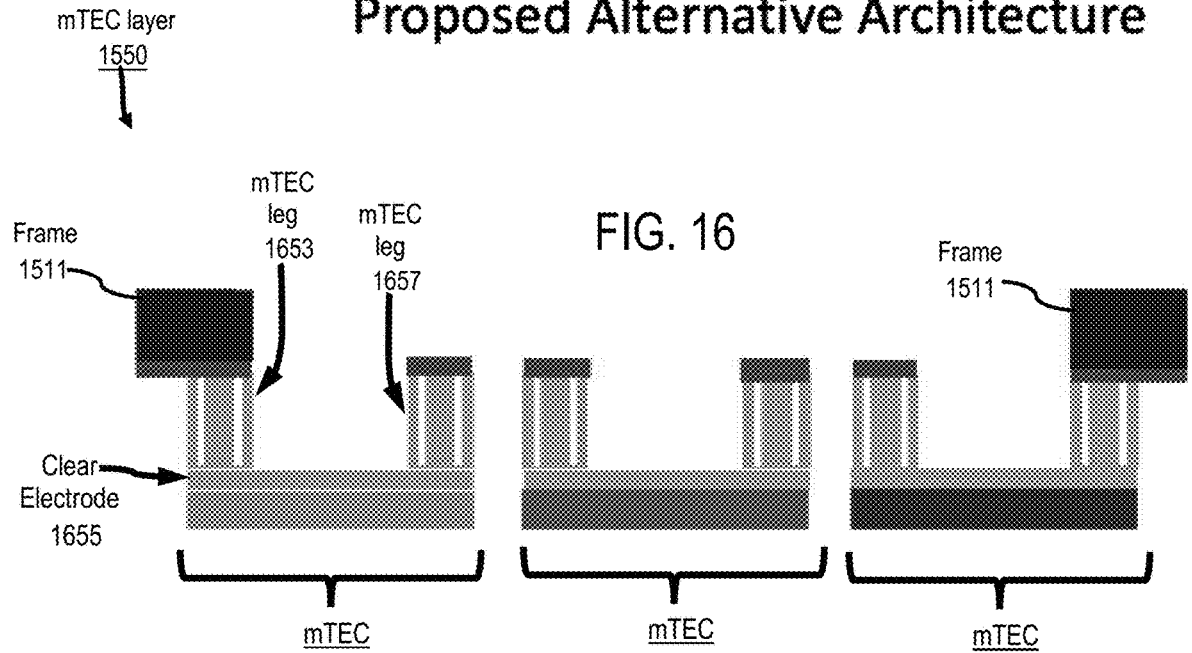

FIG. 16 illustrates a close-up of a cross-section of the integrated micro-thermoelectric cooler (mTEC) layer 1550 in FIG. 15, according to an example of this portion of the present disclosure (II. Adaptive Thermal Mgmt using MTECs & AI).

Figure 17:
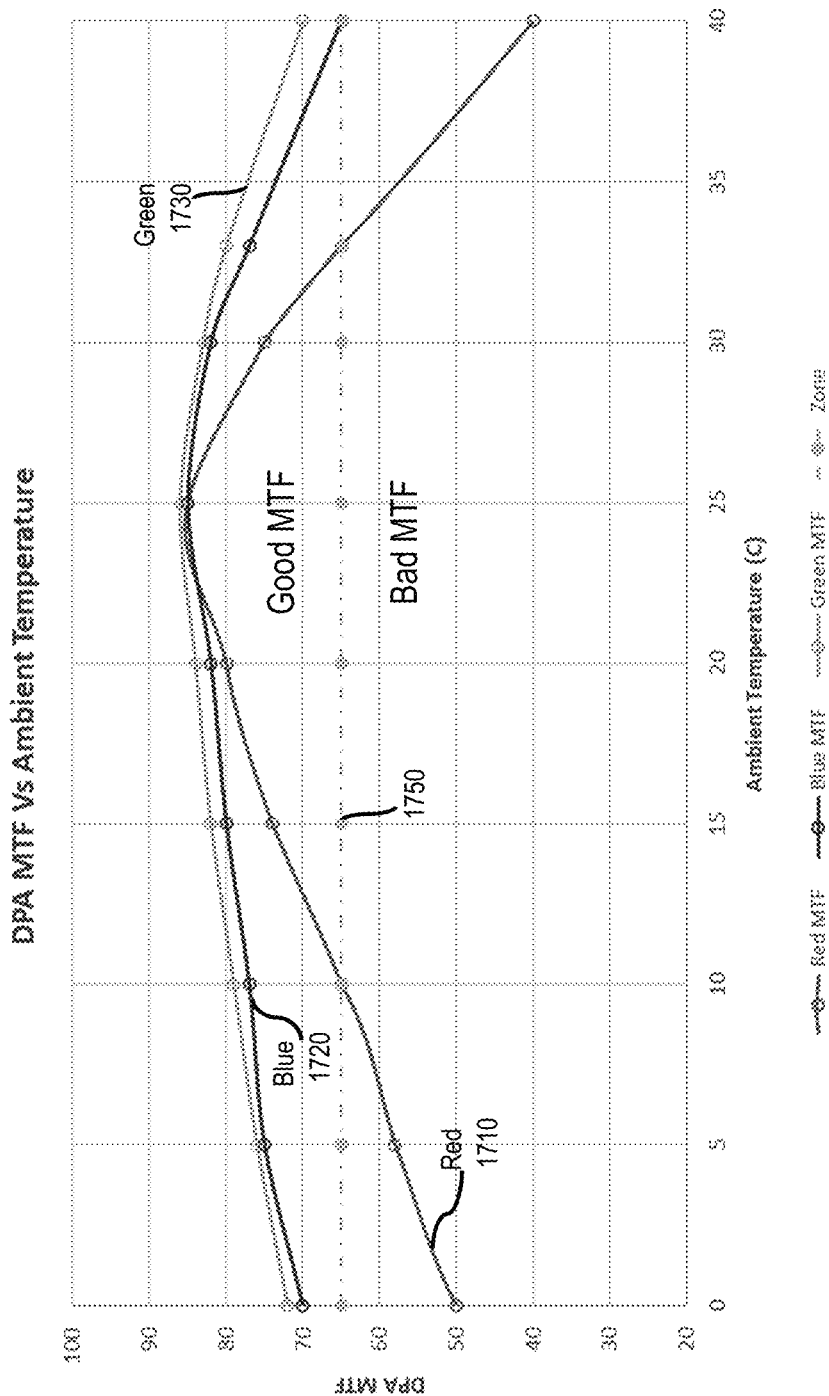

FIG. 17 is a graph of the modulation transfer function (MTF) of the emitters/sub-pixels of a light emitting diode (LED) vs. the ambient temperature (in Celsius), illustrating how certain temperature ranges may degrade the optical performance of the light emitting diode (LED), which may be mitigated by artificial intelligence (AI) and integrated micro-thermoelectric coolers (mTECs) according to examples of this portion of the present disclosure (II. Adaptive Thermal Mgmt using MTECs & AI).

Figures 18, 19:
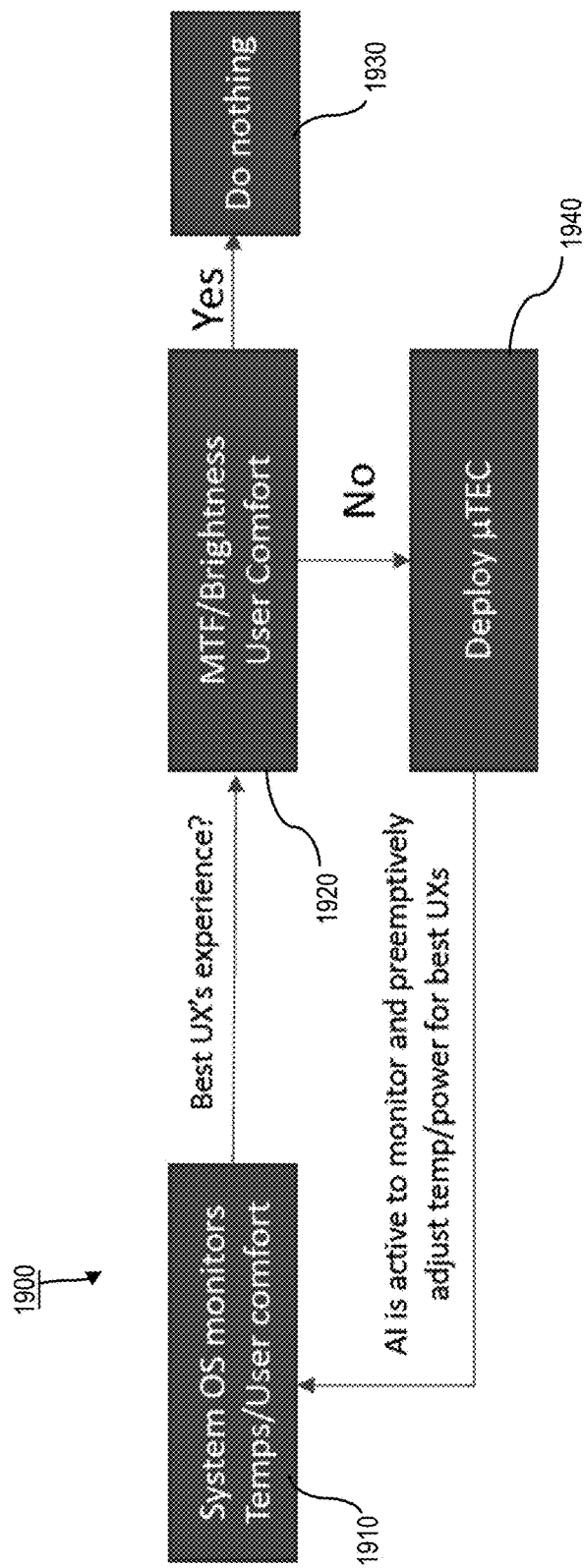

FIGS. 18 and 19 are a table and a flowchart, respectively, illustrating a method for monitoring and maintaining an optimal optical performance and/or user experience (UX) using artificial intelligence (AI) and integrated micro-thermoelectric coolers (mTECs) according to examples of this portion of the present disclosure (II. Adaptive Thermal Mgmt using MTECs & AI).

Figure 20:
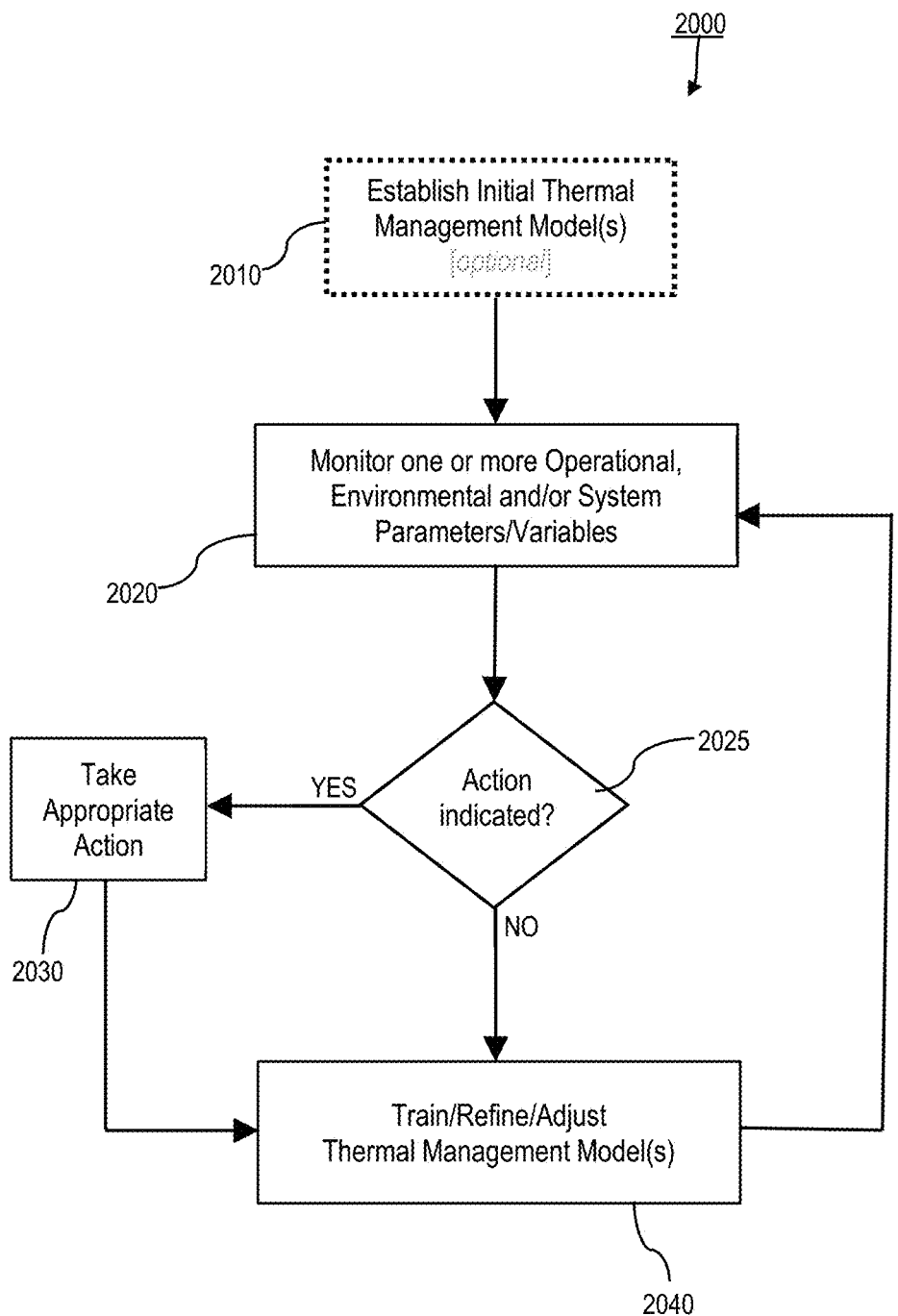

FIG. 20 is a flowchart illustrating a method for adaptive thermal management using artificial intelligence (AI) and integrated micro-thermoelectric coolers (mTECs) according to examples of this portion of the present disclosure (II. Adaptive Thermal Mgmt using MTECs & AI).

FIGS. 21 and 22 are flowcharts illustrating methods for manufacturing a heat source (e.g., a light source) with an integrated micro-thermoelectric cooler (mTEC) which may be used in a near-eye display device according to examples of this portion of the present disclosure (II. Adaptive Thermal Mgmt using MTECs & AI).

III.4.

Many components in a near-eye display device are sensitive to temperature changes. Accordingly, when a near-eye display device operates outside its optimal temperature range, its performance, in terms of, e.g., system/optical performance and user experience (UX), may degrade. Moreover, such temperature changes may also decrease the utility, and shorten the working life. of certain components of the near-eye display device. Many cooling solutions for near-eye display devices, such as, for example, mechanical solutions like, e.g., micro-fans, may be less than optimal because of, for example, their size (too large for the constrained form factor of a wearable device), the detrimental noise/vibrations they generate in the near-eye display device, the complications of adding such components during the manufacturing process, the increase in manufacturing costs of such cooling apparatuses, etc. Moreover, often a design and/or architecture of a near-eye display device may be optimized for operating either when hot or when cold, but not for both.

According to examples of this portion of the present disclosure (II. Adaptive Thermal Mgmt using MTECs & AI), methods, systems, and/or apparatuses for adaptive thermal management using one or more micro-thermoelectric coolers (mTECs) integrated into one or more heat sources of a near-eye display device are presented. In such examples, the integrated micro-thermoelectric coolers (mTECs) may be easily adapted into most fabrication processes (as discussed further below) and, since the integrated micro-thermoelectric coolers (mTECs) have no moving parts, the integrated micro-thermoelectric coolers (mTECs) may not generate any noise and/or vibration, unlike mechanical and other temperature-controlling mechanisms.

In some examples, an artificial intelligence (AI) may be employed to monitor one or more operational, environmental, and system parameters/variables (such as, e.g., temperature) and to control one or more components (such as, e.g., integrated micro-thermoelectric coolers (mTECs)) to provide the optimal system/optical performance and/or user experience (UX) for the near-eye display device based on the monitored parameters/variables. In some examples, the artificial intelligence (AI) may be incorporated into the operating system of the near-eye display device.

In some examples, one or more micro-thermoelectric coolers (mTECs) may be integrated into a light source, such as, e.g., a projector, of a near-eye display device. In some examples, one or more micro-thermoelectric coolers (mTECs) may be integrated into a micro-light emitting diode (mLED) package assembly, where the one or more micro-thermoelectric coolers (mTECs) may be disposed in a layer above the micro-light emitting diode (mLED) and/or in a layer below the micro-light emitting diode (mLED), or may be integrated into the micro-light emitting diode (mLED) itself.

According to examples of this portion of the present disclosure (II. Adaptive Thermal Mgmt using MTECs & AI), methods, systems, and/or apparatuses for manufacturing one or more micro-thermoelectric coolers (mTECs) integrated into one or more heat sources of a near-eye display device are presented. In some examples, the one or more integrated micro-thermoelectric coolers (mTECs) may be manufactured as part of a micro-light emitting diode (mLED) package assembly using electrodeposition in a complementary metal-oxide-semiconductor (CMOS) fabrication process.

While some advantages and benefits of this portion of the present disclosure (II. Adaptive Thermal Mgmt. using MTECs & AI) are discussed herein, there are additional benefits and advantages which would be apparent to one of ordinary skill in the art.

All of the previous paragraphs, including the descriptions of FIGS. 1, 2A-2C, and 3C, are incorporated in this portion of the present disclosure (II. Adaptive Thermal Mgmt. using MTECs & AI) in their entirety.

In some examples, the artificial intelligence (AI) module 170, which may be employed for controlling integrated micro-thermoelectric coolers (mTECs) according to this portion of the present disclosure (II. Adaptive Thermal Mgmt. using MTECs & AI), may be implemented, in whole or in part, as a separate physical component in the near-eye display device 120 (as shown in FIG. 1), the input/output interface 140, and/or the console 110, and/or integrated into any other suitable processing-capable and/or storage-capable components used for other functionality in the near-eye display device 120, the input/output interface 140, and/or the console 110 (such as, for example, the eye-tracking unit 130, the eye-tracking module 118, the headset tracking module 114, the virtual reality engine 116, the application store 112, and/or the wireless communication subsystem 134). In some examples, the artificial intelligence (AI) module 170 may be implemented/integrated, in whole or in part, into the operating system of the near-eye display device 120, or the overall artificial reality system environment 100.

In some examples, the artificial intelligence (AI) module 170 may receive input, store and process data, and/or control the integrated micro-thermoelectric coolers (mTECs) in accordance with received input and/or stored/processed data in order to maintain optimal operating conditions of one or more components in the near-eye display device 120. In some examples, the artificial intelligence (AI) module 170 may receive, store, and process temperature data, and control the integrated micro-thermoelectric coolers (mTECs) in accordance with the received, stored, and/or processed temperature data in order to maintain an optimal operating temperature of one or more light sources in the near-eye display device 120, such as, for example, the one or more projectors in the display electronics 122. Examples of the artificial intelligence (AI) module 170 in accordance with this portion of the present disclosure (II. Adaptive Thermal Mgmt. using MTECs & AI) are described in detail further below.

In various examples according to this portion of the present disclosure (II. Adaptive Thermal Mgmt using MTECs & AI), the waveguide 315 may be geometric, reflective, refractive, polarized, diffractive, and/or holographic, as would be understood of one of ordinary skill in the art, and may use any one or more of macro optics (such as, e.g., traditional optics, freeform prisms, and geometrical waveguide techniques, which may be based on Snell's law of reflection and refraction), micro optics (such as, e.g., diffractive grating techniques), and/or nano optics (such as, e.g., metalenses and/or metasurfaces, which may be based on the phase modulation effects of nanoscale structures).

Generally speaking, a diffractive waveguide system may comprise a light source, such as the projector 330, and a planar waveguide element that integrates an in-coupling diffractive grating and an out-coupling diffractive grating, such as the waveguide 315, as well as optics for projecting both the virtual image and the "see-through" real world scene to the user's eye, such as optics 350. In such examples, the waveguide 315 may use the in-coupling diffractive grating to receive the light projected by the projector 330, and the received light may propagate through the waveguide 315, bouncing between the inner surfaces of the waveguide 315 via total internal reflection (TIR), before exiting through the out-coupling diffractive grating and being projected into the user's eye through the optics 350. In some examples, the diffractive gratings may have a periodic structural form and may be, for example, surface relief gratings (SRG), volume hologram gratings (VHG), and/or polarization volume gratings (PVG). In various examples of this portion of the present disclosure (II. Adaptive Thermal Mgmt using MTECs & AI), the projector 330, the waveguide 315, and/or the optics 350 may be integrated, in whole or in part, into a single module or assembly.

In some examples, the waveguide 315 may be comprised of two parallel transparent/semi-transparent elements between which a liquid crystal forms a thin film. In some examples, the liquid crystal may be a nematic liquid crystal, a cholesteric liquid crystal, or any liquid crystal capable of manipulation by the application of an electric field, as would be understood by one of skill in the art. In some examples, light sources/emitters may be positioned adjacent to the liquid crystal such that their light is refracted through the liquid crystal medium, to which an electric field is applied by a thin film of electrically conductive and semi-transparent material to manipulate the liquid crystal and thusly the light being projected therethrough. In other examples, at least one transparent layer in the waveguide 315 may be formed of optical polymers, plastic, glass, transparent wafers (e.g., silicon carbide (SiC) wafers), amorphous silicon, silicon oxide ($SiO_2$), silicon nitride (SiN), titanium oxide (TiO), and/or any other transparent materials used for such a purpose, as would be understood by one of ordinary skill in the art.

In some examples, the projector 330 may include any suitable light source configured to generate a coherent or partially coherent light, such as, e.g., a laser diode, a vertical cavity surface emitting laser (VCSEL), a light emitting diode (LED), or any combination thereof. In some examples, the light source may be a panel, such as a liquid crystal display (LCD) panel, a liquid-crystal-on-silicon (LCoS) display panel, an organic light-emitting diode (OLED) display panel, a micro light-emitting diode (micro-LED) display panel, a digital light processing (DLP) display panel, a laser scanning display panel, or any combination thereof. In some embodiments, the light source may include a self-emissive panel and/or an external source. In some examples, the projector 330 may include one or more micro-light emitting diodes (mLEDs).

In some examples, the optics 350 may be formed of optical polymers, plastic, glass, transparent wafers (e.g., silicon carbide (SiC) wafers), amorphous silicon, silicon oxide ($SiO_2$), silicon nitride (SiN), titanium oxide (TiO), optical nylon, carbon-polymers, and/or any other suitably optically transparent materials used for such a purpose, as would be understood by one of ordinary skill in the art. In some examples, the optics 350, alone or in combination with other components (e.g., the waveguide 315 and/or the projector 330) may operate and/or be constructed similarly to the display optics 124 in FIG. 1 and/or the display optics discussed in reference to FIGS. 2A-2C.

In a near-eye display device, such as, e.g., the near-eye display device 300 in the form of a pair of glasses in FIGS. 3A-3B, the near-eye display device in the form of a head-mounted display (HMD) device 200 in FIGS. 2A-2C, and/or the near-eye display device 120 which is part of the artificial reality system 100 in FIG. 1, the user experience (UX) in terms of, for example, comfort (e.g., the sensation of heat), optical performance, brightness, etc., may be greatly affected by temperatures and/or changes in temperature. For instance, the optical performance of a near-eye display device may decrease when the optical system is operating outside the optimal ranges of certain parameters, such as, e.g., the temperatures of certain components. In such examples, the degradation in optical performance may be due to, for example, a mismatch in the coefficients of thermal expansion (CTEs) of the various different materials making up the optical system.

According to examples of this portion of the present disclosure (II. Adaptive Thermal Mgmt using MTECs & AI), both micro-thermoelectric cooler(s) (mTEC) and artificial intelligence (AI) may be employed to control and manage the thermal environment of one, more, or all suitable/applicable electrical, optical, and/or mechanical components in a near-eye display device. In some examples, one or more micro-thermoelectric cooler(s) (mTEC) may be integrated into one or more photonic integrated circuits (PICs), such as a liquid crystal display (LCD) and/or a light-emitting diode (LED). In some examples, one or more micro-thermoelectric cooler(s) (mTEC) may be integrated into a projector, such as the one or more projectors described in reference to the display electronics 122 of the near-eye display device 120 in FIG. 1, the one or more projectors described in reference to the display electronics and/or the display 210 of the head-mounted display (HMD) device 200 in FIGS. 2A-2C, and/or the projector 330 of the near-eye display device 300 in FIGS. 3A-3B. In some examples, the one or more projectors may include a micro-light emitting diode (mLED) and/or a display panel of micro-light emitting diodes (mLEDs). In some examples, the one or more projectors may include, e.g., a laser diode, a vertical cavity surface emitting laser (VCSEL), a conventional light emitting diode (LED) (such as, e.g., an organic light-emitting diode (OLED)), and/or any combination thereof; or a panel, such as a liquid crystal display (LCD) panel, a liquid-crystal-on-silicon (LCoS) display panel, an organic light-emitting diode (OLED) display panel, a digital light processing (DLP) display panel, a laser scanning display panel, or any combination thereof.

FIG. 11 illustrates a cross-section of a photonic integrated circuit (PIC)—specifically, a micro-light emitting diode (mLED)—in a near-eye display system, to which examples of this portion of the present disclosure (II. Adaptive Thermal Mgmt using MTECs & AI) may be applied. The specific micro-light emitting diode (mLED) package assembly 1100 shown in FIG. 11 is provided by way of example and illustration, and thus omits aspects, features, and/or components not germane to examples of this portion of the present disclosure (II. Adaptive Thermal Mgmt using MTECs & AI), as would be understood by one of ordinary skill in the art. Accordingly, the specific micro-light emitting diode (mLED) package assembly 1100 shown in FIG. 11 is thus not limiting in any way to where and how examples of this portion of the present disclosure (II. Adaptive Thermal Mgmt using MTECs & AI) may be applied to a near-eye display device, as would be understood by one of ordinary skill in the art. The micro-light emitting diode (mLED) package assembly 1100 shown in FIG. 11 may be disposed in any type or form of near-eye display device, such as, e.g., the near-eye display device 300 in the form of a pair of glasses in FIGS. 3A-3B, the head-mounted display (HMD) device 200 in FIGS. 2A-2C, and/or the near-eye display device 120 which is part of the artificial reality system 100 in FIG. 1.

The micro-light emitting diode (mLED) package assembly 1100 shown in FIG. 11 may or may not be part of a projector or display system, such as the one or more projectors described in reference to the display electronics 122 of the near-eye display device 120 in FIG. 1, the one or more projectors described in reference to the display electronics and/or the display 210 of the head-mounted display (HMD) device 200 in FIGS. 2A-2C, and/or the projector 330 of the near-eye display device 300 in FIGS. 3A-3B. As shown in FIG. 11, the micro-light emitting diode (mLED) package assembly 1100 may be disposed on a frame 1110, such as, e.g., a portion of the frame or body 220 of the head-mounted display (HMD) device 200 in FIGS. 2A-2C and/or the frame 305 of the near-eye display device 300 in the form of a pair of glasses in FIGS. 3A-3B.

In some examples, a thermal interface material (TIM) 1120 may be disposed upon the frame 1110 and further, a package 1130 may be disposed on the thermal interface material (TIM) 1120. As would be understood by one of ordinary skill in the art, the thermal interface material (TIM) 1120 may be one or more metals (such as, an indium alloy, sintered silver, metal oxides, etc.), polymers, phase-change materials (PCMs), thermal tapes/adhesives/glues, silicone or a silicone-like material, curing materials, carbon black, carbon nanotubes, etc. As would be understood by one of ordinary skill in the art, the package 1120 may include a substrate, such as a silicon-on-insulator (SOI) substrate, and a single crystal or polycrystalline silicon and/or another suitable semiconductor (e.g., germanium). In some examples, the package 1120 may be for a micro-light emitting diode (mLED) 1140, which may, in turn, have green (G), red (R), and blue (B) emitters/sub-pixels 1145.

In some examples, an active light emitting area of the micro-light emitting diode (mLED) package assembly 1100 may have a wide variety of sizes, including, e.g., less than 2,000 square micrometers, less than 20 square micrometers, less than 10 square micrometers, and/or less than 2 square micrometers, as would be understood by one of ordinary skill in the art. In some examples, any suitable deposition process may be used to fabricate layers (including, e.g., the emitters/sub-pixels 1145, the micro-light emitting diode (mLED) 1140, and/or some, part, or all of the package 1130) of the micro-light emitting diode (mLED) package assembly 1100, such as, for example, physical vapor deposition (PVD), chemical vapor deposition (CVD), evaporation, spray-coating, spin-coating, atomic layer deposition (ALD), and the like. In some examples, the micro-light emitting diode (mLED) package assembly 1100 may be manufactured using a thermal evaporator, a sputtering system, printing, stamping, etc., as would be understood by one of ordinary skill in the art.

In an architecture like the micro-light emitting diode (mLED) package assembly 1100 shown in FIG. 11, optical/electronic/mechanical performance may typically be optimized for heat or cold, but not both. Accordingly, system performance may be necessarily reduced for some environments, situations, and/or temperature ranges, thereby negatively impacting the user experience (UX). For instance, the optical performance of a near-eye display device having the micro-light emitting diode (mLED) package assembly 1100 shown in FIG. 11 may decrease when the micro-light emitting diode (mLED) package assembly 1100 is operating outside its optimal range. In such examples, the degradation in optical performance may be due to, for example, a mismatch in the coefficients of thermal expansion (CTEs) of the various materials making up the optical system, e.g., the different materials comprising the thermal interface material (TIM) 1120, the package 1130, and/or the micro-light emitting diode (mLED) 1140 with its green (G), red (R), and blue (B) emitters 1145.

According to examples of this portion of the present disclosure (II. Adaptive Thermal Mgmt using MTECs & AI), both an integrated micro-thermoelectric cooler(s) (mTEC) and artificial intelligence (AI) may be employed to control and manage the thermal environment of one, more, or all suitable/applicable electrical, optical, and/or mechanical components in a near-eye display device, such as, for example and without limitation, the micro-light emitting diode (mLED) package assembly 1100 shown in FIG. 11. An integrated micro-thermoelectric cooler (mTEC) is described below in reference to FIG. 12.

FIG. 12 illustrates a cross-section of a photonic integrated circuit (PIC)—specifically, a hybrid laser assembly-having an integrated micro-thermoelectric cooler (mTEC), in accordance with examples of this portion of the present disclosure (II. Adaptive Thermal Mgmt using MTECs & AI). Specifically, a hybrid laser assembly 1200 suitable for optical telecommunications is shown in FIG. 12. Accordingly, the hybrid laser structure 1200 shown in FIG. 12 is provided by way of example and illustration, in order to best explain and demonstrate how a micro-thermoelectric cooler (mTEC) may be integrated into an optoelectronic device. As would be understood by one of ordinary skill in the art, FIG. 12 may not be to scale and may omit aspects, features, and/or components not germane to examples of this portion of the present disclosure (II. Adaptive Thermal Mgmt using MTECs & AI), and thus is not limiting in any way to where and how examples of this portion of the present disclosure (II. Adaptive Thermal Mgmt using MTECs & AI) may be applied to a near-eye display device, as would also be understood by one of ordinary skill in the art.

As shown in FIG. 12, a semiconductor laser may be encapsulated within an integrated micro-thermoelectric cooler (mTEC). More specifically, a laser structure 1210 may be encapsulated by a thermal spreader, i.e., aluminum nitride (AlN) 1220, and may be disposed on a buried oxide layer (BOX) 1230. A micro-thermoelectric cooler (mTEC) 1250 may further encapsulate the laser structure 1210, its surrounding thermal spreader aluminum nitride (AlN) 1220, and the buried oxide layer (BOX) 1230 and may be disposed on a same silicon-on-insulator (SOI) substrate 1260 as the laser structure 1210 and the buried oxide layer (BOX) 1230. In other examples, a polymer encapsulate other than aluminum nitride (AlN) may be used as a thermal spreader (such as, e.g., benzocyclobutene (BCB) based and/or related polymers).

As shown in FIG. 12, the micro-thermoelectric cooler (mTEC) 1250 may comprise, from right to left, a right bottom electrode 1251, a thermoelectric right leg 1253, a top electrode 1255, a thermoelectric left leg 1257, and a left bottom electrode 1259. In operation, a current (I) may flow on this same path, from right to left, through the micro-thermoelectric cooler (mTEC) 1250, as indicated by the arrows labelled "I." In some examples, the thermoelectric right leg 1253 may be an n-type semiconductor and the thermoelectric left leg 1257 may be a p-type semiconductor. Generally speaking, in operation, when a voltage is applied to the micro-thermoelectric cooler (mTEC) 1250, heat is absorbed at the top electrode 1255 and dissipated from the bottom, at the right and left bottom electrodes 1251 and 1259, respectively, due to the Peltier effect, thereby dissipating the heat of the laser structure 1210 into the silicon-on-insulator (SOI) substrate 1260. As would be understood by one of ordinary skill in the art, the directional terms "top" and "bottom" are used herein for the sake of convenience and ease of explanation, and are not intended to necessarily have any separate directional meaning regarding the construction of a micro-thermoelectric cooler (mTEC) according to examples of this portion of the present disclosure (II. Adaptive Thermal Mgmt using MTECs & AI).

In some examples, the micro-thermoelectric cooler (mTEC) 1250 may be integrated around a hybrid ridge waveguide, i.e., a direct band-gap III-V material wafer-bonded to the silicon-on-insulator (SOI) substrate 1260, where the legs 1253 and 1257 of the micro-thermoelectric cooler (mTEC) 1250 may be fabricated using electrodeposition. In some examples, the thermoelectric right leg 1253 may be formed by electrodeposition from n-type $Bi_2(Te_xSe_{1-x})_3$ and the thermoelectric left leg 1257 may be formed by electrodeposition from p-type $(Bi_{1-x}Sb_x)_2Te_3$. In other examples, other techniques may be used to form the micro-thermoelectric cooler (mTEC) 1250, as would be understood by one of ordinary skill in the art, such as, e.g., metal-organic chemical vapor deposition, ball milling, melt spinning, and spark plasma sintering. Though not reaching the same level of material thermoelectric performance, electrodeposition may be a compatible back-end process in complementary metal-oxide semiconductor (CMOS) fabrication and, moreover, may be a low-cost, room-temperature alternative to more cost-intensive, high-vacuum processes such as molecular beam epitaxy or thermal co-evaporation.

In some examples, the integrated micro-thermoelectric cooler (mTEC) 1250 may be formed in a back-end process by first etching through the buried oxide layer (BOX) 1230 of the silicon-on-insulator (SOI) substrate 1260 to a depth of around 10 micrometers on either side of the encapsulated waveguide wafer (with the laser structure 1210) bonded to the silicon-on-insulator (SOI) substrate 1260. The bottom hot contact junctions, i.e., the right and left bottom electrodes 1251 and 1259, may be formed, followed by the deposition of the n-type and p-type thermoelectric elements, i.e., the thermoelectric n-type right leg 1253 and the thermoelectric p-type left leg 1257. Finally, the top cold junction, i.e., the top electrode 1255, may be formed to complete the electrical circuit comprising the integrated micro-thermoelectric cooler (mTEC) 1250.

In some examples, the laser structure 1210 may comprise an active region of multiple quantum well (MQW) regions, laser semiconductors, and electrodes, as would be understood by one of ordinary skill in the art, while the laser structure 1210 may be encapsulated by a thermal spreader polymer (such as aluminum nitride (AlN) 1220) to facilitate improved thermal spreading from the heat generating lasing region to the cold junction, i.e., the top electrode 1255, of the integrated micro-thermoelectric cooler (mTEC) 1250. Surrounding the laser structure 1210 may be thermoelectric elements such as, e.g., the thermoelectric n-type right leg 1253 and the thermoelectric p-type left leg 1257, that extend below the buried oxide layer (BOX) 1230 of the silicon-on-insulator (SOI) substrate 1260 that may function as an optical cladding layer and to thermally isolate the laser structure 1210 from the hot junction (i.e., the right and left bottom electrodes 1251 and 1259) of the integrated micro-thermoelectric cooler (mTEC) 1250.

As indicated above, the hybrid laser assembly 1200 in FIG. 12 is intended for illustrative purposes only and is non-limiting. In some examples, one or more thermoelectric coolers (mTECs) are integrated into other heat sources disposed in a near-eye display device. In some examples, one or more thermoelectric coolers (mTECs) are integrated into light sources disposed in a near-eye display device.

FIG. 13 illustrates a cross-section of a proposed architecture of micro-light emitting diode (mLED) package assembly having an integrated micro-thermoelectric cooler (mTEC), according to an example of this portion of the present disclosure (II. Adaptive Thermal Mgmt using MTECs & AI). Similarly to the micro-light emitting diode (mLED) package assembly 1100 in FIG. 11, a micro-light emitting diode (mLED) package assembly 1300 shown in FIG. 13 may or may not be part of a projector or display system, such as the one or more projectors described in reference to the display electronics 122 of the near-eye display device 120 in FIG. 1, the one or more projectors described in reference to the display electronics and/or the display 210 of the head-mounted display (HMD) device 200 in FIGS. 2A-2C, and/or the projector 330 of the near-eye display device 300 in FIGS. 3A-3B. As shown in FIG. 13, the micro-light emitting diode (mLED) package assembly 1300 may include a frame 1310 (which may be a portion of, e.g., the frame or body 220 of the head-mounted display (HMD) device 200 in FIGS. 2A-2C and/or the frame 305 of the near-eye display device 300 in the form of a pair of glasses in FIGS. 3A-3B), a thermal interface material (TIM) 1320, a package 1330, and a micro-light emitting diode (mLED) 1340 having green (G), red (R), and blue (B) sub-pixels/emitters 1345, similar to the similarly named components in FIG. 11.

As shown in FIG. 13, an integrated micro-thermoelectric cooler (mTEC) layer 1350 may be formed in, and/or as part of, the package layer 1330 of the micro-light emitting diode (mLED) package assembly 1300, in the portion directly contiguous with the micro-light emitting diode (mLED) layer 1340 such that the heat created in the micro-light emitting diode (mLED) layer 1340 may be dissipated into the package layer 1330. This will be described in greater detail below, with reference to FIG. 14.

FIG. 14 illustrates a close-up of a cross-section of the integrated micro-thermoelectric cooler (mTEC) layer 1350 in FIG. 13, according to an example of this portion of the present disclosure (II. Adaptive Thermal Mgmt using MTECs & AI). As shown in FIG. 14, there may be an integrated micro-thermoelectric cooler (mTEC), which may have a bottom electrode 1451, an n-type semiconductor thermoelectric leg 1453, a top electrode 1455, a p-type semiconductor thermoelectric leg 1457, and a bottom electrode 1459. Although the example in FIG. 14 has the n-type semiconductor thermoelectric leg on the right-hand side of the integrated micro-thermoelectric coolers (mTECs) and the p-type semiconductor thermoelectric leg on the left-hand side in the integrated micro-thermoelectric coolers (mTECs), examples of this portion of the present disclosure (II. Adaptive Thermal Mgmt using MTECs & AI) are not so limited, and may be, for example, reversed in relative position. In some examples, there may be multiple integrated micro-thermoelectric coolers (mTECs) in the integrated micro-thermoelectric cooler (mTEC) layer 1350. As elsewhere, the directional terms "top" and "bottom" are used herein for the sake of convenience and ease of explanation, and are not intended to necessarily have any separate directional meaning regarding the construction of a micro-thermoelectric cooler (mTEC) according to examples of this portion of the present disclosure (II. Adaptive Thermal Mgmt using MTECs & AI).

As shown in FIG. 14, the top electrode 1455 may make an electrical connection between the tops of the n-type semiconductor thermoelectric leg 1453 and the p-type semiconductor thermoelectric leg 1457 and may be in physical contact with the micro-light emitting diode (mLED) 1340. Similarly, the bottom electrode 1451 may make an electrical connection with the bottom of the n-type semiconductor thermoelectric leg 1453 and may be in physical contact with the package 1330 and a bottom electrode 1459 may make an electrical connection with the bottom of the p-type semiconductor thermoelectric leg 1457 and may also be in physical contact with the package 1330. When an appropriate voltage is applied, a current flows through the bottom electrode 1451, the n-type semiconductor thermoelectric leg 1453, the top electrode 1455, the p-type semiconductor thermoelectric leg 1457, and the bottom electrode 1459. As discussed above, due to the Peltier effect, heat is absorbed at the top electrode 1455 and dissipated from the bottom electrodes 1451 and 1459, thereby dissipating the heat of the micro-light emitting diode (mLED) 1340 into the package 1330. If the current flow is reversed, the heat transfer may also be reversed, causing the top electrode 1455 to be the hot junction and the bottom electrodes 1451 and 1459 to be the cold junction.

In some examples, the n-type semiconductor thermoelectric leg 1453 may be formed by electrodeposition from n-type Biz $(Te_xSe_{1-x})_3$ and the p-type semiconductor thermoelectric leg 1457 may be formed by electrodeposition from p-type $(Bi_{1-x}Sb_x)_2Te_3$. In other examples, other techniques may be used to form the integrated micro-thermoelectric cooler (mTEC), as would be understood by one of ordinary skill in the art, such as, e.g., metal-organic chemical vapor deposition, ball milling, melt spinning, and spark plasma sintering. In some examples, electrodeposition may be employed as a compatible back-end process to complementary metal-oxide semiconductor (CMOS) fabrication. In some examples, the integrated micro-thermoelectric cooler (mTEC) may be formed in a back-end process by first etching through the substrate of the package 1330 and forming the bottom electrodes 1451 and 1459, which may be followed by the deposition of the n-type semiconductor thermoelectric leg 1453 and the p-type semiconductor thermoelectric leg 1457. Finally, the top electrode 1455 may be formed to complete the electrical circuit comprising the integrated micro-thermoelectric cooler (mTEC).

In some examples, a thermal spreader polymer, such as, e.g., aluminum nitride (AlN), may be employed to facilitate improved thermal spreading from the heat generating region to the cold junction, i.e., the top electrode 1455, of the integrated micro-thermoelectric cooler (mTEC). In some examples, the n-type semiconductor thermoelectric leg 1453 and the p-type semiconductor thermoelectric leg 1457 may extend further into the substrate of package 1330 and may function as an optical cladding layer to thermally isolate the micro-light emitting diode (mLED) 1340 from the hot junction, i.e., the bottom electrodes 1451 and 1459, of the integrated micro-thermoelectric cooler (mTEC).

Unlike mechanical solutions to temperature management, such as micro-fans and microfluidic hydraulics, examples according to this portion of the present disclosure (II. Adaptive Thermal Mgmt using MTECs & AI) have no moving parts and may not introduce any vibration and/or noise into the near-eye display device. Moreover, the relatively small size of the micro-thermoelectric cooler (mTEC) in examples of this portion of the present disclosure (II. Adaptive Thermal Mgmt using MTECs & AI) may be much easier to integrate into the constrained form factor of near-eye display devices and to include in the fabrication processes of components of near-eye display devices, thereby reducing costs, time, and overall complexity during manufacturing, and increasing the overall working life of the near-eye display device. Furthermore, thermal management systems in accordance with examples of this portion of the present disclosure (II. Adaptive Thermal Mgmt using MTECs & AI) may provide either cooling or heating using the same instrumentality by merely changing the direction of the current flow through the one or more micro-thermoelectric coolers (mTECs). By these means, thermal management systems using one or more micro-thermoelectric coolers (mTECs) in accordance with examples of this portion of the present disclosure (II. Adaptive Thermal Mgmt using MTECs & AI) may appropriately balance the temperature in various parts/components of a near-eye display device in order that a more optimal optical performance and/or a more optimal user experience (UX) may be provided.

In examples using complementary metal-oxide semiconductor (CMOS) fabrication, electrodeposition may be employed as a compatible back-end process, thereby providing a more low-cost, room-temperature alternative to more cost-intensive, high-vacuum processes such as, e.g., molecular beam epitaxy or thermal co-evaporation. Moreover, examples using complementary metal-oxide semiconductor (CMOS) fabrication may more easily integrate into existing fabrication processes.

In some examples, artificial intelligence (AI) may be employed with one or more micro-thermoelectric coolers (mTECs) in order to further optimize the overall system thermal, power, and optical performance, as discussed in further detail below. In such examples, various sensors may be employed by the artificial intelligence (AI) to further sense, analyze, and optimize the user experience (UX).

FIG. 15 illustrates a cross-section of an alternate proposed architecture of a micro-light emitting diode (mLED) package assembly having integrated micro-thermoelectric coolers (mTECs), according to an example of this portion of the present disclosure (II. Adaptive Thermal Mgmt using MTECs & AI). While the micro-thermoelectric cooler (mTEC) of FIGS. 13-14 may be integrated into the package layer, i.e., below the micro-light emitting diode (mLED), the micro-thermoelectric coolers (mTECs) of FIGS. 15-16 may be integrated above the micro-light emitting diode (mLED) in accordance with examples of this portion of the present disclosure (II. Adaptive Thermal Mgmt using MTECs & AI).

Similarly to the micro-light emitting diode (mLED) package assembly 1100 in FIG. 11 and the micro-light emitting diode (mLED) package assembly 1300 in FIG. 13, a micro-light emitting diode (mLED) package assembly 1500 shown in FIG. 15 may or may not be part of a projector or display system, such as the one or more projectors described in reference to the display electronics 122 of the near-eye display device 120 in FIG. 1, the one or more projectors described in reference to the display electronics and/or the display 210 of the head-mounted display (HMD) device 200 in FIGS. 2A-2C, and/or the projector 330 of the near-eye display device 300 in FIGS. 3A-3B. As shown in FIG. 15, the micro-light emitting diode (mLED) package assembly 1500 may include a frame 1510 (such as, e.g., a portion of the frame or body 220 of the head-mounted display (HMD) device 200 in FIGS. 2A-2C and/or the frame 305 of the near-eye display device 300 in the form of a pair of glasses in FIGS. 3A-3B), a thermal interface material (TIM) layer 1520, a package 1530, and a micro-light emitting diode (mLED) 1540 having green (G), red (R), and blue (B) sub-pixels/emitters 1545, similar to the similarly named components in FIGS. 11 and 13.

As shown in FIG. 15, an integrated micro-thermoelectric cooler (mTEC) layer 1550 may be formed on top of the micro-light emitting diode (mLED) package assembly 1500 as part of the frame 1511 of the near-eye display device. More specifically, micro-thermoelectric coolers (mTECs) of the integrated micro-thermoelectric cooler (mTEC) layer 1550 are disposed upon the sides of the top surfaces of the green (G), red (R), and blue (B) sub-pixels/emitters 1545 of the micro-light emitting diode (mLED) layer 1540 such that the heat created in the micro-light emitting diode (mLED) layer 1540 may be dissipated above and out from the micro-light emitting diode (mLED) package assembly 1500. Accordingly, the architecture of the integrated micro-thermoelectric coolers (mTECs) of FIG. 15 are upside-down versions of the integrated micro-thermoelectric cooler (mTEC) of FIG. 13 insofar as the cool junction may be formed as the bottom electrode and the hot junction may be formed as the top electrodes of the integrated micro-thermoelectric coolers (mTECs) in FIG. 15. This will be described in greater detail below, with reference to FIG. 16.

FIG. 16 illustrates a close-up of a cross-section of the integrated micro-thermoelectric cooler (mTEC) layer 1550 in FIG. 15, according to an example of this portion of the present disclosure (II. Adaptive Thermal Mgmt using MTECs & AI). As shown in FIG. 16, there are three separate micro-thermoelectric coolers (mTECs), one atop each of the green (G), red (R), and blue (B) sub-pixels/emitters 1545 of the micro-light emitting diode (mLED) layer 1540 from FIG. 15. As shown in FIG. 16, the right and left micro-thermoelectric coolers (mTECs) are attached to the frame 1511 of the near-eye display device, such as, e.g., the frame or body 220 of the head-mounted display (HMD) device 200 in FIGS. 2A-2C and/or the frame 305 of the near-eye display device 300 in the form of a pair of glasses in FIGS. 3A-3B.

As shown in FIG. 16, the left-hand integrated micro-thermoelectric cooler (mTEC) may include an n-type semiconductor thermoelectric leg 1653, a clear electrode 1655, and a p-type semiconductor thermoelectric leg 1657. The n-type semiconductor thermoelectric leg 1653 and the p-type semiconductor thermoelectric leg 1657 may be disposed on the edges of the sub-pixel/emitter of the micro-light emitting diode (mLED) so as to not block the emitted light. Similarly, the clear electrode 1655 connecting the n-type semiconductor thermoelectric leg 1653 and the p-type semiconductor thermoelectric leg 1657 may be disposed on and/or cover the surface of the sub-pixel/emitter of the micro-light emitting diode (mLED). In some examples, the clear electrode 1655 may be made of any suitable transparent or substantially transparent conductive materials, such as transparent conductive oxides (TCOs) like, e.g., indium tin oxide (ITO), zinc oxide (ZnO), and the like.

In the example shown in FIG. 16, a suitable material may be disposed between the frame 1511 and the n-type semiconductor thermoelectric leg 1653 and may function as a thermal spreader and/or insulator. Such a suitable material may have an electrode disposed within it which may be electrically connected to the top of the n-type semiconductor thermoelectric leg 1653. In some examples, when an appropriate voltage is applied, a current flows through this electrode, the n-type semiconductor thermoelectric leg 1653, the clear electrode 1655, and the p-type semiconductor thermoelectric leg 1657 into another electrode, which may also be disposed within a suitable material. As discussed above, due to the Peltier effect, heat is absorbed at the clear electrode 1655 on the bottom, attached to the surface of the sub-pixel/emitter, and dissipated from the electrodes located on the tops of the n-type semiconductor thermoelectric leg 1653 and the p-type semiconductor thermoelectric leg 1657, thereby dissipating the heat of the micro-light emitting diode (mLED) 1540 into the suitable thermal spreading/insulating material, the frame 1511, and/or the open air environment surrounding the near-eye display device. If the current flow is reversed, the heat transfer may also be reversed, causing the clear electrode 1655 to be the hot junction and the electrodes on the tops of the n-type semiconductor thermoelectric leg 1653 and the p-type semiconductor thermoelectric leg 1657 to be the cold junction.

In some examples, the electrode on the top of the p-type semiconductor thermoelectric leg 1657 may be electrically connected to an electrode of an n-type semiconductor thermoelectric leg on the neighboring integrated micro-thermoelectric cooler (mTEC), i.e., the middle micro-thermoelectric cooler (mTEC) in FIG. 16. Similarly, the electrode on the top of the p-type semiconductor thermoelectric leg of the middle micro-thermoelectric cooler (mTEC) may be electrically connected to an electrode of an n-type semiconductor thermoelectric leg on the neighboring integrated micro-thermoelectric cooler (mTEC), i.e., the right-hand micro-thermoelectric cooler (mTEC) in FIG. 16, thereby forming a complete single electrical path for controlling all three neighboring integrated micro-thermoelectric coolers (mTECs).

In some examples, the n-type semiconductor thermoelectric leg 1653 and the p-type semiconductor thermoelectric leg 1657 may be fabricated by electrodeposition as a compatible back-end process to complementary metal-oxide semiconductor (CMOS) fabrication, as discussed above. In some examples, any suitable deposition process may be used to fabricate various layers and/or portions of layers of the micro-light emitting diode (mLED) package assembly 1500, such as, for example, physical vapor deposition (PVD), chemical vapor deposition (CVD), evaporation, spray-coating, spin-coating, atomic layer deposition (ALD), and the like. In some examples, the micro-light emitting diode (mLED) package assembly 1500 may be manufactured using a thermal evaporator, a sputtering system, printing, stamping, etc., as would be understood by one of ordinary skill in the art.

As would be appreciated by one of ordinary skill in the art, although specific architectures, constructions, fabrication techniques, relative positioning of components, etc., are shown and described in reference to the examples shown in FIGS. 13-14 and 15-16, examples of this portion of the present disclosure (II. Adaptive Thermal Mgmt using MTECs & AI) are not so limited and other architectures, constructions, fabrication techniques, relative positioning of components, etc., may be used.

The one or more micro-thermoelectric coolers (mTECs) integrated into a near-eye display device in accordance with examples of this portion of the present disclosure (II. Adaptive Thermal Mgmt using MTECs & AI) may be controlled using technologies/techniques variously known as artificial intelligence (AI), deep learning, big data, machine learning, etc. As would be understood by one of ordinary skill in the art, generally speaking, such technologies/techniques may involve learning or training, in which a computing apparatus may use one or more models, which may be given to and/or generated by the computing apparatus, and one or more data sets, which may be given to and/or generated by the computing apparatus, in order to analyze and provide output regarding present data input. In some examples, the computing apparatus may be given one or more initial data sets and/or models. In some examples, training may be an adaptive and ongoing learning process, where presently input data is used to continually refine the one or more models.

Accordingly, "artificial intelligence" or "AI" as used herein may be understood as any type of machine learning, including, but not limited to, at least one of a neural network (such as, e.g., a convolutional neural network (CNN), a recurrent neural network (RNN), a dynamic neural network, a feed forward neural network, a radial basis function neural network, a modular neural network, a Kohonen self-organizing neural network, a long-/short-term memory neural network, an artificial neural network, etc.), a support-vector machine (SVM) or network, decision tree learning, regression analysis, a Bayesian network, a Gaussian process, a genetic algorithm, a (deep) reinforcement system, a (deep) belief system, a predictive analytics system, and/or the like, as would be understood by one of ordinary skill in the art.

In some examples, the artificial intelligence (AI), such as the artificial intelligence (AI) module 170 in FIG. 1, may be implemented by hardware, software, and/or any combination thereof (referred to as the "computing apparatus" above). In some examples, the artificial intelligence (AI) may be implemented by at least one of any type of application, program, library, script, task, service, process, or any type or form of executable instructions executed on hardware such as circuitry that may include digital and/or analog elements (e.g., one or more transistors, logic gates, registers, memory devices, resistive elements, conductive elements, capacitive elements, and/or the like, as would be understood by one of ordinary skill in the art). In some examples, the hardware and data processing components used to implement the various processes, operations, logic, and circuitry described in connection with the examples described herein may be implemented with a general purpose single- and/or multi-chip processor, a single- and/or multi-core processor, a digital signal processor (DSP), an application specific integrated circuit (ASIC), a field programmable gate array (FPGA), or other programmable logic device, discrete gate or transistor logic, discrete hardware components, and/or any combination thereof suitable to perform the functions described herein. A general purpose processor may be any conventional processor, microprocessor, controller, microcontroller, and/or state machine. In some examples, the memory/storage may include one or more components (e.g., random access memory (RAM), read-only memory (ROM), flash or solid state memory, hard disk storage, etc.) for storing data and/or computer-executable instructions for completing and/or facilitating the processing and storage functions described herein. In some examples, the memory/storage may be volatile and/or non-volatile memory, and may include database components, object code components, script components, or any other type of information structure suitable for implementing the various activities and storage functions described herein.

Hereinbelow, for the sake of convenience and ease of explanation, the description/discussion of artificial intelligence (AI) may refer to the artificial intelligence (AI) module 170 in FIG. 1; however, the artificial intelligence (AI) according to examples of this portion of the present disclosure (II. Adaptive Thermal Mgmt using MTECs & AI) is not limited in any way to the components, apparatuses, and/or constructions shown and/or described in reference to any of Figures described herein. In some examples, the components for implementing the artificial intelligence (AI) module 170 may be located, in whole or in part, in the near-eye display device and/or externally to the near-eye display device (such as, for example, in the input/output interface 140 and/or the console 110 in FIG. 1). In some examples, the artificial intelligence (AI) may be implemented/integrated, in whole or in part, in the operating system of the near-eye display device.

In some examples, the components for implementing the artificial intelligence (AI) module 170 may be, in whole or in part, the same components for implementing any of the other functions/operations of the near-eye display device, such as, for example, eye-tracking unit 130 or module 118, the headset tracking module 114, the virtual reality engine 116, the application store 112, the input/output interface 140, the wireless communication subsystem 134, the sensing operations/functionality, the image projecting operations/functionality, etc., described herein in reference to FIGS. 1, 2A-2C, and 3A-3B). In some examples, the components for implementing the artificial intelligence (AI) module 170 may be, in whole or in part, separate, functionally and/or physically, from the components for implementing any of the other functions/operations of the near-eye display device. In some examples, the processing and/or storage functionality of the artificial intelligence (AI) module 170 may be implemented as a separate component, such as, for example, a hardware memory/storage for the one or more models and one or more data sets.

In some examples, the data used by the artificial intelligence (AI) module 170 (such as, for example, data concerning the local environmental conditions) may be, in whole or in part, input from any of the same components providing input for any of the other functions/operations of the near-eye display device, such as, for example, the one or more temperature sensor(s) 136, the eye-tracking unit 130, the position sensor(s) 128, the locator(s) 126, the inertial measurement unit (IMU) 132, the wireless communication subsystem 134, the input/output interface 140, the external imaging device 150, etc., described herein in reference to FIGS. 1, 2A-2C, and 3A-3B and/or components not specifically described in detail herein in reference to FIGS. 1, 2A-2C, and 3A-3B, such as, e.g., a global positioning system (GPS) sensor/receiver, a camera facing the user and/or the external environment, a depth sensor, a motion sensor, an image sensor, a light sensor, etc., as would be understood by one of ordinary skill in the art.

In some examples, the artificial intelligence (AI) module 170 may store and/or continually update a data set involving temperatures of the user, the near-eye display device, and/or the external environment. In some examples, the data set may include temperature data related to the operating of the near-eye display device. In some examples, the temperature data set may be continually updated by the one or more temperature sensor(s) 136, which may be located in one or more positions in the near-eye display device suitable for determining the temperature of the display electronics 122. In some examples, the temperature data set may be related to the temperatures of the micro-light emitting diode (mLED) package assemblies 1300 and 1500 having the integrated micro-thermoelectric coolers (mTECs) shown and described in reference to FIGS. 13-14 and 15-16, respectively (which may be implemented/included in, for example, the one or more projectors described in reference to the display electronics 122 of the near-eye display device 120 in FIG. 1, the one or more projectors described in reference to the display electronics and/or the display 210 of the head-mounted display (HMD) device 200 in FIGS. 2A-2C, and/or the projector 330 of the near-eye display device 300 in FIGS. 3A-3B).

In some examples, the artificial intelligence (AI) module 170 may control micro-thermoelectric coolers (mTECs) integrated with components of the near-eye display device. In some examples, the artificial intelligence (AI) module 170 may control the micro-thermoelectric coolers (mTECs) integrated into the micro-light emitting diode (mLED) package assemblies 1300 and 1500 of FIGS. 13-14 and 15-16, respectively, which may be implemented/included in, for example, the one or more projectors of the display electronics 122 in the near-eye display device 120 in FIG. 1, the one or more projectors of the display electronics and/or the display 210 of the head-mounted display (HMD) device 200 in FIGS. 2A-2C, and/or the projector 330 of the near-eye display device 300 in FIGS. 3A-3B.

In some examples, the artificial intelligence (AI) module 170 may be employed to optimize the thermal, power, and/or optical operating performances and/or the user experience (UX) of the near-eye display device by monitoring sensor input of the near-eye display device, determining whether a change in one or more operating parameters may be desirable based on the sensor input, and, if it is determined that change is desirable, changing one or more operating parameters to effectuate the change. In some examples, the artificial intelligence (AI) module 170 may be employed to optimize the optical performance of the near-eye display device by monitoring temperature sensor input, determining whether a change in one or more operating parameters of micro-thermoelectric coolers (mTECs) integrated into one or more components of the near-eye display device may be desirable based on the monitored temperature, and, if it is determined that change is desirable, changing the one or more operating parameters of the integrated micro-thermoelectric coolers (mTECs). In some examples, the micro-thermoelectric coolers (mTECs) may be integrated with one or more micro-light emitting diodes (mLEDs) of the near-eye display device.

FIG. 17 is a graph of the modulation transfer function (MTF) of the emitters/sub-pixels of a light emitting diode (LED) vs. the ambient temperature (in Celsius), illustrating how certain temperature ranges may degrade the optical performance of the light emitting diode (LED), which may be mitigated by artificial intelligence (AI) and integrated micro-thermoelectric coolers (mTECs) according to examples of this portion of the present disclosure (II. Adaptive Thermal Mgmt using MTECs & AI). In FIG. 17, a line 1710 represents the modulation transfer function (MTF) of the red emitter/sub-pixel of a light emitting diode (LED), a line 1720 represents the modulation transfer function (MTF) of the blue emitter/sub-pixel of a light emitting diode (LED), and a line 1730 represents the modulation transfer function (MTF) of the green emitter/sub-pixel of a light emitting diode (LED). A dotted horizontal line 1750 represents the boundary between acceptable/optimal and unacceptable/sub-optimal optical performance as indicated by the modulation transfer function (MTF), i.e., the optical performance is degraded when below the dotted line 1750.

As shown in FIG. 17, the ambient temperature affects the optical performance of the red emitter/sub-pixel of a light emitting diode (LED) the most, indicating the optical performance is degraded below about 10° C. and above about 33° C. The optical performances of all three emitters/sub-pixels peak at about 25° C. and, although not as badly affected as the red emitter/sub-pixel, the optical performances (as indicated by their respective modulation transfer functions (MTFs) 1720 and 1730) of the blue and green emitters/sub-pixels also degrade as the ambient temperature increases or decreases from that peak.

FIGS. 18 and 19 are a table and a flowchart, respectively, illustrating a method for monitoring and maintaining an optimal optical performance and/or user experience (UX) using artificial intelligence (AI) and integrated micro-thermoelectric coolers (mTECs) according to examples of this portion of the present disclosure (II. Adaptive Thermal Mgmt using MTECs & AI). More specifically, FIG. 18 is a table of scenarios, parameters, actions, and outcomes corresponding to a method 1900 in FIG. 19 for an artificial intelligence (AI), such as, e.g., the artificial intelligence 170 in FIG. 1, to monitor the temperature and/or user comfort (or user experience (UX)) of a near-eye display device and control one or more micro-thermoelectric coolers (mTECs) integrated with one or more micro-light emitting diodes (mLEDs) of the near-eye display device (such as, e.g., the micro-thermoelectric coolers (mTECs) integrated into the micro-light emitting diode (mLED) package assemblies 1300 and 1500 of FIGS. 13-14 and 15-16, respectively). The method 1900 shown in FIG. 19 is provided by way of example and may only be one part of an entire process/procedure. The method 1900 may further omit parts of the method not germane to this portion of the present disclosure (II. Adaptive Thermal Mgmt using MTECs & AI), as would be understood by one of ordinary skill in the art. Each block shown in FIG. 19 may further represent one or more steps, processes, methods, or subroutines, as would be understood by one of ordinary skill in the art. For the sake of convenience and ease of explanation, the blocks in FIG. 19 and the description of FIGS. 18 and 19 herein may refer to the components shown in the Figures described herein; however, the method 1900 is not limited in any way to the components, apparatuses, and/or constructions shown in any of Figures described herein.

In blocks 1910 and 1920 of FIG. 19, the artificial intelligence (AI), which may be deployed in the near-eye display system's operating system (e.g., the "system OS" in FIG. 19), monitors the temperature and/or user experience (UX) (or "user comfort" in FIG. 19). As discussed above, the artificial intelligence (A) may be located and/or integrated, in whole or in part, in the near-eye display device (such as, e.g., the artificial intelligence 170 in FIG. 1) and/or may be located, in whole or in part, remotely from the near-eye display device but have a wired and/or wireless communication connection with the near-eye display device at least for purposes of controlling the integrated micro-thermoelectric coolers (mTECs), according to various examples of this portion of the present disclosure (II. Adaptive Thermal Mgmt using MTECs & AI). Similarly, in some examples, the sensors monitoring the temperature and/or user experience (UX) may be located and/or integrated, in whole or in part, in the near-eye display device (such as, e.g., the one or more temperature sensor(s) 136 in FIG. 1) and/or may be located, in whole or in part, remotely from the near-eye display device but have a communication connection with the artificial intelligence (AI) at least for purposes of informing the artificial intelligence (AI) of the current temperature and/or environmental conditions.

In some examples, the temperature and/or user experience (UX) may be monitored by one or more temperature sensors (such as, e.g., the one or more temperature sensor(s) 136 in FIG. 1), by monitoring the physical state of the user, and/or by monitoring the operating parameters of the near-eye display device. Examples monitoring the physical state of the user may monitor, for example, the temperature of the user, whether any sweat may be detected on the user, whether the eyes of the user are dilated (which may be detected via, e.g., the eye tracking system 118/120 in FIG. 1), etc., as would be understood by one of ordinary skill in the art. Examples monitoring the operating parameters of the near-eye display device may monitor (directly and/or indirectly, by measuring the effects thereof), for example, the brightness of the projected image light of the near-eye display device, the modulation transfer function (MTF) of the projected image light of the near-eye display device, the contrast of the projected image light of the near-eye display device, etc., as would be understood by one of ordinary skill in the art.

As shown in FIG. 18, when the ambient temperature is about 25° C., the temperature of the micro-light emitting diodes (mLEDs) of the near-eye display device is roughly 45° C., which provides an optimal modulation transfer function (MTF) of 80, and thus an optimal optical performance/user experience (UX) (indicated by the "+" in FIG. 18). Accordingly, no action is taken, as shown by block 1930 on FIG. 19. As shown in FIG. 18, when the ambient temperature is about 35° C. ("Hot"), the temperature of the micro-light emitting diodes (mLEDs) of the near-eye display device is roughly 55° C., which provides a degraded modulation transfer function (MTF) of 40, and thus a degraded optical performance/user experience (UX) (indicated by the "–" in FIG. 18). Accordingly, action is taken, as shown by block 1940 on FIG. 19. Similarly, when the ambient temperature is about 0° C. ("Cold"), the temperature of the micro-light emitting diodes (mLEDs) of the near-eye display device is roughly 10° C., which provides a degraded modulation transfer function (MTF) of 50, and thus a degraded optical performance/user experience (UX) (indicated by the "–" in FIG. 18). Accordingly, action is taken, as shown by block 1940 on FIG. 19.

In block 1940 of FIG. 19, the artificial intelligence (AI) deploys the one or more micro-thermoelectric coolers (mTECs) integrated into the one or more micro-light emitting diodes (mLEDs) of the near-eye display device in response to the degraded optical performance/user experience (UX) detected in block 1920, as discussed in the preceding paragraph. As shown in FIG. 18, when the monitored optical performance/user experience (UX) is indicated to be degraded by heat, the artificial intelligence (AI) cools the one or more micro-light emitting diodes (mLEDs) by running a current through the one or more micro-thermoelectric coolers (mTECs) integrated in the one or more micro-light emitting diodes (mLEDs) in the appropriate direction. Similarly, when the monitored optical performance/user experience (UX) is indicated to be degraded by the cold, the artificial intelligence (AI) heats the one or more micro-light emitting diodes (mLEDs) by running a current through the one or more micro-thermoelectric coolers (mTECs) integrated in the one or more micro-light emitting diodes (mLEDs) in the opposite direction.

In some examples, the artificial intelligence (AI) performs the method 1900 by training; in some examples, the artificial intelligence (AI) performs the method 1900 by table lookup and/or by accessing a database containing appropriate actions corresponding to present environmental conditions. In some examples, the artificial intelligence (AI) continually trains and thereby continually adapts its responses based on detected patterns. Such an example is described in reference to FIG. 20 below.

FIG. 20 is a flowchart illustrating a method for adaptive thermal management using artificial intelligence (AI) and integrated micro-thermoelectric coolers (mTECs) according to examples of this portion of the present disclosure (II. Adaptive Thermal Mgmt using MTECs & AI). The method 2000 shown in FIG. 20 is provided by way of example and may only be one part of an entire process, procedure, ongoing operation, method, etc. The method 2000 may further omit parts of the process, procedure, ongoing operation, method, etc, not germane to this portion of the present disclosure (II. Adaptive Thermal Mgmt using MTECs & AI), as would be understood by one of ordinary skill in the art. Each block shown in FIG. 20 may further represent one or more steps, processes, methods, or subroutines, as would be understood by one of ordinary skill in the art. For the sake of convenience and ease of explanation, the blocks in FIG. 20 may refer to the components shown in the Figures described herein; however, the method 2000 is not limited in any way to the components, apparatuses, and/or constructions shown in any of the Figures described herein. For instance, the description below may refer to the artificial intelligence (AI) module 170 in FIG. 1, the projectors described in reference to FIGS. 1, 2A-2C, and 3A-3B, the micro-light emitting diodes (mLEDs) and micro-thermoelectric coolers (mTECs) of FIGS. 13-14 and 15-16, etc., but methods according to this portion of the present disclosure (II. Adaptive Thermal Mgmt using MTECs & AI) are not limited in any way to the specific details of the artificial intelligence (AI) module 170 in FIG. 1, the projectors described in reference to FIGS. 1, 2A-2C, and 3A-3B, the micro-light emitting diodes (mLEDs) and micro-thermoelectric coolers (mTECs) of FIGS. 13-14 and 15-16, or any of the other components, apparatuses, and/or constructions shown and described in reference to any of the Figures described herein.

In block 2010, at least one initial model for thermal management may be established. This may be performed as part of the manufacturing process of the near-eye display device, before the end user receives and starts using it. This may be an optional part of the method, as one or more thermal management models may also be created while the near-eye display device is being used by the user. In some examples, the thermal management models, initial or otherwise, may include a wide variety of operational, environmental, and system parameters/variables along with related actions based on a current value of one or more of those operational, environmental, and system parameters. In some examples, the actions may be related to complex patterns of inter-related operational, environmental, and system parameters. In some examples, the thermal management model may be as simple as the table in FIG. 18, where temperature thresholds are related to making the integrated thermoelectric coolers (mTECS) either heat or cool the light sources in which they are integrated. In some examples, an initial thermal management model may be based on a large data set amassed (by, e.g., the manufacturer) for such a purpose.

In some examples, the operational, environmental, and system parameters/variables may be any one or more of the following: temperature (which may be sensed/detected in a wide variety of ways at a wide variety of places), location (which also may be sensed/detected in a wide variety of ways at varying levels of granularity), features of the visible local environment (such as, e.g., the brightness of sunshine or interior lighting, etc., as seen by, e.g., a camera integrated into the near-eye display device), features of the audible local environment (such as, e.g., the sound level of nearby people, which may indicate a crowd and/or a performance, or machinery, which may indicate an industrial environment, as heard by, e.g., one or more microphones integrated into the near-eye display device), features/conditions of the user (such as, e.g., heart rate, skin moisture (i.e., sweat), eye dilation, etc.), input by the user, a communication network, and/or the near-eye display device itself, etc., as would be understood by one of ordinary skill in the art. In some examples, the at least one initial thermal management model may be uploaded to a memory/storage of the near-eye display device and/or made available to the near-eye display device by wired/wireless communication.

In block 2020, one or more operational, environmental, and system parameters/variables are monitored. In some examples, a temperature of the user, the near-eye display device, and/or the external environment may be monitored. In some examples, the temperature of one or more heat sources in the near-eye display device, such as any light source (like, e.g., the one or more projectors of the display electronics 122 in the near-eye display device 120 in FIG. 1, the one or more projectors of the display electronics and/or the display 210 of the head-mounted display (HMD) device 200 in FIGS. 2A-2C, and/or the projector 330 of the near-eye display device 300 in FIGS. 3A-3B), may be monitored. In some examples, the location of the near-eye display device may be monitored via, for example, a global positioning system (GPS) receiver, a camera, a microphone, wireless communication with a local network, etc.

Any single parameter/variable may be monitored in a wide variety of ways with a wide variety of techniques and instrumentalities, as would be understood by one of ordinary skill in the art. In examples where the temperature is being monitored, the temperature may be monitored not only by temperature sensors, but also (or rather) may be determined using other devices or means, such as the eye-tracking system (by measuring eye dilation), a camera or light sensor (for detecting sweat on the user's skin), the total energy/power being used in/by the near-eye display device (by extrapolating the likely quantity of heat being dissipated and/or using the battery management unit (BMU)), etc. In some examples, the instrumentalities for monitoring the one or more operational, environmental, and system parameters/variables may not be part of, or located near, the near-eye display device but rather the instrumentalities may be remote from the near-eye display device, and the monitoring data may be retrieved via wireless communication from a local/wide/area network and/or a telecommunications system.

In block 2025, it is determined whether action is indicated and/or required. What this means may depend on the requirements and characteristics of the particular example and/or the one or more thermal management models being employed by the artificial intelligence of the near-eye display device. In some examples where temperature is being monitored, the indication may be based on temperature thresholds such as those discussed in reference to FIGS. 18 and 19 above. In some examples where location is being monitored, the indication may be a change in location, e.g., from inside to outside, moving into a place which is associated with heating or cooling, etc. In some examples where the condition of the user is being monitored, the indication may be based on certain indicators of stress, heating, excitement, etc., such as sweat, increased heart rate, eye dilation, etc. In some examples where the operating conditions of the near-eye display device are being monitored, the indication may be certain thresholds based on the energy/power being used in/by one, more, and/or all of the components in the near-eye display device.

In some examples, the one or more thermal management models may have predictive/preemptive indications for action. For instance, monitoring and adaptive learning may "teach" the one or more thermal management models (i.e., by establishing a clear probabilistic pattern of case and effect; see discussion in reference to block 2040 below) that one or more conditions signal a possible future change in temperature and/or other operating condition requiring/suggesting a change in one or more operating parameters. In some examples, adaptive learning and modeling may have established that moving into a particular location is almost always associated with heating or cooling that may require that action be taken to maintain, e.g., optimal operating conditions and/or user comfort. In some examples, adaptive learning and modeling may have established that playing a particular game, engaging in a particular virtual reality (VR)/augmented reality (AR) activity, and/or engaging in certain physical activity is almost always associated with heating or cooling that may require that action be taken to maintain, e.g., optimal operating conditions and/or user comfort. In some examples, adaptive learning and modeling may have established that heating or cooling is associated with a particular time of day, and thus preemptive action may be taken before that time to maintain, e.g., optimal operating conditions and/or user comfort.

If it is determined, based on the one or more thermal management models, that action may be indicated/required in block 2025, the appropriate action(s) may be taken at block 2030. What this means may depend on the requirements and characteristics of the particular example and/or the one or more thermal management models being employed by the artificial intelligence of the near-eye display device. In some examples where the indication in block 2025 is that a temperature threshold has been crossed, the action may be to send the appropriate current flow through one or more thermoelectric coolers (mTECs) integrated into one or more heat sources in the near-eye display devices, where the direction of the current flow may depend on the type of action indicated, e.g., heating or cooling. In some examples where the indication in block 2025 is that a temperature threshold has been crossed, the action may be to change one or more other parameters regarding the one or more thermoelectric coolers (mTECs) integrated into one or more heat sources in the near-eye display devices, such as, e.g., activating only specific integrated thermoelectric coolers (mTECs) but not all, changing voltage/current levels, etc.

In some examples, the appropriate action(s) may also involve other components, functionalities, and/or operating parameters besides the one or more integrated thermoelectric coolers (mTECs). In some examples, the other components, functionalities, and/or operating parameters besides the one or more integrated thermoelectric coolers (mTECs) may be related to user comfort/user experience (UX). In some examples, multiple related or seemingly unrelated actions (but indicated by the one or more thermal management models) may be taken in block 2030.

At block 2040, after appropriate action is taken in block 2030, or if it is determined that no action is required in block 2025, the current monitoring and/or action data (from, e.g., blocks 2025 and/or 2030) may be used to train, refine, adjust, adapt, and/or otherwise modify the one or more thermal management models. In some examples, the training, refining, adjusting, adapting, and/or otherwise modifying in block 2040 is part of a process of recognizing/detecting patterns where certain actions are usually indicated/required, i.e., part of creating thermal management model(s) that may take predictive/preemptive actions before actual detrimental changes in temperature and/or user comfort/user experience (UX) are actually detected. In some examples, a particular pattern of temperature changes, a specific pattern of moving between and among particular places, a certain pattern of playing a particular game(s), a particular pattern of engaging in a certain virtual reality (VR)/augmented reality (AR) activity or activities, a specific pattern of engaging in certain physical activity, any pattern involving any or more of the above, any patterns involving any one or more operational, environmental, and system parameters/variables, and/or any pattern involving any such combination thereof, may be established, at least in part, in block 2040.

After block 2040, the method/process loops back to block 2020. As would be understood by one of ordinary skill in the art, any of the blocks in FIG. 20 may occur in a different order and/or simultaneously (e.g., in parallel). In some examples, block 2010 may not be performed, or may be performed multiple times, and/or an additional one or more blocks involving an outside entity (such as, e.g., the manufacturer) inserting outside data and/or actions into, and/or otherwise modifying, the one or more thermal management models of the near-eye display device may be performed.

FIGS. 21 and 22 are flowcharts illustrating methods for manufacturing a heat source (e.g., a light source) with an integrated micro-thermoelectric cooler (mTEC) which may be used in a near-eye display device according to examples of this portion of the present disclosure (II. Adaptive Thermal Mgmt using MTECs & AI). The methods 2100 and 2200 shown in FIGS. 21 and 22 are provided by way of example and may only be one part of an entire manufacturing process, as would be understood by one of ordinary skill in the art. The methods 2100 and 2200 may further omit parts of any process, procedure, ongoing operation, method, etc., involved in manufacturing a heat source with an integrated micro-thermoelectric cooler (mTEC) not germane to this portion of the present disclosure (II. Adaptive Thermal Mgmt using MTECs & AI), as would be understood by one of ordinary skill in the art. Each block shown in FIGS. 21 and 22 may further represent one or more steps, processes, methods, or subroutines, as would be understood by one of ordinary skill in the art. For the sake of convenience and ease of explanation, the blocks in FIGS. 21 and 22 may refer to the components shown in the Figures described herein; however, the methods 2100 and 100B are not limited in any way to the components, apparatuses, and/or constructions shown in any of the Figures described herein. For instance, the description below may refer to the micro-light emitting diodes (mLEDs) and micro-thermoelectric coolers (mTECs) of FIGS. 12, 13-14 and 15-16, etc., but methods according to this portion of the present disclosure (II. Adaptive Thermal Mgmt using MTECs & AI) are not limited in any way to the specific details of the micro-light emitting diodes (mLEDs) and micro-thermoelectric coolers (mTECs) of FIGS. 12, 13-14 and 15-16, or any of the other components, apparatuses, and/or constructions shown and described in reference to any of the Figures described herein.

More specifically, FIG. 21 is a flowchart illustrating a method 2100 for manufacturing a micro-light emitting diode (mLED) package assembly where one or more micro-thermoelectric coolers (mTECs) may be integrated in a substrate under the micro-light emitting diode (mLED) according to examples of this portion of the present disclosure (II. Adaptive Thermal Mgmt using MTECs & AI), and FIG. 22 is a flowchart illustrating a method 2200 for manufacturing a micro-light emitting diode (mLED) package assembly where one or more micro-thermoelectric coolers (mTECs) may be integrated above the micro-light emitting diode (mLED) according to examples of this portion of the present disclosure (II. Adaptive Thermal Mgmt using MTECs & AI). In some examples, a manufacturing process may be used where one or more micro-thermoelectric coolers (mTECs) may be integrated more directly into one or more micro-light emitting diodes (mLEDs) of the micro-light emitting diode (mLED) package assembly, in a manner similar to, for example, the integration of the micro-thermoelectric cooler (mTEC) into the hybrid laser assembly 1200 in FIG. 12.

At block 2105 in FIG. 21, a micro-thermoelectric cooler (mTEC) may be fabricated into and/or slightly above (perhaps in part) a substrate layer of a micro-light emitting diode (mLED) package assembly. In some examples, the micro-thermoelectric cooler (mTEC) may be fabricated into and/or slightly above (perhaps in part) a substrate-on-insulator (SOI) package layer of a micro-light emitting diode (mLED) package assembly such as, e.g., the micro-thermoelectric cooler (mTEC) in the micro-thermoelectric cooler (mTEC) layer 1350 in the package layer 1330 of FIG. 13.

At block 2110 in FIG. 21, a micro-light emitting diode (mLED) may be fabricated above and/or (more or less) into the substrate layer with the integrated micro-thermoelectric cooler (mTEC) of a micro-light emitting diode (mLED) package assembly. In some examples, the micro-light emitting diode (mLED) may be fabricated above a substrate-on-insulator (SOI) package layer of a micro-light emitting diode (mLED) package assembly such as, e.g., the micro-light emitting diode (mLED) layer 1340 and 1345 of the micro-light emitting diode (mLED) package assembly 1300 of FIG. 13.

At block 2210 of FIG. 22, a micro-light emitting diode (mLED) may be fabricated in a micro-light emitting diode (mLED) package assembly. In some examples, the micro-light emitting diode (mLED) may be fabricated above a substrate-on-insulator (SOI) package layer of a micro-light emitting diode (mLED) package assembly such as, e.g., the micro-light emitting diode (mLED) layer 1540 and 1545 of the micro-light emitting diode (mLED) package assembly 1500 of FIG. 15.

At block 2220 of FIG. 22, a micro-thermoelectric cooler (mTEC) may be fabricated above and/or (more or less) integrated into the micro-light emitting diode (mLED) fabricated in block 2210, in a micro-light emitting diode (mLED) package assembly. In some examples, the micro-thermoelectric cooler (mTEC) may be fabricated above a micro-light emitting diode (mLED) of a micro-light emitting diode (mLED) package assembly such as, e.g., the micro-thermoelectric coolers (mTECs) above the micro-light emitting diode (mLED) layer 1540 and 1545 the micro-light emitting diode (mLED) package assembly 1500 of FIG. 15.

In some examples, any suitable deposition process may be employed in the fabrication processes of blocks 2105, 2110, 2210, and 2215, as would be understood by one of ordinary skill in the art, such as, for example, metal-organic chemical vapor deposition, physical vapor deposition (PVD), chemical vapor deposition (CVD), atomic layer deposition (ALD), and the like. In some examples, thermal evaporation, spray-coating, spin-coating, sputtering, printing, stamping, ball milling, melt spinning, spark plasma sintering, and the like may be employed, as would be understood by one of ordinary skill in the art. In some examples, electrodeposition may be employed in blocks 2105 and/or 2215 to fabricate the thermoelectric n-type and p-type legs of the micro-thermoelectric cooler (mTEC), similar to the electrodeposition process described in reference to FIG. 12 above.

As indicated above, the fabrication processes in blocks 2105 and 2110 of FIG. 21 and/or blocks 2210 and 2215 of FIG. 22 may overlap and/or may occur substantially simultaneously. For instance, the fabrication in blocks 2105 and 2110 of FIG. 21 may occur substantially simultaneously as part of a continuous electrodeposition process. In some examples where the micro-thermoelectric cooler (mTEC) and the micro-light emitting diode (mLED) are integrated in a manner similar to the micro-thermoelectric cooler (mTEC) and the laser diode of FIG. 12, the bottom electrode(s) of the micro-thermoelectric cooler (mTEC) may be formed before/during the formation of the bottom of the micro-light emitting diode (mLED), the thermoelectric legs of the micro-thermoelectric cooler (mTEC) may be formed substantially simultaneously with the formation of the middle/body of the micro-light emitting diode (mLED), and the top electrode(s) of the micro-thermoelectric cooler (mTEC) are formed after/during the formation of the top (e.g., the emitters/sub-pixels) of the micro-light emitting diode (mLED).

According to examples, micro-thermoelectric coolers (mTECs) integrated into heat sources of a near-eye display device, as well as methods of manufacturing micro-thermoelectric coolers (mTECs) integrated into heat sources of a near-eye display device, are described herein. According to examples, methods, systems, and apparatuses for thermal management of a near-eye display device using artificial intelligence (AI) and integrated micro-thermoelectric coolers (mTECs) are also described herein. A non-transitory computer-readable storage medium may have an executable stored thereon, which when executed instructs a processor to perform the methods described herein.

In the foregoing description (i.e., this portion of the present disclosure (II. Adaptive Thermal Mgmt using MTECs & AI)), various inventive examples are described, including devices, systems, methods, and the like. For the purposes of explanation, specific details are set forth in order to provide a thorough understanding of examples of the disclosure. However, it will be apparent that various examples may be practiced without these specific details. For example, devices, systems, structures, assemblies, methods, and other components may be shown as components in block diagram form in order not to obscure the examples in unnecessary detail. In other instances, well-known devices, processes, systems, structures, and techniques may be shown without necessary detail in order to avoid obscuring the examples.

The figures and description are not intended to be restrictive. The terms and expressions that have been employed in this disclosure are used as terms of description and not of limitation, and there is no intention in the use of such terms and expressions of excluding any equivalents of the features shown and described or portions thereof. The word "example" is used herein to mean "serving as an example, instance, or illustration." Any embodiment or design described herein as an "example" is not necessarily to be construed as preferred or advantageous over other embodiments or designs.

II.5

In one aspect, this portion of the present disclosure (II. Adaptive Thermal Mgmt using MTECs & AI) is directed to a near-eye display device, comprising: a frame; an optical assembly disposed within the frame; and a projector disposed in the frame to project an image through the optical assembly to an eye, the projector comprising: a light source; and a micro-thermoelectric cooler (mTEC) integrated in the light source, the integrated micro-thermoelectric cooler (mTEC) to at least one of cool or heat the light source.

In some examples of this aspect, the integrated micro-thermoelectric cooler (mTEC) comprises: a first thermoelectric leg having a top and a bottom; a first bottom electrode forming an electrical connection with the bottom of the first thermoelectric leg; a second thermoelectric leg having a top and a bottom; a top electrode forming an electrical connection between the top of the first thermoelectric leg and the top of the second thermoelectric leg; and a second bottom electrode forming an electrical connection with the bottom of the second thermoelectric leg; wherein, when an electrical current flows from the first bottom electrode to the second bottom electrode, the light source is cooled and, when an electrical current flows from the second bottom electrode to the first bottom electrode, the light source is heated. In such examples, the first thermoelectric leg may be comprised of an n-type thermoelectric semiconductor; and the second thermoelectric leg may be comprised of a p-type thermoelectric semiconductor.

In some examples of this aspect, the light source comprises a micro-light emitting diode (mLED) and a substrate. In such examples, the micro-thermoelectric cooler (mTEC) is integrated into at least one of the micro-light emitting diode (mLED) or the substrate. Further, in such examples, the micro-light emitting diode (mLED) comprises at least one of an organic light emitting diode (OLED), an inorganic light emitting diode (ILED), an active-matrix organic light emitting diode (AMOLED), or a transparent organic light emitting diode (TLED).

In some examples of this aspect, the light source comprises at least one of a laser, a laser diode, a light emitting diode (LED), a vertical cavity surface emitting laser (VCSEL), a liquid crystal display (LCD) panel, a liquid-crystal-on-silicon (LCoS) display panel, an organic light-emitting diode (OLED) display panel, a micro light-emitting diode (micro-LED) display panel, a digital light processing (DLP) display panel, or a laser scanning display panel.

In some examples of this aspect, the near-eye display device further comprises: a processor; and a non-transitory computer-readable storage medium having an executable stored thereon, which when executed instructs the processor to perform: monitoring a temperature of at least one of the near-eye display device or a user of the near-eye display device; determining, using a thermal management model, whether to at least one of cool or heat the light source based on the monitored temperature; and controlling, if it is determined to at least one of cool or heat the light source, the integrated micro-thermoelectric cooler (mTEC) to at least one of cool or heat the light source based on the thermal management model. In such examples, the non-transitory computer-readable storage medium may further store the thermal management model. In such examples, the thermal management model may be a lookup table. In such examples, the processor may further perform training the thermal management model. In such examples, near-eye display device may further comprise: at least one temperature sensor disposed in the frame to monitor the temperature of the near-eye display device. In such examples, near-eye display device may further comprise: at least one sensor disposed in the frame to provide input to the thermal management model.

In another aspect, this portion of the present disclosure (II. Adaptive Thermal Mgmt using MTECs & AI) is directed to a method for thermal management of a near-eye display device comprising a light source, comprising: monitoring a temperature of at least one of the near-eye display device or a user of the near-eye display device; determining, using a thermal management model, whether to at least one of cool or heat the light source based on the monitored temperature; and controlling, if it is determined to at least one of cool or heat the light source, a micro-thermoelectric cooler (mTEC) integrated in the light source to at least one of cool or heat the light source based on the thermal management model.

In some examples of another aspect, the method further comprises training the thermal management model based on input of at least one sensor disposed in the near-eye display device.

In some examples of another aspect, the thermal management model comprises a lookup table, and the step of determining, based on a thermal management model, whether to at least one of cool or heat the light source based on the monitored temperature comprises: determining whether the monitored temperature exceeds a threshold value in the lookup table of the thermal management model.

III. Embedded Motheye Structure

III.1

This portion of the present disclosure relates generally to optical lens assemblies, and more specifically, to the lenses in the optical lens assemblies of wearable augmented reality (AR) display devices.

III.2

With recent advances in technology, the prevalence and proliferation of content creation and delivery has increased greatly in recent years. In particular, interactive content such as virtual reality (VR) content, augmented reality (AR) content, mixed reality (MR) content, and content within and associated with a real and/or virtual environment (e.g., a "metaverse") has become appealing to consumers.

To facilitate delivery of this and other related content, service providers have endeavored to provide various forms of wearable display systems. One such example may be a head-mounted display (HMD) device, such as a wearable eyewear, a wearable headset, or eyeglasses. In some examples, the head-mounted display (HMD) device may project or direct light to may display virtual objects or combine images of real objects with virtual objects, as in virtual reality (VR), augmented reality (AR), or mixed reality (MR) applications. For example, in an augmented reality (AR) system, a user may view both images of virtual objects (e.g., computer-generated images (CGIs)) and the surrounding environment. Head-mounted display (HMD) devices may also present interactive content, where a user's (wearer's) gaze may be used as input for the interactive content.

Wearable display devices, such as virtual reality (VR), augmented reality (AR), and/or mixed reality (MR) glasses, may require increasingly complex and intricate lens assembly structures, thereby complicating the manufacturing process. Moreover, wearable display devices, such as virtual reality (VR), augmented reality (AR), and/or mixed reality (MR) glasses, may need to satisfy a wide range of sometimes competing requirements, such as, for example, the need for relatively small size and negligible weight for portability and user comfort, the manufacturing requirements for such complex and intricate optical and electronic assembly structures required to improve the user experience.

III.3.

Features of this portion of the present disclosure (III. Embedded motheye Structure) are illustrated by way of example and not limited in the following figures, in which like numerals indicate like elements. One skilled in the art will readily recognize from the following that alternative examples of the structures and methods illustrated in the figures can be employed without departing from the principles described herein.

FIGS. 2A-2C illustrate various views of a near-eye display device in the form of a head-mounted display (HMD) device 200, according to examples.

FIGS. 3A and 3B illustrate various views of a near-eye display device 300 in the form of a pair of glasses (or other similar eyewear), according to an example.

Figure 23:
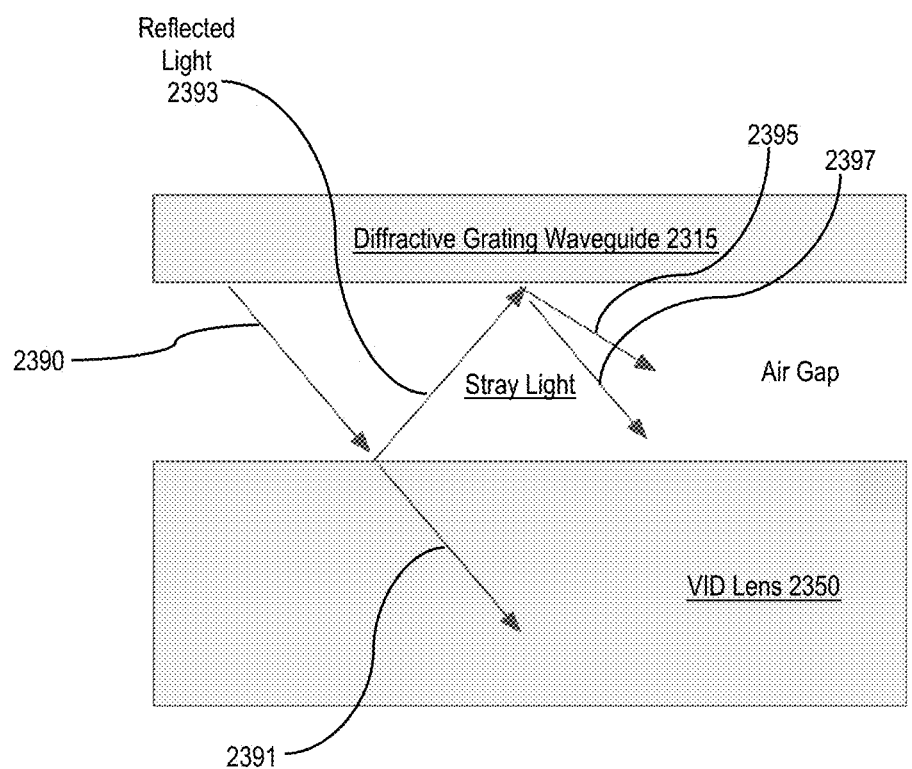

FIG. 23 is a simplified block diagram illustrating the internal reflections causing stray light and ghost images which may be avoided by using an embedded sub-wavelength structure, according to examples of this portion of the present disclosure (III. Embedded motheye Structure).

FIG. 24 is a simplified block diagram of a cross-section of an optical lens assembly employing a motheye structure embedded in a virtual image distance (VID) lens, according to an example.

FIG. 25 illustrates close-up views of the embedded motheye structure from FIG. 24, according to examples of this portion of the present disclosure (III. Embedded Motheye Structure).

FIGS. 26, 27, and 28 are block diagrams illustrating three different manufacturing processes for the embedded motheye structure, according to examples of this portion of the present disclosure (III. Embedded Motheye Structure).

Figure 29:
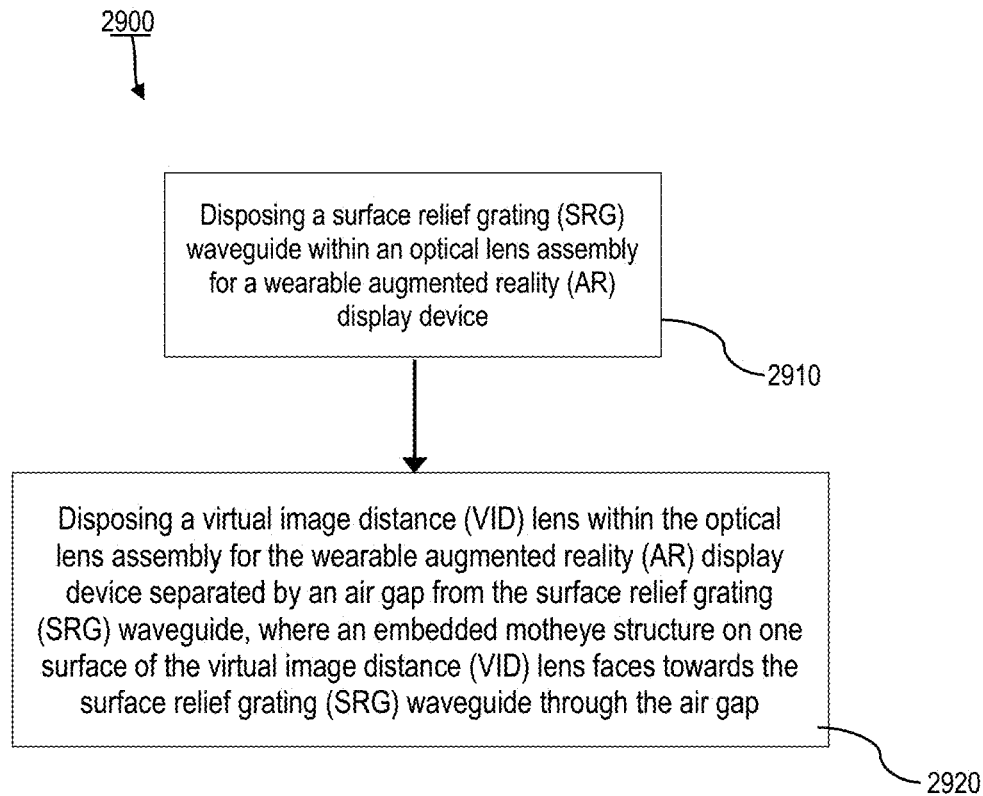

FIG. 29 illustrates a flow diagram for manufacturing an optical lens assembly for a wearable augmented reality (AR) display device, according to some examples.

Figure 30:
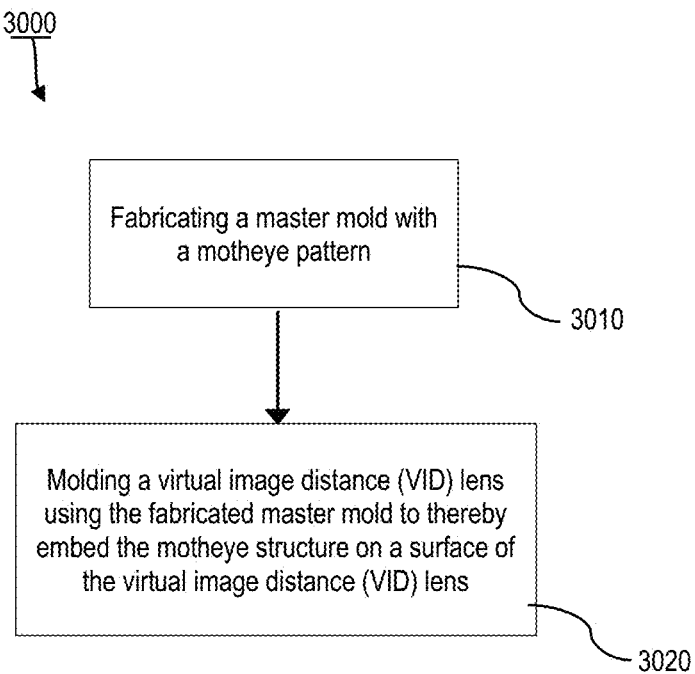

FIG. 30 illustrates a flow diagram for manufacturing a virtual image distance (VID) lens for an optical lens assembly in a wearable augmented reality (AR) display device, according to some examples.

III.4.

For simplicity and illustrative purposes, this portion of the present disclosure is described by referring mainly to examples thereof. In the following description, numerous specific details are set forth in order to provide a thorough understanding of this portion of the present disclosure. It will be readily apparent, however, that this portion of the present disclosure may be practiced without limitation to these specific details. In other instances, some methods and structures readily understood by one of ordinary skill in the art have not been described in detail so as not to unnecessarily obscure this portion of the present disclosure. As used herein, the terms "a" and "an" are intended to denote at least one of a particular element, the term "includes" means includes but not limited to, the term "including" means including but not limited to, and the term "based on" means based at least in part on.

As used herein, a "near-eye display device" may refer to any display device (e.g., an optical device) that may be in close proximity to a user's eye. Accordingly, a near-eye display device may be a head-mounted display (HMD) device, such as a wearable eyewear, a wearable headset, and/or "smartglasses," which may be used for interacting with virtual reality (VR), augmented reality (AR), and/or mixed reality (MR) environments, or any environment of real and virtual elements, such as a "metaverse." As used herein, a "wearable device" may refer to any portable electronic device that may be worn on any body part of a user and used to present audio and/or video content, control other devices, monitor bodily functions, and perform similar actions. As used herein, a "user" may refer to a user or wearer of a "near-eye display device" and/or a "wearable display."

In a wearable augmented reality (AR) display device, a virtual image distance plane/virtual image display (VID) lens, or virtual image lens, may focus a virtual image projected by a display projector or waveguide onto the user's eye, thereby integrating, from the user's perspective, the projected virtual image with the actual scene of the outside environment seen through the wearable augmented reality (AR) display device. However, the optical lens assemblies of wearable augmented reality (AR) display devices face challenges in terms of, e.g., complexity of architecture and manufacturing, the degradation of optical performance and optical components over time, etc.

According to examples of this portion of the present disclosure (III. Embedded Motheye Structure), systems and/or apparatuses for an embedded motheye structure on a surface of a virtual image distance plane/virtual image distance (VID) lens, or virtual image lens, used in an optical lens assembly of a wearable augmented reality (AR) display device, and methods for manufacturing the same, are presented.

In some examples, the embedded motheye structure may reduce stray light, allow broadband transmission therethrough, and improve optical performance. In some examples, the embedded motheye structure may eliminate a lamination process and/or optically clear adhesive (OCA) being used on the virtual image distance (VID) lens, or virtual image lens, thereby decreasing the possible degradation caused by warping, waviness, bubbles, thermal degradation, etc. In some examples, the embedded motheye structure may simplify the architecture of the optical lens assembly and the manufacturing of the optical lens assembly, thereby, inter alia, reducing costs.

All of the previous paragraphs, including the descriptions of FIGS. 1, 2A-2C, and 3C, are incorporated in this portion of the present disclosure (III. Embedded Motheye Structure) in their entirety, to be read in addition to the following further comments on FIGS. 2A-3B.

FIGS. 2A-2C illustrate various views of a near-eye display device in the form of a head-mounted display (HMD) device 200, according to examples. In some examples, the head-mounted device (HMD) device 200 may be a part of a virtual reality (VR) system, an augmented reality (AR) system, a mixed reality (MR) system, another system that uses displays or wearables, or any combination thereof. For example, the head-mounted display (HMD) 200 may combine both the light of the external environment and images of artificial reality content (e.g., computer-generated images). For instance, the head-mounted display (HMD) 200 may augment images of a physical, real-world environment external to the head-mounted display (HMD) 200 with generated and/or overlaid digital content (e.g., images, video, sound, etc.) to present an augmented reality to a user.

As shown in FIG. 2A, the head-mounted display (HMD) device 200 may include a body 220 and a head strap 230. The front perspective view 200A of the head-mounted display (HMD) device 200 further shows a bottom side 223, a front side 225, and a right side 229 of the body 220. In some examples, the head strap 230 may have an adjustable or extendible length. In particular, in some examples, there may be a sufficient space between the body 220 and the head strap 230 of the head-mounted display (HMD) device 200 for allowing a user to mount the head-mounted display (HMD) device 200 onto the user's head. For example, the length of the head strap 230 may be adjustable to accommodate a range of user head sizes.

As shown in the bottom rear perspective view 200B of FIG. 2B and the bottom front perspective view 200C of FIG. 2C, the head-mounted display (HMD) device 200 may have the bottom side 223 and a left side 227 of the body 220, the head strap 230, and the display 210.

The display 210 may include one or more display assemblies and present, to a user (wearer), media or other digital content including virtual and/or augmented views of a physical, real-world environment with computer-generated elements. Examples of the media or digital content presented by the head-mounted display (HMD) device 200 may include images (e.g., two-dimensional (2D) or three-dimensional (3D) images), videos (e.g., 2D or 3D videos), audio, or any combination thereof. In other examples, the display 210 may include a projector, which may form an image in angular domain for direct observation by the user by painting the image on the user's eye.

In some examples, the display 210 may include any number of display electronics and display optics. In some examples, the display electronics may display or facilitate the display of images to the user according to data received from, for example, control electronics such as a virtual reality engine. In some examples, the display electronics may include one or more of a liquid crystal display (LCD) and/or a light-emitting diode (LED). In some examples, the display electronics may include any number of pixels to emit light of a predominant color such as red, green, blue, white, or yellow. In some examples, the display electronics may display a three-dimensional (3D) image, e.g., using stereoscopic effects produced by two-dimensional panels, to create a subjective perception of image depth. In some examples, the display 210 may include a projector, which may form an image in angular domain for direct observation by a user's eye through a pupil. The projector may employ a controllable light source (e.g., a laser source) and a micro-electromechanical system (MEMS) beam scanner to create a light field from, for example, a collimated light beam.

In some examples, the display optics may display image content optically (e.g., using optical waveguides and/or couplers) or magnify image light received from the display electronics, correct optical errors associated with the image light, and/or present the corrected image light to a user of the head-mounted display (HMD) device 200. In some examples, the display optics may include a single optical element or any number of combinations of various optical elements, such as waveguides, gratings, lenses, mirrors, etc., as well as mechanical couplings to maintain relative spacing and orientation of the optical elements in the combination. In some examples, one or more optical elements in the display optics may have an optical coating, such as an anti-reflective coating, a reflective coating, a filtering coating, and/or a combination of different optical coatings, as described in greater detail below. In some examples, the display optics may also be designed to correct one or more types of optical errors, such as two-dimensional optical errors (e.g., barrel distortion, pincushion distortion, longitudinal chromatic aberration, and/or transverse chromatic aberration), three-dimensional optical errors (e.g., spherical aberration, chromatic aberration field curvature, and/or astigmatism), or any combination thereof.

In some examples, the head-mounted display (HMD) device 200 may also include an eye-tracking system, one or more locators, one or more position sensors, and an inertial measurement unit (IMU). In some examples, the head-mounted display (HMD) device 200 may include various other sensors, such as depth sensors, motion sensors, image sensors, temperature sensors, light sensors, and/or the like. Some of these sensors may use any number of structured or unstructured light patterns for sensing purposes.

In some examples, the eye-tracking system may include an imaging system that captures one or more images of an eye and may optionally include a light emitter, which may generate light that is directed to the eye such that light reflected by the eye may be captured by the imaging system. As used herein, "eye tracking" may refer to determining an eye's position or relative position, including orientation, location, and/or gaze of a user's eye.

In other examples, the eye-tracking system may capture reflected radio waves emitted by a miniature radar unit. These data associated with the eye may be used to determine or predict eye position, orientation, movement, location, and/or gaze. In some examples, the head-mounted display (HMD) device 200 may use the orientation of the eye (as determined by the eye tracking system) to introduce depth cues (e.g., blur image outside of the user's main line of sight), collect heuristics on the user interaction in the virtual reality (VR) media (e.g., time spent on any particular subject, object, or frame as a function of exposed stimuli), some other functions that are based in part on the orientation of at least one of the user's eyes, or any combination thereof. In some examples, because the orientation may be determined for both eyes of the user, the eye-tracking system may be able to determine where the user is looking or predict any user patterns, etc. In some examples, the eye tracking system may be used to adjust and improve quality of the presented content, such as allowing the user to interact with the presented images or videos.

In some examples, the one or more locators may be located in specific positions relative to one another and relative to a reference point on the head-mounted display (HMD) device 200. In some examples, the one or more locators may be light sources which are captured by an optional external imaging device to determine the position and/or orientation of the head-mounted display (HMD) device 200. The one or more locators may each be a light-emitting diode (LED), a corner cube reflector, a reflective marker, a type of light source that contrasts with an environment in which the head-mounted display (HMD) device 200 operates, or any combination thereof.

In some examples, the one or more position sensors may generate one or more measurement signals in response to motion of the head-mounted display (HMD) device 200. Examples of the one or more position sensors may include any number of accelerometers, gyroscopes, magnetometers, and/or other motion-detecting or error-correcting sensors, or any combination thereof. In some examples, the inertial measurement unit (IMU) may be an electronic device that generates fast calibration data based on measurement signals received from the one or more position sensors. Based on the one or more measurement signals from the one or more position sensors, the inertial measurement unit (IMU) may generate fast calibration data indicating an estimated position of the head-mounted display (HMD) device 200 that may be relative to an initial position of the head-mounted display (HMD) device 200. For example, the inertial measurement unit (IMU) may integrate measurement signals received from accelerometers over time to estimate a velocity vector and integrate the velocity vector over time to determine an estimated position of a reference point on the head-mounted display (HMD) device 200. Alternatively, the inertial measurement unit (IMU) may provide the sampled measurement signals to a controller, processor, and/or virtual reality engine, which may determine the fast calibration data.

In some examples, the head-mounted display (HMD) device 200 may include one or more input/output interfaces that allow a user to send action requests to a controller, processor, and/or virtual reality engine through a wired or wireless connection. As used herein, an "action request" may be a request to perform a particular action. For example, an action request may be to start or to end an application or to perform a particular action within the application.

Example input/output interfaces may include a keyboard, a mouse, a game controller, a glove, a button, a touch screen, or any other suitable device for receiving action requests and communicating the received action requests.

In some examples, a controller, processor, and/or virtual reality engine may provide content to the head-mounted display (HMD) device 200 for presentation to the user in accordance with information received from one or more of the eye tracking system, the position sensors, the locators, and/or the input/output interfaces. For example, the head-mounted display (HMD) device 200 may include an application store, a headset tracking module, a virtual reality engine, and an eye-tracking module. Any one or more of these processors, controllers, and/or modules may include a processor and a non-transitory computer-readable storage medium storing instructions executable by the processor. The processor may include multiple processing units executing instructions in parallel. The non-transitory computer-readable storage medium may be any memory, such as a hard disk drive, a removable memory, or a solid-state drive (e.g., flash memory or dynamic random access memory (DRAM)). In some examples, modules such as, e.g., the headset tracking module, the virtual reality engine, and/or the eye-tracking module described in greater detail below, may be encoded as instructions in the non-transitory computer-readable storage medium that, when executed by the processor, cause the processor to perform the functions further described below. It should be appreciated that any of the controllers/processors, the application store, the headset tracking module, the virtual reality engine, and/or the eye-tracking module may be integrated with or separate from the head-mounted display (HMD) device 200.

In some examples, the application store may store one or more applications for execution by a controller/processor. An application may include a group of instructions that, when executed by a processor, generates content for presentation to the user. Examples of the applications may include gaming applications, conferencing applications, video playback applications, or other suitable applications.

In some examples, the headset tracking module may track movements of the head-mounted display (HMD) device 200 using slow calibration information from the locators and an external imaging device. For example, the headset tracking module may determine positions of a reference point of the head-mounted display (HMD) device 200 using observed locators from the slow calibration information and a model of the head-mounted display (HMD) device 200. Additionally, in some examples, the headset tracking module may use portions of the fast calibration information, the slow calibration information, or any combination thereof, to predict a future location of the head-mounted display (HMD) device 200. In some examples, the headset tracking module may provide the estimated or predicted future position of the head-mounted display (HMD) device 200 to the virtual reality engine.

In some examples, the virtual reality engine may execute applications within an artificial reality system environment and receive position information, acceleration information, velocity information, and/or predicted future positions of the head-mounted display (HMD) device 200 from the headset tracking module. In some examples, the virtual reality engine may also receive estimated eye position and orientation information from the eye-tracking module. Based on the received information, the virtual reality engine may determine content to provide to the head-mounted display (HMD) device 200 for presentation to the user. In some examples, the eye-tracking module may receive eye-tracking data from the eye-tracking system to determine the position of the user's eye based on the eye tracking data.

In some examples, the head-mounted display (HMD) device 200 may include additional, fewer, and/or different components than shown and/or described in reference to FIGS. 2A-2C above, such as a camera to capture images or videos of the user's environment to present the user with augmented reality (AR)/virtual reality (VR) content.

FIGS. 3A and 3B illustrate various views of a near-eye display device 300 in the form of a pair of glasses (or other similar eyewear), according to an example. FIG. 3A is a perspective view, and FIG. 3B is a top view, of the near-eye display device 300 in the form of a pair of glasses (or other similar eyewear), according to an example.

In some examples, the near-eye display device 300 may include a frame 305 and a display 310 having a waveguide 315 coupled to a projector 330 and optics 350. In some examples, light from a surrounding environment of the near-eye display device 300 may traverse a "see-through" region of the waveguide 315 in the display 310 to reach a user's eyes (located somewhere within an eye box 340), while images are also projected for the user to see as part of an augmented reality (AR) display and/or a mixed reality (MR) display. In such examples, the light of images projected by the projector 330 may be coupled into a transparent substrate of the waveguide 315, propagate within the waveguide 315, be coupled with light from the user's actual environment, and be directed out of the waveguide 315 at one or more locations towards a user's eye(s) located within the eye box 340.

In various examples according to this portion of the present disclosure (III. Embedded Motheye Structure), the waveguide 315 may be geometric, reflective, refractive, polarized, diffractive, and/or holographic, as would be understood of one of ordinary skill in the art, and may use any one or more of macro optics (such as, e.g., traditional optics, freeform prisms, and geometrical waveguide techniques, which may be based on Snell's law of reflection and refraction), micro optics (such as, e.g., diffractive grating techniques), and/or nano optics (such as, e.g., metalenses and/or metasurfaces, which may be based on the phase modulation effects of nanoscale structures).

Generally speaking, a diffractive waveguide system may comprise a light source, such as the projector 330, and a planar waveguide element that integrates an in-coupling diffractive grating and an out-coupling diffractive grating, such as the waveguide 315, as well as optics for projecting both the virtual image and the "see-through" real world scene to the user's eye, such as optics 350. In such examples, the waveguide 315 may use the in-coupling diffractive grating to receive the light projected by the projector 330, and the received light may propagate through the waveguide 315, bouncing between the inner surfaces of the waveguide 315 via total internal reflection (TIR), before exiting through the out-coupling diffractive grating and being projected into the user's eye through the optics 350. In examples according to this portion of the present disclosure (III. Embedded Motheye Structure), the gratings may have a periodic structural form. The gratings which may be used in various examples of this portion of the present disclosure (III. Embedded Motheye Structure) may be broadly divided into three types: surface relief gratings (SRG), which use an approximately one-dimensional (1D) periodic surface grating; volume hologram gratings (VHG), which use an approximately three-dimensional (3D) surface structure with a periodic refractive index; and polarization volume gratings (PVG), which use a dynamic internal helical structure and right-handed and left-handed circularly polarized light.

In some examples, the waveguide 315 may be comprised of two parallel transparent/semi-transparent elements between which a liquid crystal forms a thin film. In some examples, the liquid crystal may be a nematic liquid crystal, a cholesteric liquid crystal, or any liquid crystal capable of manipulation by the application of an electric field, as would be understood by one of skill in the art. In some examples, light sources/emitters may be positioned adjacent to the liquid crystal such that their light is refracted through the liquid crystal medium, to which an electric field is applied by a thin film of electrically conductive and semi-transparent material to manipulate the liquid crystal and thusly the light being projected therethrough. In other examples, at least one transparent layer in the waveguide 315 may be formed of optical polymers, plastic, glass, transparent wafers (e.g., silicon carbide (SiC) wafers), amorphous silicon, silicon oxide ($SiO_2$), silicon nitride (SiN), titanium oxide (TiO), and/or any other transparent materials used for such a purpose, as would be understood by one of ordinary skill in the art.

In some examples, the projector 330 may include any suitable light source configured to generate a coherent or partially coherent light, such as, e.g., a laser diode, a vertical cavity surface emitting laser (VCSEL), a light emitting diode (LED), or any combination thereof. In some examples, the light source may be a panel, such as a liquid crystal display (LCD) panel, a liquid-crystal-on-silicon (LCoS) display panel, an organic light-emitting diode (OLED) display panel, a micro light-emitting diode (micro-LED) display panel, a digital light processing (DLP) display panel, a laser scanning display panel, or any combination thereof. In some embodiments, the light source may include a self-emissive panel and/or an external source.

In some examples, and in particular wearable augmented reality (AR) display devices, the optics 350 may include a virtual image distance (VID) lens, or virtual image lens, which focusses a virtual image projected from the waveguide 315 onto the user's eye, thereby integrating, from the user's perspective, the projected virtual image with the actual scene of the outside environment seen through the wearable augmented reality (AR) display devices. However, in some optical lens assemblies of wearable augmented reality (AR) display devices, the virtual image distance (VID) lens, or virtual image lens, may be directly physically coupled with the waveguide 315, which poses additional process and system integration challenges, and may also result in a smaller field of view (FOV) due to the lower index contrast between the virtual image distance (VID) lens, or virtual image lens, and the substrate of the waveguide 315. Alternatively, an air gap may be employed between the waveguide 315 and the virtual image distance (VID) lens, or virtual image lens, which maintains a large field of view (FOV) of the waveguide 315, but also may cause optical issues such as stray light and ghost images due to reflections occurring at the surface of the virtual image distance (VID) lens, or virtual image lens.

In some examples, the virtual image distance (VID) lens may be formed of optical polymers, plastic, glass, transparent wafers (e.g., silicon carbide (SiC) wafers), amorphous silicon, silicon oxide ($SiO_2$), silicon nitride (SiN), titanium oxide (TiO), optical nylon, carbon-polymers, and/or any other suitably optically transparent materials used for such a purpose, as would be understood by one of ordinary skill in the art.

FIG. 23 is a simplified block diagram illustrating the internal reflections causing stray light and ghost images which may be avoided by using an embedded sub-wavelength structure, according to examples of this portion of the present disclosure (III. Embedded Motheye Structure). In FIG. 23, a diffractive grating waveguide 2315 is separated by an air gap from a virtual image distance (VID) lens 2350. However, in FIG. 23, there is no embedded sub-wavelength structure on the surface of the virtual image distance (VID) lens 2350 in accordance with this portion of the present disclosure (III. Embedded Motheye Structure).

As discussed above, the air gap may be used as the interface between the diffractive grating waveguide 2315 and the virtual image distance (VID) lens 2350 because more light is trapped within the diffractive grating waveguide 2315 based on the lower critical angle for total internal reflection (TIR), which is calculated by:

$$\theta_c = \arcsin\left(\frac{n_{air\ gap}}{n_{waveguide\ substrate}}\right)$$

where $n_{air\ gap}$ is the refractive index for the air gap and $n_{waveguide\ substrate}$ is the refractive index for the substrate of the waveguide.

As shown in FIG. 23, a beam of light 2390 projecting from the waveguide 2315 is incident upon the surface of the virtual image distance (VID) lens 2350. Part of light beam 2390 enters straight into the virtual image distance (VID) lens 2350 as 2391, but part of light beam 2390 is reflected as light beam 2393 by the surface of the virtual image distance (VID) lens 2350. This light beam 2393 further bounces within the air gap and multiplies into beams of light 2395 and 2397, which will also keep bouncing within the air gap (not shown here). Such stray light disturbs the quality of the intended image and reduces brightness overall for the user. When even a small percent of the light beam 2390 is reflected rather than refracted/transmitted through the surface of the virtual image distance (VID) lens 2350, the modulation transfer function (MTF) is detrimentally affected, and the image quality is lowered as there is a sizable decrease in contrast.

An anti-reflection coating, such as, e.g., a motheye nanostructured surface, may be employed to prevent, inter alia, the stray light and ghost images due to reflections occurring at the surface of the virtual image distance (VID) lens, or virtual image lens. Commonly, two techniques may be employed to apply anti-reflective structures/coatings, such as the motheye nanostructure, on lenses: (1) laminating a layer of film with the anti-reflective coating/structure on top of the lens surface; and (2) etching the anti-reflective coating/structure into the surface of the lens.

However, both techniques may cause problems, particularly when applying sub-wavelength structures such as the motheye structure. Over time, thermal degradation and/or delamination may occur, resulting in bubbles, warping, waviness, and other surface aberrations. When an optically clear adhesive (OCA) is used, bubbles and/or other imperfections may appear. Generally speaking, lamination makes the manufacturing process more complex, as well as the resulting optical lens assembly, by adding layer(s) to the virtual image distance (VID), or virtual image, lens. Lamination of surface coatings/structures may employ hot imprinting, which may result in waviness and other surface aberrations in the imprinted sub-wavelength structure surface on the lens. Etching surface coatings/structures, particularly sub-wavelength structures, onto lenses complicates and unnecessarily extends the manufacturing process.

According to examples of this portion of the present disclosure (III. Embedded Motheye Structure), a sub-wavelength structure, such as a motheye structure, may be embedded in the surface of a virtual image distance (VID), or virtual image, lens facing the air gap between the virtual image distance (VID), or virtual image, lens and the waveguide in an optical lens assembly of a wearable augmented reality (AR) display device. In some examples, the embedded motheye structure may eliminate the lamination process and/or the use of optically clear adhesive (OCA), thereby decreasing the possible degradation caused by warping, waviness, bubbles, thermal degradation, etc. In some examples, using an embedded motheye structure on the surface of a virtual image distance (VID), or virtual image, lens may not only reduce stray light but also allows broadband transmission therethrough.

In some examples, an embedded motheye structure may simplify both the architecture of the optical lens assembly and the process for manufacturing optical lens assemblies. In some examples, an embedded motheye structure may have hydrophobic properties. In some examples, a virtual image distance (VID), or virtual image, lens with an embedded motheye structure may be directly manufactured through cost-effective approaches like injection molding, compression molding, ultraviolet (UV) casting, and hot imprinting.

FIG. 24 is a simplified block diagram of a cross-section of an optical lens assembly employing a virtual image distance (VID) lens with an embedded motheye structure, according to an example. The optical lens assembly shown in FIG. 24 is provided to illustrate the explanation below of this example, and omits aspects, features, and/or components not germane to this example of this portion of the present disclosure (III. Embedded Motheye Structure), as would be understood by one of ordinary skill in the art. The optical lens assembly shown in FIG. 24 may be disposed in a wearable augmented reality (AR) display device, such as, e.g., the near-eye display device 300 in FIGS. 3A and 3B or the head-mounted display (HMD) device 200 of FIGS. 2A-2C.

As shown in the simplified diagram of FIG. 24, the optical lens assembly may have a frame 2405 enclosing an outer virtual image distance (VID) lens 2454, separated by an air gap from a surface relief grating (SRG) waveguide 2415, which is separated in turn on its other side by an air gap from an inner virtual image distance (VID) lens 2452, which is facing, and focused towards, an eye 2440 of the user. As used herein, the term "VID lens" may include any lens involved in the projection of light on the user's eyes in a augmented reality (AR)/virtual reality (VR) near-eye display device, and thus the outer virtual image distance (VID) lens 2454 may not be directly involved in projecting a virtual image, but is still referred to as a virtual image distance (VID) lens herein.

An embedded motheye structure 2460 may be on the surface of the inner virtual image distance (VID) lens 2452 in the air gap between the inner virtual image distance (VID) lens 2452 and the surface relief grating (SRG) waveguide 2415. A portion of the embedded motheye structure 2460 is indicated by a box 2560, which portion 2560 is shown in a planar view and two possible cross-sections in FIG. 25. As explained in further detail below in reference to FIGS. 26-28, the embedded motheye structure 2460 may be created on the surface of the inner virtual image distance (VID) lens 2452 when the inner virtual image distance (VID) lens 2452 is initially molded/manufactured by, for example, being etched into the master mold used to fabricate the inner virtual image distance (VID) lens 2452. In other examples, the motheye structure may be embedded on the surface of the outer virtual image distance (VID) lens 2454 facing the air gap and the surface relief grating (SRG) waveguide 2415. In some examples, the motheye structure may be embedded on the surfaces of both the outer virtual image distance (VID) lens 2454 and the inner virtual image distance (VID) lens 2452 facing the air gap and the surface relief grating (SRG) 2415.

FIG. 25 illustrates views of the portion 2560 of the embedded motheye structure 2460 from FIG. 24, according to examples of this portion of the present disclosure (III. Embedded Motheye Structure). In FIG. 25, planar view 2560A shows the surface texture of the embedded motheye structure 2560, while cross-sectional view 2560B shows a possible profile of embedded motheye structure 2460 with rounded peaks, but sharp troughs, and cross-sectional view 2560C shows a possible profile of embedded motheye structure 2560 with sharp peaks and troughs.

The motheye surface nanostructure is based on the unique structure of the compound eyes of moths, which have evolved to collect as much light as possible and thus to reflect as little light as possible, in order to avoid being detected by predators. Namely, the motheye nanostructure consists of a hexagonal pattern of bumps or peaks, each of which is about 200 nm high, and the centers of the bumps/peaks are separated from each other by roughly 2300 nm. Because the bumps/peaks, and the distances between them, are smaller than the wavelength of visible light (roughly 400-700 nm), light is less likely to bounce off the surface, but more likely "gets trapped" in a sense, and proceeds into and through the surface.

In examples in accordance with this portion of the present disclosure (III. Embedded Motheye Structure), the embedded motheye structure adheres to the principle behind the actual motheye structure in nature, but not necessarily to its physical parameters. In essence, any sub-wavelength nanostructure which results in the same behavior, e.g., the absorption of more incident light than the surface of the bare virtual image distance (VID) lens. Accordingly, the shapes and relative sizes of the protrusions may change according to the needs, requirements, and parameters of the specific implementation of an example of this portion of the present disclosure (III. Embedded Motheye Structure). For instance, different shapes may be used (such as, e.g., wedges), the heights and widths of the peaks/bumps/protrusions may vary, the depths and widths of the troughs/valleys may vary, etc., as would be understood by one of ordinary skill in the art.

As mentioned above, according to examples of this portion of the present disclosure (III. Embedded Motheye Structure), the embedded motheye structure 2460 may improve optical performance and simplify both the architecture of the optical lens assembly and the process for manufacturing optical lens assemblies. In some examples, the embedded motheye structure 2460 may remove one or more layers required for other coatings/structures in other optical lens assemblies, thereby simplifying the architecture and the manufacturing process. In some examples, the embedded motheye structure 2460 may eliminate the lamination process and/or optically clear adhesive (OCA), thereby decreasing the possible degradation caused by warping, waviness, bubbles, thermal degradation, etc.

In some examples, the embedded motheye structure 2460 may allow broadband transmission therethrough as well as decreasing optical degradation caused by, e.g., stray light, lamination problems including bubbles, waviness, and delamination. In some examples, the embedded motheye structure 2460 may reduce the amount of reflected and bouncing visible light to below about 0.2%. In some examples, it is possible, in theory, that the amount of reflected and bouncing visible light may be reduced to below about 0.01% if gradual index material is used.

In some examples, the embedded motheye structure 2460 may have hydrophobic properties because the motheye structure may intrinsically have a high water contact angle (WCA). Because of this high water contact angle (WCA), it is believed that the embedded motheye structure may provide inherent anti-fog, anti-condensation, and water-repellant properties for the air gap between the diffractive grating waveguide and the virtual image distance (VID) lens without the need for additional material or manufacturing steps.

As explained in detail below, according to examples of this portion of the present disclosure (III. Embedded Motheye Structure), a virtual image distance (VID) lens may be directly, more simply, and more efficiently manufactured through cost-effective approaches like, e.g., injection molding, compression molding, ultraviolet (UV) casting, and hot imprinting.

FIGS. 26, 27, and 28 are block diagrams illustrating three different manufacturing processes for the embedded motheye structure, according to examples of this portion of the present disclosure (III. Embedded Motheye Structure). The manufacturing processes, methods, and techniques shown in FIGS. 26, 27, and 28 are provided by way of example and may only be one part of the entire manufacturing process. The manufacturing processes, methods, and techniques shown in FIGS. 26, 27, and 28 may further omit parts of the manufacturing processes, methods, and techniques not germane to this portion of the present disclosure (III. Embedded Motheye Structure), as would be understood by one of ordinary skill in the art.

FIG. 26 illustrates a molding approach. First, a master mold 2610 may be fabricated with a motheye structure. The master mold 2610 may be a hard, rigid material, such as a metal, quartz, a semiconductor substrate (e.g., Si or GaAs), an oxide (e.g., $SiO_2$, $Si_3N_4$, $TiO_x$, $AlO_x$, $TaO_x$, and/or $HfO_x$), and/or the like, as would be understood by one of ordinary skill in the art. In some examples, the master mold 2610 may be a soft stamp (e.g., made of polymers), a hard-soft stamp, or any other working stamp. The motheye structure may be created in the master mold 2610 by, for example, diamond turning, etching using, e.g., ion beams and/or chemically assisted ion beams, micromachining, lithography, nanoimprint lithography (NIL), three-dimensional (3D) printing, and/or the like, as would be understood by one of ordinary skill in the art. Second, the master mold 2610 with the motheye structure may be used to fabricate a virtual image distance (VID), or virtual image, lens 2620 using a cost-effective approach such as injection molding, compression molding, ultraviolet (UV) casting, reaction injection molding, thermoforming, matrix molding, and/or hot imprinting. As would be understood by one of ordinary skill in the art, any of a large variety of master mold creation and molding techniques may be employed.

As discussed above, the molding process shown in FIG. 26 may more simply, more efficiently, and directly manufacture the virtual image distance (VID), or virtual image, lens 2620, as well as simplify the process for manufacturing optical lens assemblies. In some examples, the molding process shown in FIG. 26 may eliminate one or more layers required for other coatings/structures in other optical lens assemblies, thereby simplifying the architecture and the manufacturing process. In some examples the molding process shown in FIG. 26 may remove the lamination process and/or optically clear adhesive (OCA), thereby decreasing the possible degradation caused by warping, waviness, bubbles, thermal degradation, etc.

FIG. 27 illustrates a manufacturing approach where the motheye structure may be etched directly into a virtual image distance (VID), or virtual image, lens 2730 using plasma for surface roughening. In such an approach, a high-speed stream of particles 2735, such as electrons, ions, radicals, and/or neutral particles, in a gas mixture is shot in pulses at the target, here the virtual image distance (VID), or virtual image, lens 2730, to create the motheye structure on its surface. In some examples, the motheye structure may be optionally transferred to other surfaces by a replication technique such as, e.g., ultraviolet (UV) embossing, injection molding of polymers and sol-gel materials, and/or creating the inverse of the motheye structure pattern from the virtual image distance (VID), or virtual image, lens 2730 in a polydimethylsiloxane (PDMS) film by casting and then using the film as a stamp. As would be understood by one of ordinary skill in the art, any of a large variety of plasma etching techniques may be employed.

FIG. 28 illustrates a manufacturing process where the motheye structure may be applied in a coating directly to the surface of a virtual image distance (VID), or virtual image, lens 2840. In such an approach, a coating 2845 may consist of particles in a binder which may be applied to the surface of the virtual image distance (VID), or virtual image, lens 2840. Once the particles are bound to the surface of the virtual image distance (VID), or virtual image, lens 2840, the binder is removed by any suitable means, such as, for example, an ion beam, plasma, and/or other etching technique, a chemical-mechanical etching process, and/or any other such removal process, as would be understood by one of ordinary skill in the art, leaving behind only the motheye nanostructure on the surface of the virtual image distance (VID), or virtual image, lens 2840.

In some examples, the surface-relief structure may be fabricated by imprinting an organic or organic-inorganic matrix of an organic matrix (such as, e.g., an acrylate containing silicon and ethyl lactate solvent like UVA2) and high refractive index inorganic nanoparticles (e.g., titanium oxide ($TiO_2$)). Nanoparticles are mixed into the organic matrix at the highest possible loading or concentration that allows imprinting, and the mixture is imprinted (e.g., after cross-linking and lamination on glass). A "burn" or "etch" step is performed to remove the organic matrix or resin, using oxygen plasma ("$O_2$ ASH"). The imprinted structure (e.g., wafer) is placed into a plasma tool that generates reactive oxygen species (e.g., $O_2$ radicals) in the form of a plasma (e.g., a gas) that infiltrates the structure and etches away the organic matrix within the imprinted structure, leaving a mesh or a lattice of nanoparticles interspersed with voids. As would be understood by one of ordinary skill in the art, other direct coating and/or similar manufacturing methods may be used, such as, for example, sputtering, spray-coating, spin-coating, thermal evaporation, chemical vapor deposition (CVD), physical vapor deposition (PVD), atomic layer deposition (ALD), etc.

FIG. 29 illustrates a flow diagram for manufacturing an optical lens assembly for a wearable augmented reality (AR) display device, according to some examples. The method 2900 shown in FIG. 29 is provided by way of example and may only be one part of the entire manufacturing process. The method 2900 may further omit parts of the manufacturing process not germane to this portion of the present disclosure (III. Embedded Motheye Structure), as would be understood by one of ordinary skill in the art. Each block shown in FIG. 29 may further represent one or more steps, processes, methods, or subroutines, as would be understood by one of ordinary skill in the art. Although the method 2900 is not limited in any way to the components, apparatuses, and/or constructions shown in any of Figures described above, for the sake of convenience and ease of explanation, the blocks in FIG. 29 may refer to the components shown in FIGS. 24 and 25.

At block 2910, the surface relief grating (SRG) waveguide 2415 may be disposed within the optical lens assembly for the wearable augmented reality (AR) display device. The surface relief grating (SRG) waveguide 2415 may be used to receive augmented reality (AR) images from a projector which may be either in or optically connected to the optical lens assembly of the wearable augmented reality (AR) display device.

In block 2920, the inner virtual image distance (VID) lens 2452 may be disposed within the optical lens assembly for the wearable augmented reality (AR) display device. In some examples, the outer virtual image distance (VID) lens 2454 may be in this step, or possibly both the inner and outer virtual image distance (VID) lenses 2452 and 2454. In block 2920, the inner virtual image distance (VID) lens 2452 may be disposed such that it is separated by an air gap from the surface relief grating (SRG) waveguide 2415. In examples according to this portion of the present disclosure (III. Embedded Motheye Structure), the inner virtual image distance (VID) lens 2452 is disposed such that the embedded motheye structure 2460 on one surface of the inner virtual image distance (VID) lens 2452 faces towards the surface relief grating (SRG) waveguide 2415 through the air gap.

FIG. 30 illustrates a flow diagram for manufacturing a virtual image distance (VID) lens for an optical lens assembly in a wearable augmented reality (AR) display device, according to some examples. The method 3000 shown in FIG. 30 is provided by way of example and may only be one part of the entire manufacturing process. The method 3000 may further omit parts of the manufacturing process not germane to this portion of the present disclosure (III. Embedded Motheye Structure), as would be understood by one of ordinary skill in the art. Each block shown in FIG. 30 may further represent one or more steps, processes, methods, or subroutines, as would be understood by one of ordinary skill in the art. Although the method 3000 is not limited in any way to the components, apparatuses, and/or constructions shown in any of Figures described above, for the sake of convenience and ease of explanation, the blocks in FIG. 30 may refer to FIG. 26.

At block 3010, the master mold 2610 is fabricated with a motheye structure on an inner surface. As mentioned above, the motheye structure may be created in the master mold 2610 by, for example, diamond turning, etching using, e.g., ion beams and/or chemically assisted ion beams, micromachining, lithography, nanoimprint lithography (NIL), three-dimensional (3D) printing, and/or the like, as would be understood by one of ordinary skill in the art.

At block 3020, the virtual image distance (VID), or virtual image, lens 2620 is molded using the fabricated master mold 2610, thereby creating an embedded motheye structure on the surface of the virtual image distance (VID), or virtual image, lens 2620. As mentioned above, the virtual image distance (VID), or virtual image, lens 2620 may be molded to create the embedded motheye structure on its surface by any one or more of as injection molding, compression molding, ultraviolet (UV) casting, reaction injection molding, thermoforming, matrix molding, hot imprinting, and/or the like, as would be understood by one of ordinary skill in the art.

According to examples, an embedded motheye structure for a virtual image distance (VID), or virtual image, lens in an optical lens assembly in a wearable augmented reality (AR) display device is described herein. A method of manufacturing a virtual image distance (VID), or virtual image, lens with a motheye structure embedded therein is also described herein. A non-transitory computer-readable storage medium may have an executable stored thereon, which when executed instructs a processor to perform the methods described herein.

In the foregoing description of this portion of the present disclosure (Section III-Embedded Motheye Structure), various inventive examples are described, including devices, systems, methods, and the like. For the purposes of explanation, specific details are set forth in order to provide a thorough understanding of examples of the disclosure. However, it will be apparent that various examples may be practiced without these specific details. For example, devices, systems, structures, assemblies, methods, and other components may be shown as components in block diagram form in order not to obscure the examples in unnecessary detail. In other instances, well-known devices, processes, systems, structures, and techniques may be shown without necessary detail in order to avoid obscuring the examples.

The figures and description are not intended to be restrictive. The terms and expressions that have been employed in this disclosure are used as terms of description and not of limitation, and there is no intention in the use of such terms and expressions of excluding any equivalents of the features shown and described or portions thereof. The word "example" is used herein to mean "serving as an example, instance, or illustration." Any embodiment or design described herein as an "example" is not necessarily to be construed as preferred or advantageous over other embodiments or designs.

III.5.

In one aspect, this portion of the present disclosure (III. Motheye Embedded Structure) is directed to a wearable augmented-reality (AR) display device, comprising: a projector to project virtual images toward an eye; an optical lens assembly to receive and direct the virtual images to the eye, comprising: a waveguide to receive and direct the virtual images to the eye through a virtual image distance (VID) lens; the virtual image distance (VID) lens separated by an air gap from the waveguide, comprising an inner surface facing the waveguide; and a motheye structure embedded to the inner surface of the virtual image distance (VID) lens.

In some examples of this aspect, the motheye structure is a layer on the inner surface of the virtual image distance (VID) lens. In some examples of this aspect, the waveguide is a diffractive grating waveguide. In such examples, the diffractive grating waveguide may be at least one of a surface relief grating (SRG) waveguide, a volume hologram grating (VHG) waveguide, or a polarization volume grating (PVG) waveguide. In some examples of this aspect, the wearable augmented reality (AR) display device is a head-mounted display (HMD) device or a near-eye display device.

In some examples of this aspect, the virtual image distance (VID) lens is a first virtual image distance (VID) lens, and the air gap is a first air gap, the optical lens assembly further comprising: an outer lens to receive and direct light from an outside environment to the waveguide, being separated by a second air gap from the waveguide, comprising an inner surface facing the waveguide; and a motheye structure embedded to the inner surface of the outer lens. In some examples of this aspect, the virtual image distance (VID) lens is made of at least one of optical polymers, plastic, glass, transparent wafers (e.g., silicon carbide (SiC) wafers), amorphous silicon, silicon oxide (SiO$_2$), silicon nitride (SiN), titanium oxide (TiO), optical nylon, or carbon-polymers.

In another aspect, this portion of the present disclosure (III. Motheye Embedded Structure) is directed to a method for manufacturing an optical lens assembly of a wearable augmented-reality (AR) display device, comprising: disposing a waveguide in the optical lens assembly, the waveguide to receive virtual images from a projector and to direct the virtual images through a virtual image distance (VID) lens; and disposing the virtual image distance (VID) lens separated by an air gap from the waveguide in the optical lens assembly, the virtual image distance (VID) lens to receive and direct the virtual images, wherein the virtual image distance (VID) lens comprises an inner surface facing the waveguide, and wherein a motheye structure is embedded to the inner surface of the virtual image distance (VID) lens. In some examples of this another aspect, the motheye structure is a layer on the inner surface of the virtual image distance (VID) lens, and the waveguide is a diffractive grating waveguide.

In yet another aspect, this portion of the present disclosure (III. Motheye Embedded Structure) is directed to a method for manufacturing a virtual image distance (VID) lens, comprising: fabricating a master mold for a virtual image distance (VID) lens having a motheye structure etched in an inner surface of the master mold; and molding the virtual image distance (VID) lens using the fabricated master mold to embed the motheye structure on a surface of the virtual image distance (VID) lens.

In some examples of yet another aspect, the fabricating the master mold is performed using at least one of diamond turning, etching, micromachining, lithography, nanoimprint lithography (NIL), or three-dimensional (3D) printing. In some examples of yet another aspect, the molding is performed using at least one of injection molding, compression molding, ultraviolet (UV) casting, reaction injection molding, thermoforming, matrix molding, or hot imprinting.

IV. Collective Die-on-Wafer Processing

IV.1

This portion of the present disclosure (IV. Collective Die-on-Wafer Processing) relates generally to manufacturing the display optics of a near-eye display device, and more specifically, to improving the manufacture of waveguide dies using collective die-on-wafer processing.

IV.2

With recent advances in technology, interactive content such as virtual reality (VR) content, augmented reality (AR) content, mixed reality (MR) content, and content within and associated with a real and/or virtual environment (e.g., a "metaverse") has become more available to consumers. To facilitate delivery of this and other related content, service providers have endeavored to provide various forms of wearable display systems. One such example may be a near-eye display device, such as, e.g., a wearable headset or head-mounted display (HMD) device, a wearable eyewear, or eyeglasses (e.g., "smartglasses"). In some examples, the head-mounted display (HMD) device may project or direct light to may display virtual objects or combine images of real objects with virtual objects, as in virtual reality (VR), augmented reality (AR), or mixed reality (MR) applications. For example, in an augmented reality (AR) system, a user may view both images of virtual objects (e.g., computer-generated images (CGIs)) and the surrounding environment. Head-mounted display (HMD) devices may also present interactive content, where a user's (wearer's) gaze may be used as input for the interactive content.

Wearable display devices, such as virtual reality (VR), augmented reality (AR), and/or mixed reality (MR) glasses, may require increasingly complex and intricate lens assembly structures for display, as well as increasingly complex and intricate electronic structures for generating and providing virtual reality (VR), augmented reality (AR), and/or mixed reality (MR) content, etc., thereby complicating, inter alia, the manufacturing process. Moreover, the need for both electronics and optics to have a relatively small size and negligible weight for portability and user comfort, as well as the ability to operate in a wide variety of environments, produces a host of challenges and competing concerns, in areas such as, for example, the production/manufacturing of the display electronics/optics which provide virtual reality (VR), augmented reality (AR), and/or mixed reality (MR) content, etc., in near-eye display devices.

IV. 3

Features of this portion of the present disclosure (IV. Collective Die-on-Wafer Processing) are illustrated by way of example and not limited in the following figures, in which like numerals indicate like elements. One skilled in the art will readily recognize from the following that alternative examples of the structures and methods illustrated in the figures can be employed without departing from the principles described herein.

FIG. 1 illustrates a block diagram of an artificial reality system environment including a near-eye display device, according to an example.

FIGS. 2A through 2C illustrate various views of a near-eye display device in the form of a head-mounted display (HMD) device, according to an example.

FIGS. 3A and 3B illustrate various views of a near-eye display device in the form of a pair of glasses, according to an example.

Figure 31:
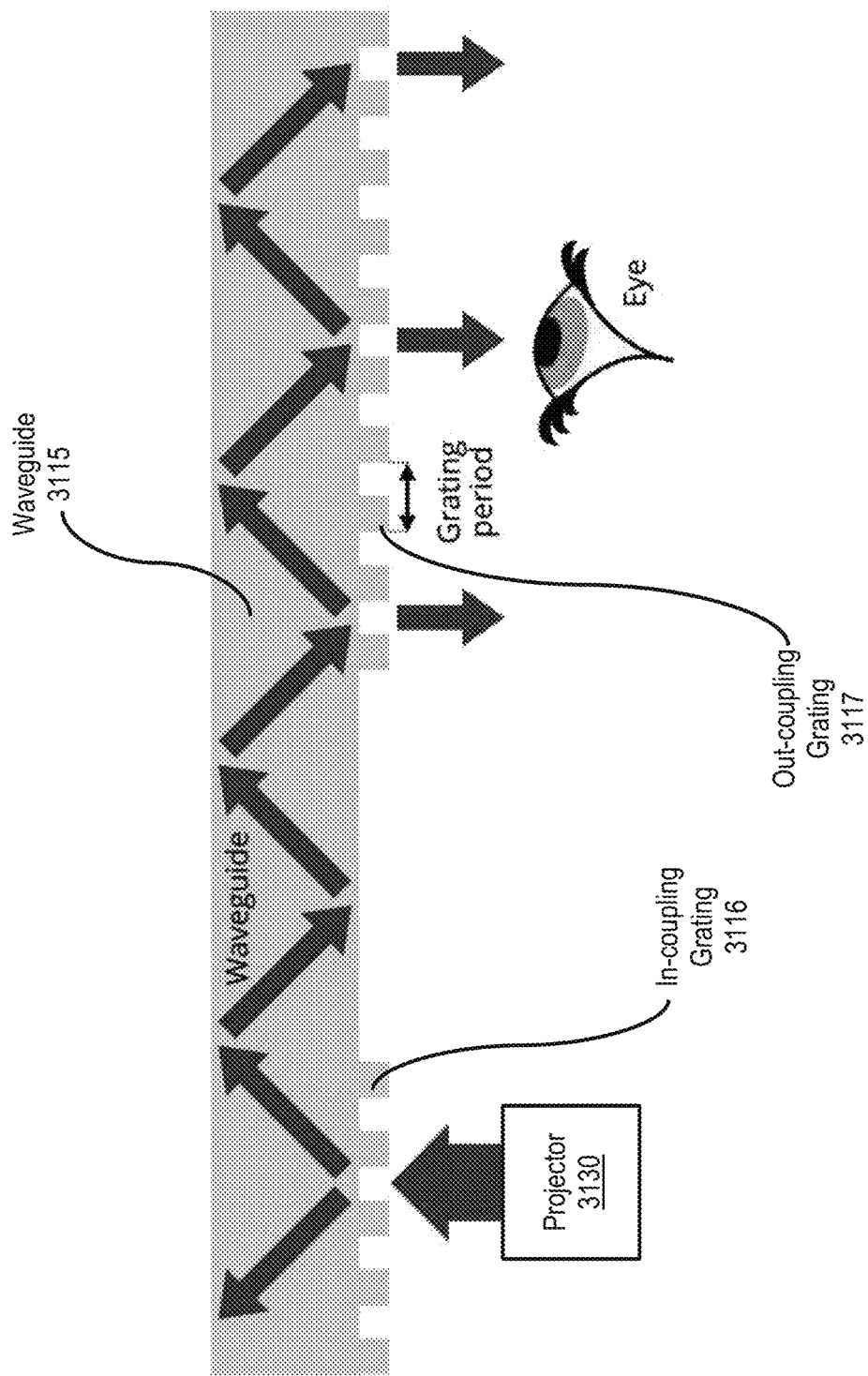

FIG. 31 illustrates a block diagram of a waveguide which may be incorporated into the display electronics/optics of a near-eye display device according to examples of this portion of the present disclosure (IV. Collective Die-on-Wafer Processing).

Figure 32:
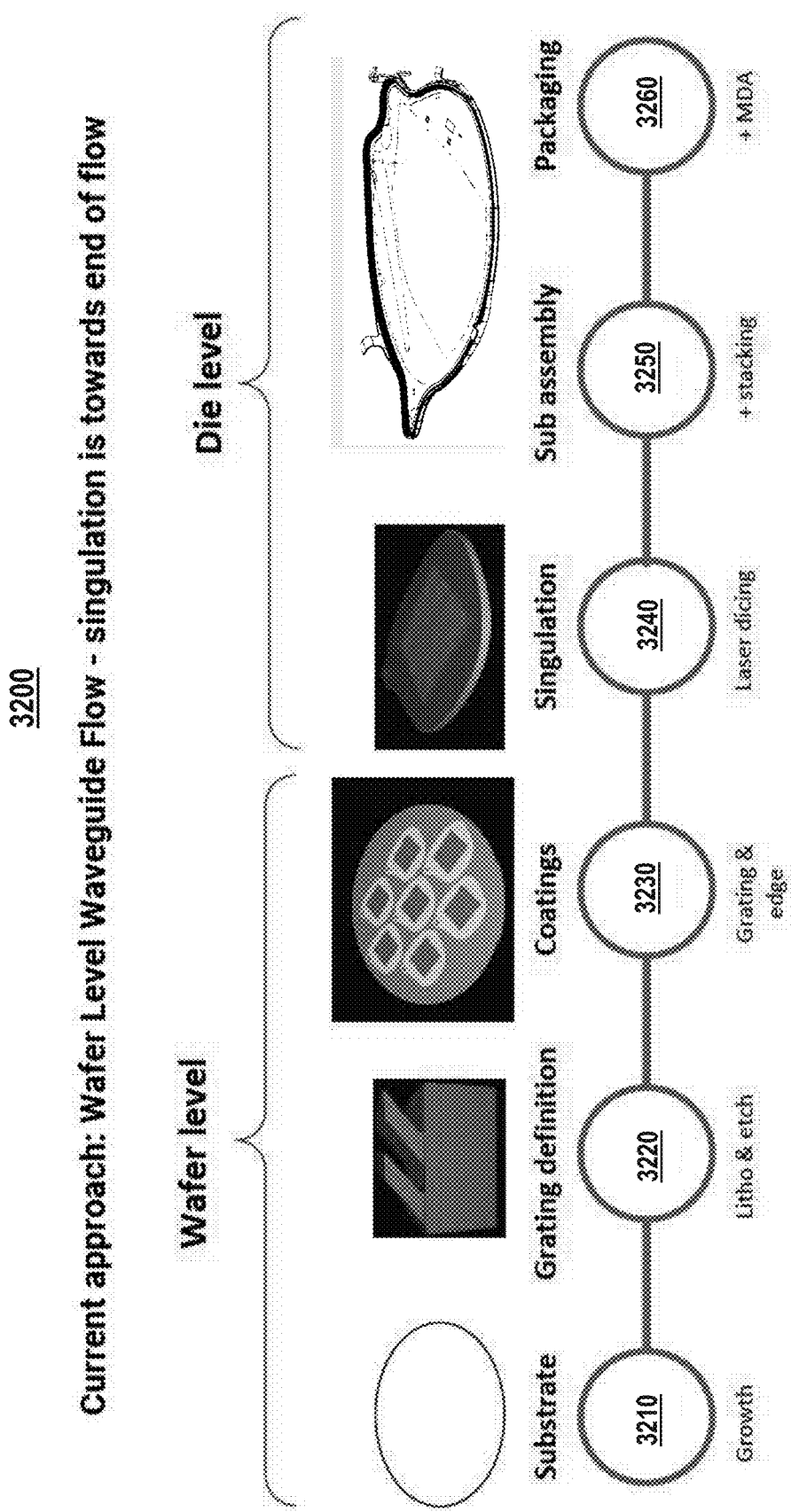

FIG. 32 illustrates a flow diagram for a method of manufacturing a waveguide which may be used as an eye lens of a near-eye display device, to which examples of this portion of the present disclosure (IV. Collective Die-on-Wafer Processing) may be applied.

Figure 33:
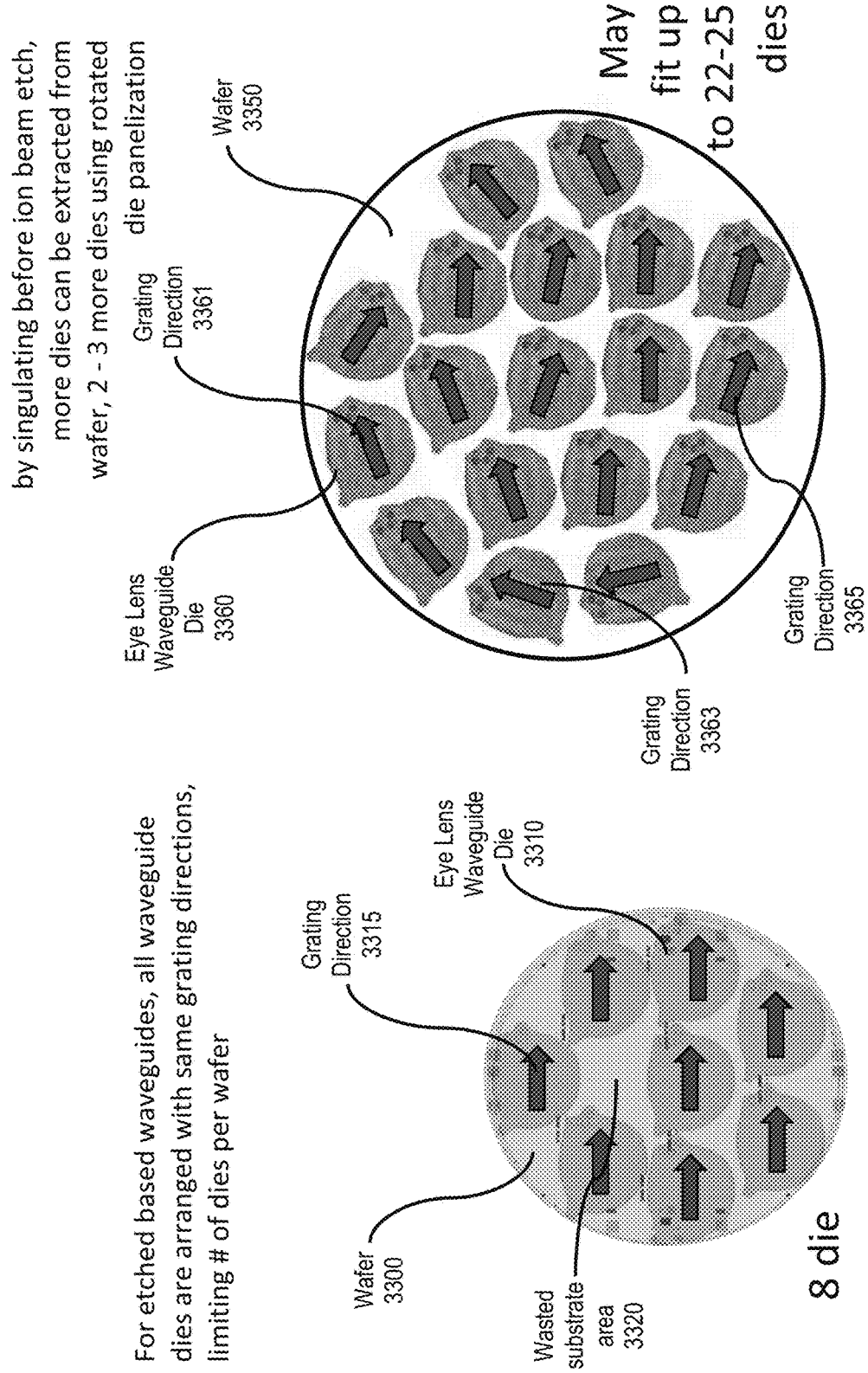

FIG. 33 is a block diagram illustrating a problem with typical etch-based waveguide manufacturing, which may be ameliorated by examples according to this portion of the present disclosure (IV. Collective Die-on-Wafer Processing).

Figure 34:
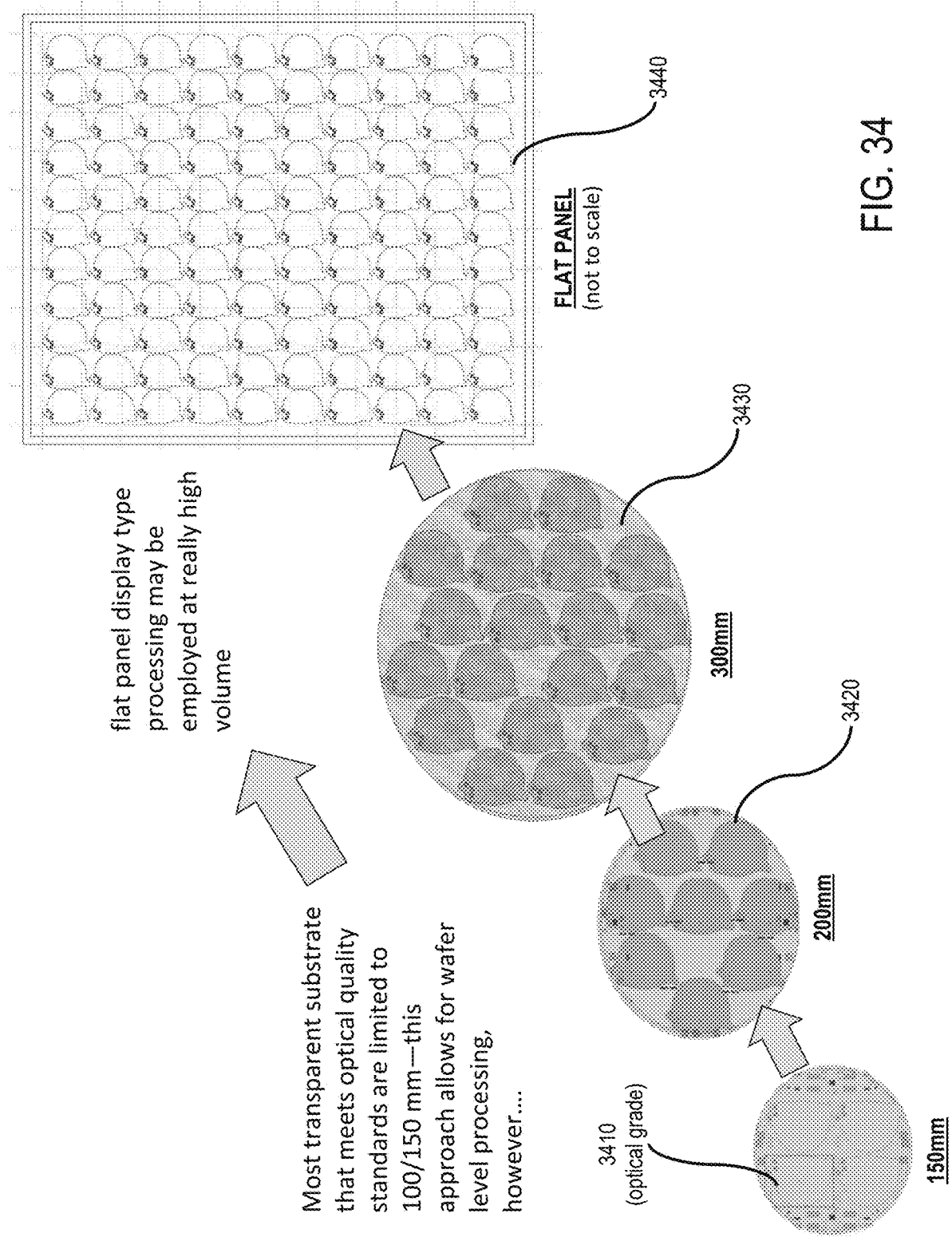

FIG. 34 is a block diagram illustrating how the relatively small size of optical grade substrate limits the waveguide manufacturing process, a problem which may be ameliorated by examples of this portion of the present disclosure (IV. Collective Die-on-Wafer Processing).

Figure 35:
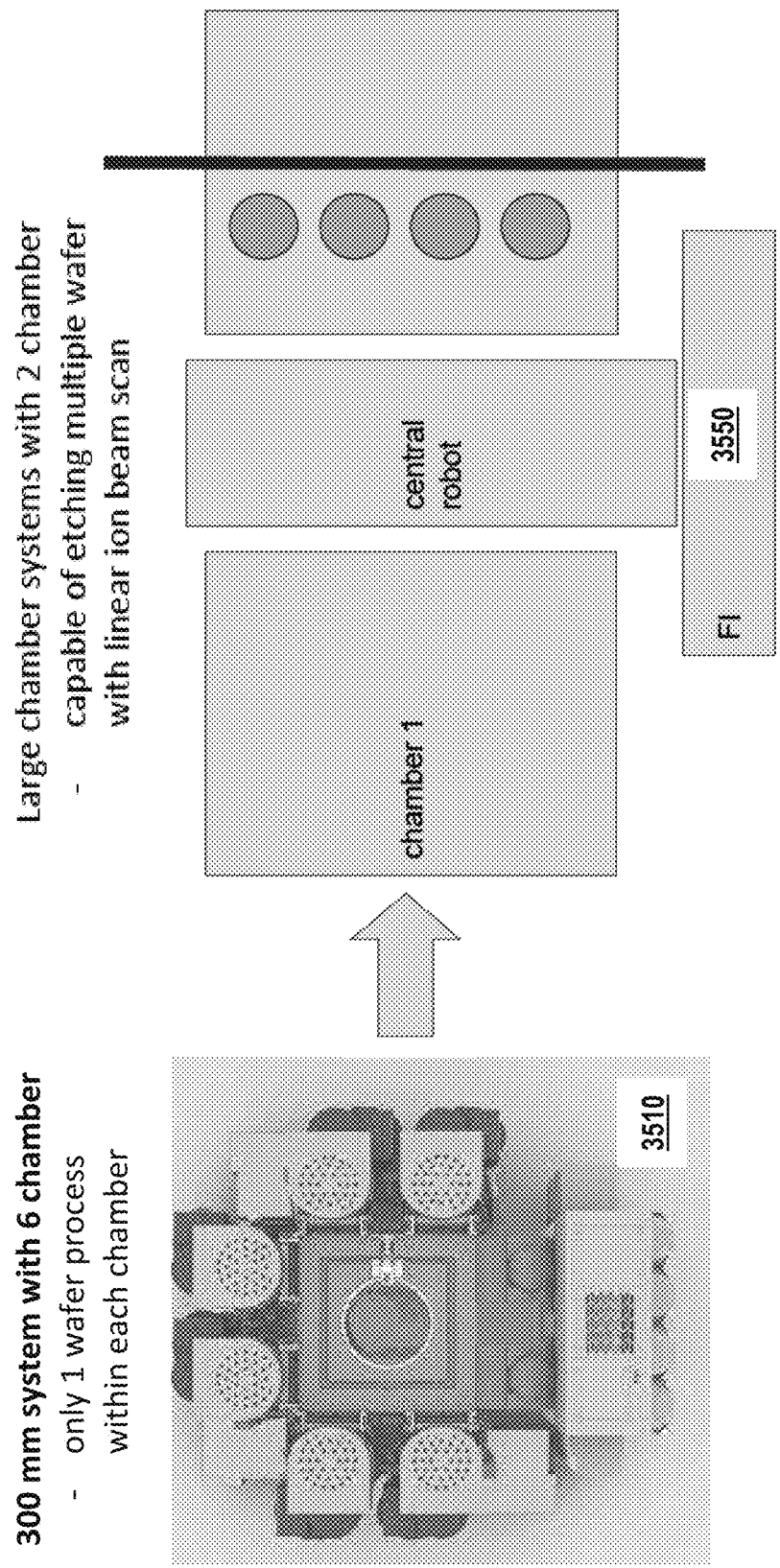

FIG. 35 is a block diagram illustrating a problem with larger size substrate etching systems, which may be ameliorated by examples according to this portion of the present disclosure (IV. Collective Die-on-Wafer Processing).

Figure 36:
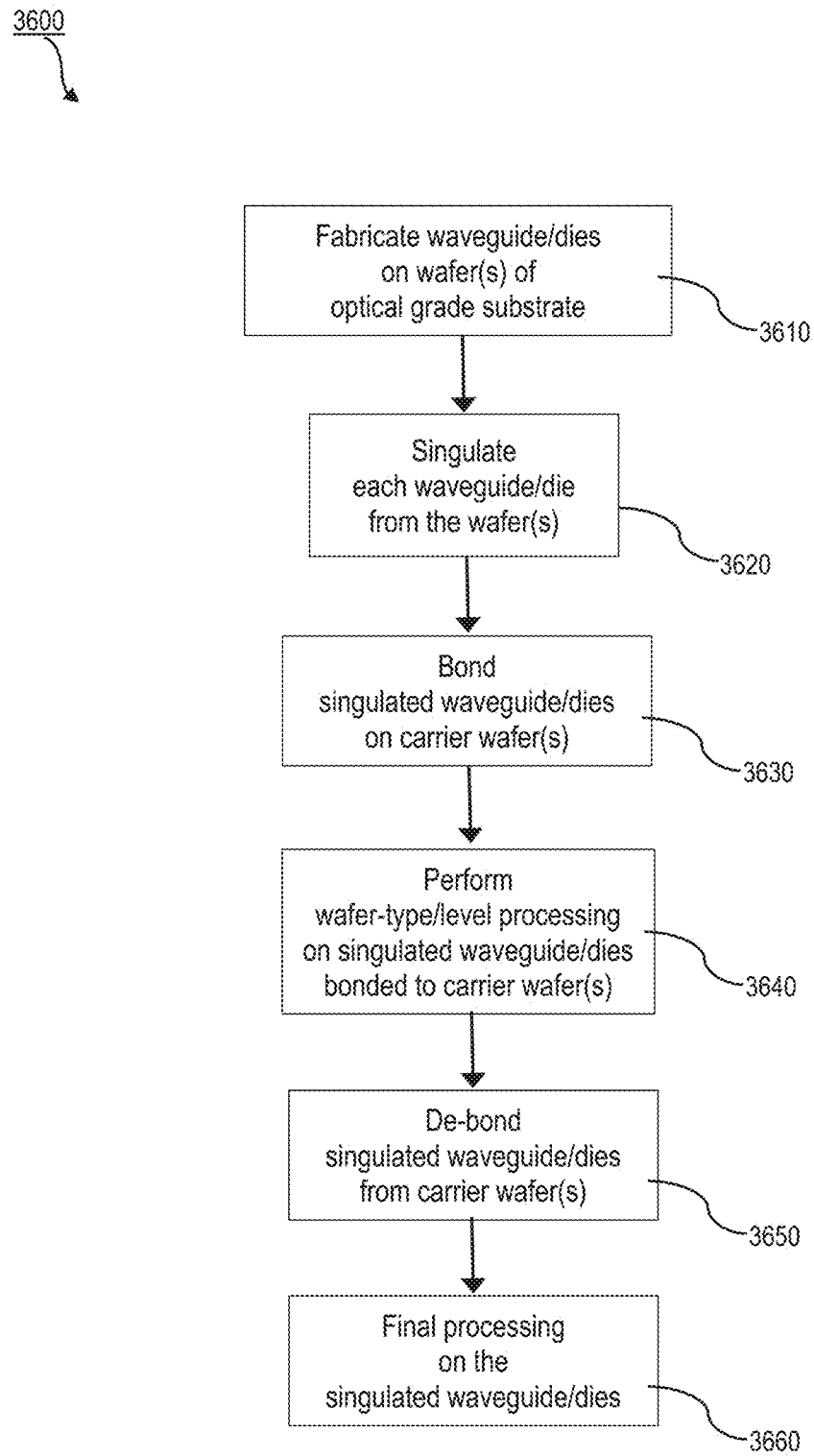

FIG. 36 illustrates a method of manufacturing a waveguide which may be used in a near-eye display device, according to an example of this portion of the present disclosure (IV. Collective Die-on-Wafer Processing).

Figure 37:

FIG. 37 illustrates a method of manufacturing a waveguide which may be used in a near-eye display device, according to an example of this portion of the present disclosure (IV. Collective Die-on-Wafer Processing).

FIG. 38 illustrates several possible flows for manufacturing a waveguide with a single-sided, one-dimensional (1D) grating which may be used in a near-eye display device, according to examples of this portion of the present disclosure (IV. Collective Die-on-Wafer Processing).

Figure 39:
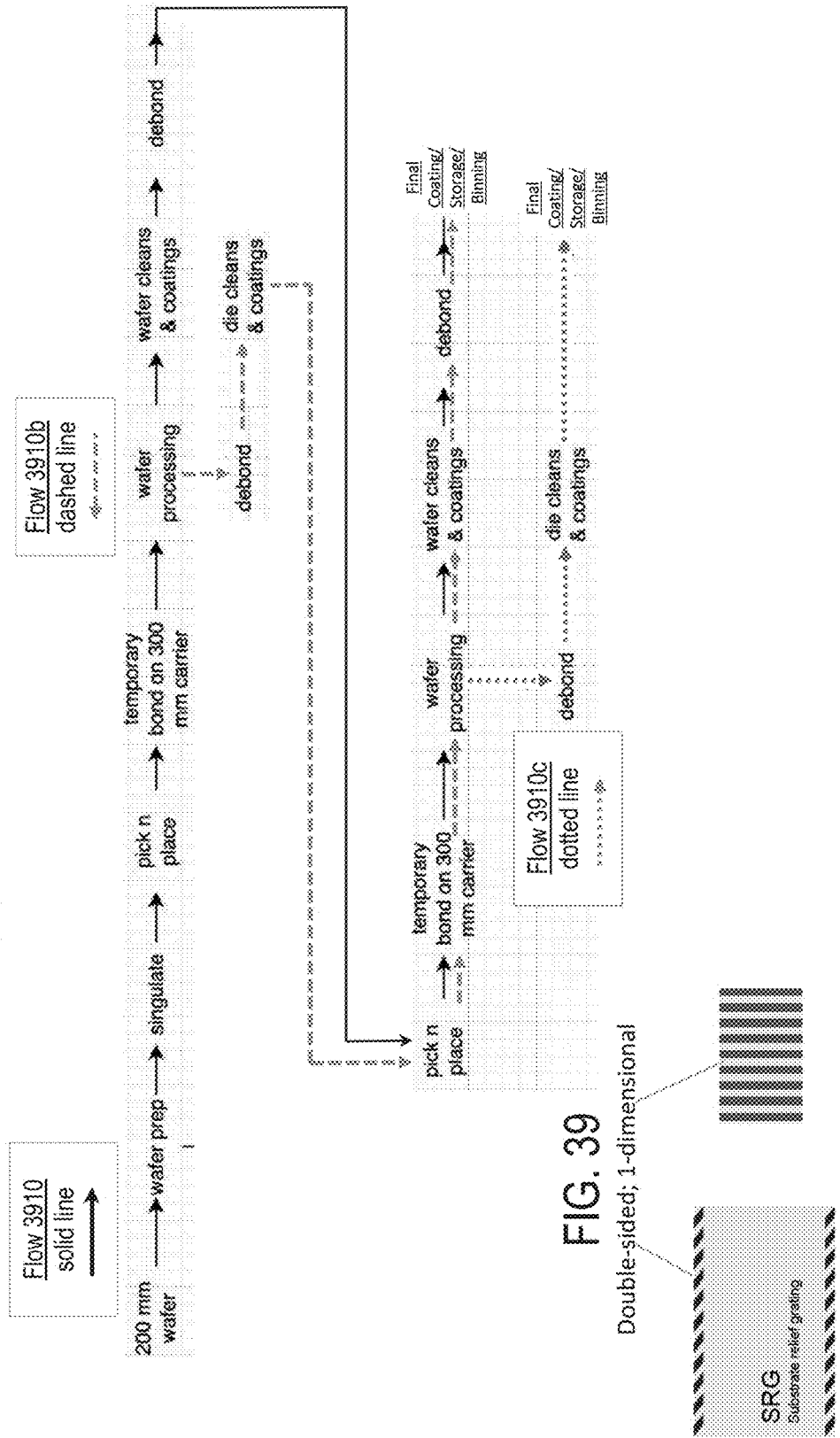

FIG. 39 illustrates several possible flows for manufacturing a waveguide with double-sided, one-dimensional (1D) gratings which may be used in a near-eye display device, according to examples of this portion of the present disclosure (IV. Collective Die-on-Wafer Processing).

Figure 40:
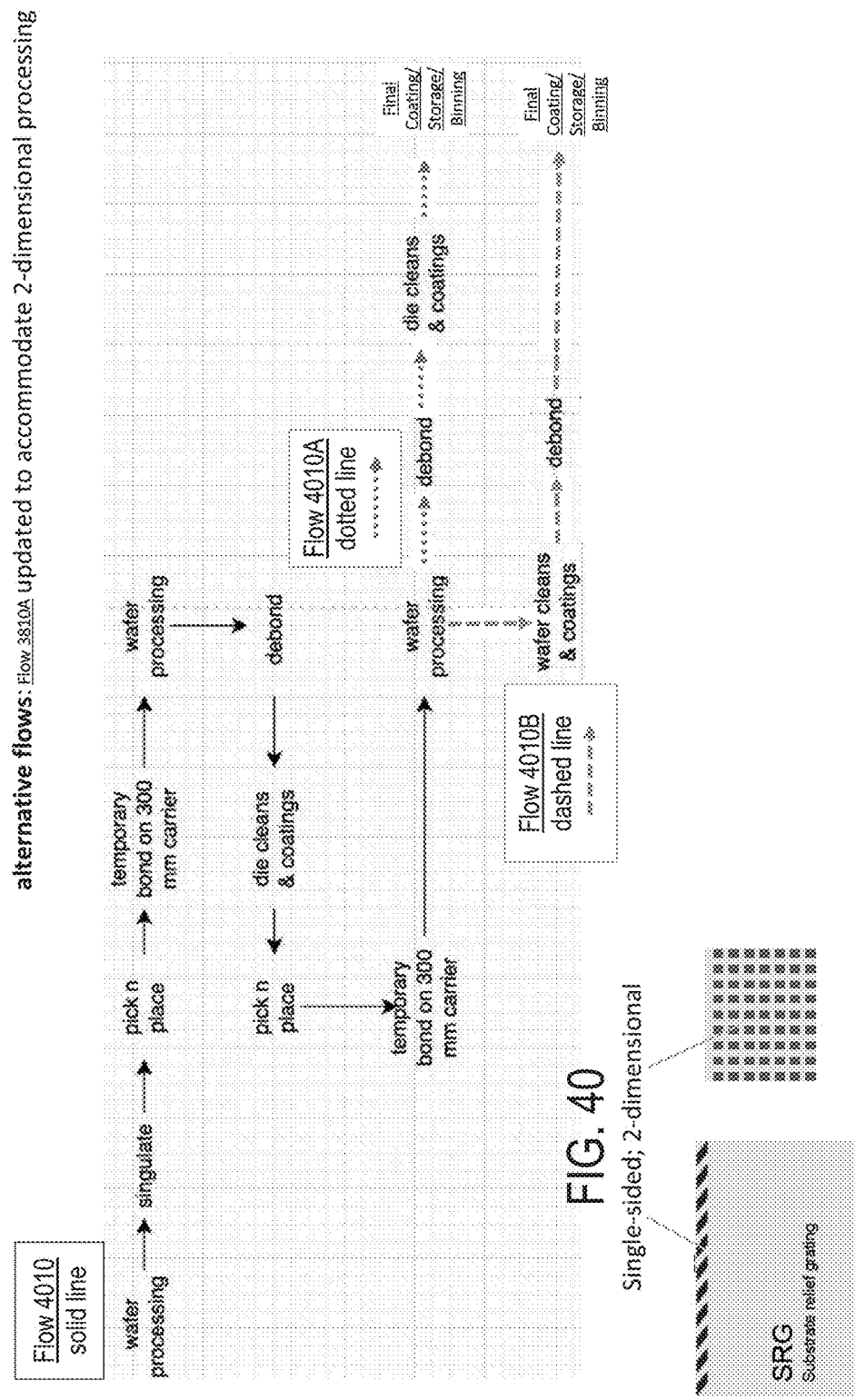

FIG. 40 illustrates several possible flows for manufacturing a waveguide with a single-sided, two-dimensional (2D) grating which may be used in a near-eye display device, according to examples of this portion of the present disclosure (IV. Collective Die-on-Wafer Processing).

IV. 4

For simplicity and illustrative purposes, this portion of the present disclosure (IV. Collective Die-on-Wafer Processing) is described by referring mainly to examples thereof. In the following description, numerous specific details are set forth in order to provide a thorough understanding of this portion of the present disclosure. It will be readily apparent, however, that this portion of the present disclosure (IV. Collective Die-on-Wafer Processing) may be practiced without limitation to these specific details. In other instances, some methods and structures readily understood by one of ordinary skill in the art have not been described in detail so as not to unnecessarily obscure this portion of the present disclosure. As used herein, the terms "a" and "an" are intended to denote at least one of a particular element, the term "includes" means includes but not limited to, the term "including" means including but not limited to, and the term "based on" means based at least in part on.

As used herein, a "near-eye display device" may refer to any display device (e.g., an optical device) that may be in close proximity to a user's eye. Accordingly, a near-eye display device may be a head-mounted display (HMD) device, such as a wearable eyewear, a wearable headset, and/or "smartglasses," which may be used for interacting with virtual reality (VR), augmented reality (AR), and/or mixed reality (MR) environments, or any environment of real and virtual elements, such as a "metaverse." As used herein, a "wearable device" may refer to any portable electronic device that may be worn on any body part of a user and used to present audio and/or video content, control other devices, monitor bodily functions, and perform similar actions. As used herein, a "user" may refer to a user or wearer of a "near-eye display device" and/or a "wearable display."

One of the challenges for the production/manufacturing of the display electronics/optics which provide virtual reality (VR), augmented reality (AR), and/or mixed reality (MR) content in near-eye display devices is the fabrication of the waveguide/display/optics by which and through which the user views the virtual reality (VR), augmented reality (AR), and/or mixed reality (MR) content. Such waveguides require optical grade substrates from which they are manufactured; however, optical grade substrates may typically only be available at smaller sizes, e.g., from about 75 mm to about 200 mm, while the greatest variety of fabrication techniques, devices, and systems may only be available at larger sizes, such as, e.g., 300 mm. This limits manufacturing flexibility, especially in terms of, e.g., scalability, as the smaller size substrates may only be capable of fitting a limited number of waveguides/dies per substrate wafer. Moreover, areas on the wafer substrate may be wasted because of how the waveguides/dies must be oriented in order for the etching/grating process to work.

According to examples of the present disclosure, methods, systems, and/or apparatuses for the manufacturing of waveguides for use in near-eye display devices are presented. In some examples, two substrate wafers are used: a first optical grade substrate wafer which may be of a smaller size (but not constrained in how the individual waveguides/dies are oriented) and then a second carrier substrate which may be of a larger size and thus more scalable as well as more compatible with a larger variety of fabrication techniques, devices, and systems, is used for further wafer processing. In some examples, the individual waveguides/dies are first fabricated with the optical grade substrate wafer, cut into individual pieces ("singulation"), and then placed and temporarily bonded to a larger size carrier substrate for further processing.

While some advantages and benefits of the present disclosure are discussed herein, there are additional benefits and advantages which would be apparent to one of ordinary skill in the art.

All of the previous paragraphs, including the descriptions of FIGS. 1, 2A-2C, and 3C, are incorporated in this portion of the present disclosure (IV. Collective Die-on-Wafer Processing) in their entirety, to be read in addition to the following further comments.

FIG. 31 illustrates a block diagram of a waveguide 3115 which may be incorporated into the display electronics/optics of a near-eye display device according to this portion of the present disclosure (IV. Collective Die-on-Wafer Processing), in a manner similar to the waveguide 215 of FIGS. 2A-2C and the waveguide 315 of FIGS. 3A-3B. As discussed above, the waveguide 3115 may be geometric, reflective, refractive, polarized, diffractive, and/or holographic, as would be understood of one of ordinary skill in the art, and may use any one or more of macro optics (such as, e.g., traditional optics, freeform prisms, and geometrical waveguide techniques), micro optics (such as, e.g., diffractive grating techniques), and/or nano optics (such as, e.g., metalenses and/or metasurfaces).

In FIG. 31, a diffractive waveguide system may include a light source, such as the projector 3130, and the waveguide 3115 which may integrate an in-coupling grating 3116 and an out-coupling grating 3117, where the in-coupling grating 3116 may receive the light projected by the projector 3130, and the received light may propagate through the waveguide 3115, bouncing between the inner surfaces of the waveguide 3115 via total internal reflection (TIR), before exiting through the out-coupling grating 3117 and being projected into the user's eye. In some examples, the in-coupling grating 3116 and the out-coupling grating 3117 may include diffractive gratings that may be any of surface relief gratings (SRG), volume hologram gratings (VHG), and/or polarization volume gratings (PVG), and may have a periodic structural form, such as, e.g., a grating period 3119 in FIG. 31.

In some examples, the waveguide 3115 may include two parallel transparent/semi-transparent elements between which a liquid crystal forms a thin film, where the liquid crystal may be a nematic liquid crystal, a cholesteric liquid crystal, or any liquid crystal capable of manipulation by the application of an electric field, as would be understood by one of skill in the art. In some examples, light sources/emitters may be positioned adjacent to the liquid crystal such that their light is refracted through the liquid crystal medium, to which an electric field is applied by a thin film of electrically conductive and semi-transparent material to manipulate the liquid crystal and thusly the light being projected therethrough. In some examples, at least one transparent layer in the waveguide 3115 may be formed of optical polymers, plastic, glass, transparent wafers (e.g., silicon carbide (SiC) wafers), amorphous silicon, silicon oxide ($SiO_2$), silicon nitride (SiN), titanium oxide (TiO), optical nylon, carbon-polymers, and/or any other suitably optically transparent materials used for such a purpose, as would be understood by one of ordinary skill in the art. In some examples, the waveguide 3115 and/or the projector 3130 may operate and/or be constructed similarly to the waveguide 315 and/or the projector 330 of FIGS. 3A-3B.

FIG. 32 illustrates a flow diagram for a method 3200 of manufacturing a waveguide which may be used as an eye lens of a near-eye display device, to which examples of this portion of the present disclosure (IV. Collective Die-on-Wafer Processing) may be applied. The method 3200 shown in FIG. 32 is provided by way of example and may only be one part of an entire process/procedure. The method 3200 may further omit parts of the method not germane to this portion of the present disclosure (IV. Collective Die-on-Wafer Processing), as would be understood by one of ordinary skill in the art. Each block shown in FIG. 3200 may further represent one or more steps, processes, methods, or subroutines, as would be understood by one of ordinary skill in the art. For the sake of convenience and ease of explanation, the blocks in FIG. 3200 may refer to the components shown in the figures described herein; however, the method 3200 is not limited in any way to the components, apparatuses, and/or constructions shown in any of figures herein.

Generally speaking, as shown in FIG. 32, the eye lens waveguide manufacturing process may be broken down into two stages: (1) a wafer stage where the wafer bearing a number of eye lens waveguides is created, lithographed, coated, and etched; and (2) a die stage, where the wafer is cut into a multitude of individual dies (in this case, individual eye lens waveguides) in a process called "singulation," and then the final eye lens waveguides is stacked and packaged. More specifically, at circle 3210 in FIG. 32, a substrate is grown for the purposes of producing a wafer out of which one or more waveguides may be manufactured. At circle 3220, lithography and etching may be used to create surface patterns and other shaping characteristics, such as, e.g., diffractive and/or other surface grating characteristics, of the one or more eye lens waveguides on the grown substrate. At circle 3230, gratings, coatings and edging are performed on the wafer, such that the shape and edges of the individual eye lens waveguides may be seen, as shown above circle 3230. At circle 3240, the second stage is started by performing singulation by, for example, laser dicing, thereby creating and individuating the one or more eye lens waveguides/dies out of the wafer. At circle 3250, the stacking of layers may be performed in a sub-assembly process and finally, at circle 3260, the assembled eye lens waveguide may be packaged, and optionally mask defect avoidance (MDA) may be performed.

However, typical grating based waveguide production such as shown in FIG. 32 may be costly, particularly because of the number of tools and process steps required during the wafer processing stage. These costs are increased because high index optical grade substrate, such as used in eye lens waveguides like, e.g., the waveguide 215 of the head-mounted device (HMD) 200 in FIGS. 2A-2C, the waveguide 315 of the near-eye display device 300 in the form of eyeglasses in FIGS. 3A-3B, and the waveguide 3115 of FIG. 31, which may be incorporated into the display electronics/optics of a near-eye display device according to this portion of the present disclosure (IV. Collective Die-on-Wafer Processing), are available at 75 mm-150 mm thicknesses, which are more expensive to manufacture, process, etc., than greater thicknesses, such as 300 mm, where economies of scale and the widespread availability of tools and processes may make manufacturing relatively inexpensive by comparison.

An appropriately high index for a substrate from which to manufacture eye lens waveguides may be in the range of 1.5 to 2.8. Useful transparent high index substrates, such as lithium niobate (LN), zinc sulfide (ZnS), titanium oxide ($TiO_2$) rutile (plate), silicon carbide (SiC), zinc selenide (ZnSe), N-BK7, N-F2, etc., may be available at 100 mm and/or 150 mm, but not at larger sizes, such as 300 mm. Accordingly, when manufacturing eye lens waveguides, one may be limited to the tools, processes, etc., which can be used at 100-150 mm thicknesses, which is problematic for a number of reasons, some of which are discussed below in reference to FIG. 34.

FIG. 33 is a block diagram illustrating a problem with typical etch-based waveguide manufacturing, which may be ameliorated by examples according to this portion of the present disclosure (IV. Collective Die-on-Wafer Processing). Specifically, FIG. 33 illustrates how typical etch-based waveguide manufacturing may lead to wasted substrate material. As shown in FIG. 33, a wafer 3300 has eight (8) dies (i.e., eye lens waveguides), including eye lens waveguide die 3310, each of which must share roughly the same grating direction (indicated by arrow(s) 3315), as this is how the etching process is performed on the wafer 3300. This may result in wasted space such as wasted substrate area 3320 on the wafer 3300.

However, if it were possible to have a multitude of grating directions on a single wafer, such as shown in wafer 3350 in FIG. 33, the substrate area may be maximized, thereby reducing wasted area, such as the wasted substrate area 3320 on the wafer 3300. More die/waveguides may be created per wafer, with much less wasted space, although this is not shown clearly by the wafer 3350, whose purpose is to demonstrate different grating directions, but does not accurately illustrate the maximization of substrate area. More specifically, the wafer 3350 may have 17 dies/waveguides, including eye lens waveguide die 3360, with many different grating directions, such as different grating directions 3361, 3363, and 3365. Accordingly, a waveguide manufacturing method which may allow for different grating/etching directions is desirable.

FIG. 34 is a block diagram illustrating how the relatively small size of optical grade substrate limits the waveguide manufacturing process, a problem which may be ameliorated by examples of this portion of the present disclosure (IV. Collective Die-on-Wafer Processing). As shown in FIG. 34, an optical grade wafer 3410 is limited in wafer size by its thickness, which is 150 mm, and may fit only 4 dies/waveguides. At thicker sizes, larger wafers are possible (as well as a much larger variety of tools, processes, and techniques, as discussed above). A 200 mm wafer 3420 may fit 8 dies/waveguides, while a 300 mm wafer 3430 may fit 19 dies/waveguides (however optical grade substrate is not available at such a size). Ultimately, the use of flat panel fabrication technology, such as shown by flat panel 3440, offers the possibility of dozens to hundreds of dies/waveguides which may be mass produced. Once again, optical grade substrate is not amenable to such technology. Accordingly, for these reasons and as discussed further above, a waveguide manufacturing method which may allow for larger substrates is desirable, although optical grade substrates are not available at such sizes.

FIG. 35 is a block diagram illustrating a problem with larger size substrate etching systems, which may be ameliorated by examples according to this portion of the present disclosure (IV. Collective Die-on-Wafer Processing). Conversely to the last figure, a disadvantage of a larger size substrate may be the capabilities of available etching machines. As shown in FIG. 35, an etching system 3510 for 300 mm substrate may only fit one wafer in each of its vacuum chambers-thus the 300 mm etching system 3510 may only etch 6 wafers at a time. It may be possible with smaller size wafers and substrates to etch much more of them at a time. For example, the etching system 3550 in FIG. 35 may include a central robot which performs the etching (which may be performed by, e.g., linear ion beam scanning) and two chambers, where each of the chambers may contain multiple individual/singulated waveguides which may be etched and/or otherwise processed at the same time. Accordingly, a waveguide manufacturing method which may allow for the simultaneous etching of a large number of smaller area substrate/waveguide structures may also be beneficial.

According to examples of this portion of the present disclosure (IV. Collective Die-on-Wafer Processing), waveguides, such as, e.g., the waveguide 215 of the head-mounted device (HMD) 200 in FIGS. 2A-2C, the waveguide 315 of the near-eye display device 300 in FIGS. 3A-3B, and the waveguide 3115 of FIG. 31, are first manufactured on a thinner high index optical grade substrate wafer, then singulated into individual dies/waveguides, which are then bonded to thicker substrate wafers in order to perform further processing on the optical grade waveguides using the benefits of thicker substrate manufacturing tools, processes, techniques, etc. In some examples, the singulated waveguide/dies may be mass processed in a manner similar to that shown with reference to system 3550 in FIG. 35. In some examples, the stage within the manufacturing process when the singulated waveguides/dies are bonded and the stage within the manufacturing process when the singulated waveguides/dies are de-bonded, may vary, as would be understood by one of ordinary skill in the art, examples of which are shown in reference to FIGS. 37-40 below. In some examples, the waveguide substrate may have grating on one side; in other examples, the waveguide substrate may have grating on both sides; in some examples, the grating on the waveguide substrate may be one-dimensional; in other examples, the grating on the waveguide substrate may be two-dimensional.

FIG. 36 illustrates a method of manufacturing a waveguide which may be used in a near-eye display device, according to an example of this portion of the present disclosure (IV. Collective Die-on-Wafer Processing). A method 3600 shown in FIG. 36 is provided by way of example and may only be one part of an entire process/procedure. The method 3600 may further omit parts of the method not germane to this portion of the present disclosure (IV. Collective Die-on-Wafer Processing), as would be understood by one of ordinary skill in the art. Each block shown in FIG. 36 may further represent one or more steps, processes, methods, or subroutines, as would be understood by one of ordinary skill in the art. For the sake of convenience and ease of explanation, the blocks in FIG. 36 may refer to the components shown in the figures described herein; however, the method 3600 is not limited in any way to the components, apparatuses, and/or constructions shown in any of figures herein.

At block 3610, wafers containing dies/waveguides may be fabricated using optical grade substrate. In some examples, such substrate may range from about 75 mm to about 200 mm, depending on whether such a size was available of an optical grade substrate (e.g., with an optical index from about 1.5 to about 2.8). In some examples, the individual dies/waveguides may be disposed in any configuration (like, e.g., the wafer 3350 in FIG. 33), as there is no need for all of the waveguide/dies to disposed in exactly the same manner (like, e.g., the wafer 3300 in FIG. 33) so that etching may be performed on all of them at once. In some examples, more waveguide/dies may be produced per wafer because of the waveguides/dies need not all have the same grating direction. In some examples, the waveguides/dies may have varying sizes.

At block 3620, the optical grade waveguide/dies may be singulated from the wafer. In some examples, edge darkening and/or metal hard mask coatings may be performed before singulation. As shown in the examples in FIGS. 37-40 below, singulation may be performed at different stages within the manufacturing process (i.e., more or less wafer processing may be performed before singulation) in accordance with this portion of the present disclosure (IV. Collective Die-on-Wafer Processing).

At block 3630, the singulated waveguide/dies may be bonded to a carrier wafer for further processing. In some examples, a temporary adhesive and/or electrostatic placement may be employed for bonding; the characteristics and qualities of a suitable bonding agent are described below in reference to Table 1. In some examples, the carrier wafer is thicker than the optical grade substrate used in block 3610, such as, for example, a 300 mm substrate. In such examples using a 300 mm carrier substrate, up to about 22-25 waveguides/dies may be bonded to a wafer. In such examples, 22 waveguides/dies may be bonded per wafer without compromising the 3 mm edge exclusion using pick-and-place/surface mount technology (e.g., pick-and-place machines, planar mounting, surface mount devices (SMDs)), temporary adhesives, electrostatic placement, etc., as would be understood by one of ordinary skill in the art. In some examples, it is contemplated that a flat panel display technology may be employed as the carrier in block 3630. In some examples, it is contemplated that more processing may be performed on the individual waveguides/dies en masse before the bonding in block 3630.

At block 3640, wafer-type/level processing may be performed on the singulated waveguides/dies bonded to the carrier wafer. In some examples, the gratings may be formed in block 3640 by, for example, nanoimprinting, etching, and/or a combination of the two. In some examples, 300 mm front end of the line (FEOL) processing may be employed on the singulated waveguides/dies bonded to the carrier wafer in block 3640. In some examples, the singulated waveguides/dies bonded to the carrier wafer may be nanoimprinted, binary mask chrome etched, greytoned (by inkjet and/or spin), and ion-beam etched to realize slant structures within the surface grating. In some examples, other techniques and/or processes may be employed to create surface features on the singulated waveguides/dies bonded to the carrier wafer, as would be understood by one of ordinary skill in the art.

At 3650, the singulated waveguides/dies may be de-bonded from the carrier wafer. In some examples, the waveguides/dies may be detached via thermal, mechanical, and/or laser de-boding from the carrier wafer.

At block 3660, final processing may be performed on the individual waveguides/dies. In some examples, final processing may include cleaning, surface activation, coatings, preparation for storage, storage/binning, and/or entering into the manufacturing process of the near-eye display device. In some examples, the coatings may be dual-sided atomic layer deposition (ALD) coatings. In some examples, a third carrier for the waveguides/dies may be employed, a die-level carrier useful for performing surface activation, coatings, etc., as would be understood by one of ordinary skill in the art.

As mentioned above, and made more clear by the examples in FIGS. 37-40 below, what happens between block 3610 and 3620, what happens during the wafer-type/level processing in block 3640, and what happens during the final processing of block 3660 may vary greatly from implementation to implementation of examples of this portion of the present disclosure (IV. Collective Die-on-Wafer Processing). For instance, a process performed in block 3640 in one implementation may be performed in block 3660 of another implementation, just as a process performed before singulation in block 3620 in one implementation may be performed after singulation in another implementation or even in block 3640, as would be understood by one of ordinary skill in the art and as made clear by the examples in FIGS. 37-40 below.

FIG. 37 illustrates a method of manufacturing a waveguide which may be used in a near-eye display device, according to an example of this portion of the present disclosure (IV. Collective Die-on-Wafer Processing). A method 3700 shown in FIG. 37 is provided by way of example and may only be one part of an entire process/procedure. The method 3700 may further omit parts of the method not germane to this portion of the present disclosure (IV. Collective Die-on-Wafer Processing), as would be understood by one of ordinary skill in the art. Each block shown in FIG. 37 may further represent one or more steps, processes, methods, or subroutines, as would be understood by one of ordinary skill in the art. For the sake of convenience and ease of explanation, the blocks in FIG. 37 may refer to the components shown in the figures described herein; however, the method 3700 is not limited in any way to the components, apparatuses, and/or constructions shown in any of figures herein.

As shown in FIG. 37, the 3700 may have four parts or stages (labelled Parts 1-4), within which multiple processes/actions may be performed, each of which is balled with its own box and corresponding graphic (except "Storage/Binning"). The parts in FIG. 37 do not correspond directly to the blocks in FIG. 36, as already discussed above, as details may vary according to implementations of this portion of the present disclosure (IV. Collective Die-on-Wafer Processing). In FIG. 37, Part 1 (3710) includes die preparation of silicon carbide (SiC) enabling maximum panelization; Part 2 (3720) includes carrier population, and die-2-wafer collective temporary binding; Part 3 (3730) includes wafer level grating formation (which, in this example, is two-dimensional (2D) grating); and Part 4 (2740) includes carrier separation, de-bonding, and optical coatings.

In FIG. 37, Part 1 (3710) may include an initial quality control (IQC) of the optical waveguide substrate for defects, etc.; edge darkening (featuring (1) ion implantation and/or (2) metal deposition); metal hardmask (which may be physical vapor deposition (PVD) chromium deposition); singulation, and then storage binning of the singulated waveguides/dies, as would be understood by one of ordinary skill in the art. Part 2 (3720) may include an initial quality check of the carrier substrate for defects, etc.; the application of a temporary adhesive by spin and/or inkjet; pick-and-placement of the waveguides/dies on the carrier wafer; and then the inter-die fill by droplet and/or inkjet, as would be understood by one of ordinary skill in the art.

In FIG. 37, Part 3 (3730) may include a nanoimprint (frontside); plasma etching by chrome mask; greytoning by inkjet and/or spin; slant etching by ion-beam; and then cleaning by plasma and cryo, or possibly wets, as would be understood by one of ordinary skill in the art. Part 4 (3740) may include de-bonding; pick-and-placement of the de-bonded waveguides/dies on a die level carrier; surface activation (by, e.g., wets); coatings (e.g., ALD and/or inkjet); and then storage/binning, as would be understood by one of ordinary skill in the art.

FIG. 38 illustrates several possible flows for manufacturing a waveguide with a single-sided, one-dimensional (1D) grating which may be used in a near-eye display device, according to examples of this portion of the present disclosure (IV. Collective Die-on-Wafer Processing). The flows shown in FIG. 38 are provided by way of example and may only be one part of an entire/larger process/procedure; each flow may further omit parts of the manufacturing process not germane to explaining the flows in this portion of the present disclosure (IV. Collective Die-on-Wafer Processing), as would be understood by one of ordinary skill in the art. FIG. 38 may refer to processes, procedures, and/or techniques which may, in turn, further represent one or more steps, processes, methods, or subroutines, as would be understood by one of ordinary skill in the art.

In FIG. 38, a single flow starts on the right-hand side and then separate flows branch off to indicate different sequences which may be performed, and when a flow branches off, it has a new type of arrow to differentiate it from the other flows. More specifically, a flow 3810A starts with a 200 mm wafer and then, as indicated by the solid arrows, proceeds to wafer prep, singulation, pick-and-placement, bonding, wafer processing, wafer cleaning & coating, de-bonding, and then the final stage, whether it be coating, storage, binning, or the like, as would be understood by one of ordinary skill in the art. A flow 3820A breaks off from the flow 3810A after the wafer prep and then, as indicated by the dotted lined arrows, performs wafer processing before singulation (by contrast to the flow 3810A), pick-and-placement, bonding, wafer processing, wafer cleaning & coating, de-bonding, and then the final stage, whether it be coating, storage, binning, or the like, as would be understood by one of ordinary skill in the art.

In FIG. 38, another flow 3810*b* breaks off from the flow 3810A after wafer processing, as indicated by the dashed line, proceeds to de-bonding, die cleaning & coating (dies instead of wafers because the dies have been removed from the carrier wafer), and then the final stage, whether it be coating, storage, binning, or the like, as would be understood by one of ordinary skill in the art. Yet another flow 3820*b* breaks off from the flow 3820A after wafer processing, as indicated by the dash-dot line, proceeds to de-bonding, die cleaning & coating (dies instead of wafers because the dies have been removed from the carrier wafer), and then the final stage, whether it be coating, storage, binning, or the like, as would be understood by one of ordinary skill in the art. As indicated on FIG. 38, alternative flows may be performed where the bonding stage occurs at other points in the flows.

FIG. 39 illustrates several possible flows for manufacturing a waveguide with double-sided, one-dimensional (1D)

grating which may be used in a near-eye display device, according to examples of this portion of the present disclosure (IV. Collective Die-on-Wafer Processing). The flows shown in FIG. 39 are provided by way of example and may only be one part of an entire/larger process/procedure; each flow may further omit parts of the manufacturing process not germane to explaining the flows in this portion of the present disclosure (IV. Collective Die-on-Wafer Processing), as would be understood by one of ordinary skill in the art. FIG. 39 may refer to processes, procedures, and/or techniques which may, in turn, further represent one or more steps, processes, methods, or subroutines, as would be understood by one of ordinary skill in the art. As indicated on FIG. 39, FIG. 39 shows alternative flows to the flow 3810A in FIG. 38 accommodated to manufacture waveguides with double-sided gratings.

In FIG. 39, a single flow starts on the right-hand side and then separate flows branch off to indicate different sequences which may be performed, and when a flow branches off, it has a new type of arrow to differentiate it from the other flows. More specifically, a flow 3910 starts with a 200 mm wafer and then, as indicated by the solid arrows, proceeds to wafer prep, singulation, pick-and-placement on a first side, bonding onto the first side, wafer processing while bonded to the first side, wafer cleaning & coating while bonded to the first side, de-bonding from the first side, and then pick-and-placement on a second side, bonding onto the second side, wafer processing while bonded to the second side, wafer cleaning & coating while bonded to the second side, de-bonding from the second side, and then the final stage, whether it be coating, storage, binning, or the like, as would be understood by one of ordinary skill in the art. A flow 3910b breaks off from the flow 3910 after the wafer processing while bonded to the first side and then, as indicated by the dashed lined arrows, performs de-bonding from the first side before die cleaning and coatings (dies instead of wafers because the dies have been removed from the carrier wafer, by contrast to the flow 3910 where cleaning and coatings are performed while still attached to the carrier wafer), and then pick-and-placement on a second side, bonding onto the second side, wafer processing while bonded to the second side, wafer cleaning & coating while bonded to the second side, de-bonding from the second side, and then the final stage, whether it be coating, storage, binning, or the like, as would be understood by one of ordinary skill in the art. Another flow 3910c breaks off from the flow 3910 and the flow 3910b after wafer processing while bonded to the second side, as indicated by the dotted line, proceeds to de-bonding from the second side, die cleaning & coating (dies instead of wafers because the dies have been removed from the carrier wafer, by contrast to the flows 3910 and 3910b where cleaning and coatings are performed while still attached to the carrier wafer), and then the final stage, whether it be coating, storage, binning, or the like, as would be understood by one of ordinary skill in the art.

FIG. 40 illustrates several possible flows for manufacturing a waveguide with a single-sided, two-dimensional (2D) grating which may be used in a near-eye display device, according to examples of this portion of the present disclosure (IV. Collective Die-on-Wafer Processing). The flows shown in FIG. 40 are provided by way of example and may only be one part of an entire/larger process/procedure; each flow may further omit parts of the manufacturing process not germane to explaining the flows in this portion of the present disclosure (IV. Collective Die-on-Wafer Processing), as would be understood by one of ordinary skill in the art. FIG. 40 may refer to processes, procedures, and/or techniques which may, in turn, further represent one or more steps, processes, methods, or subroutines, as would be understood by one of ordinary skill in the art. As indicated on FIG. 40, FIG. 40 shows alternative flows to the flow 3810A in FIG. 38 accommodated to manufacture waveguides with two-dimensional (2D) gratings.

In FIG. 40, a flow 4010 starts with wafer processing and then, as indicated by the solid arrows, proceeds to singulation, pick-and-placement, bonding, wafer processing, and then de-bonding. At this point, a one-dimensional grating has been made, so the waveguide/die needs to be removed from the carrier wafer, re-oriented by 90 degrees, and then re-bonded to the carrier substrate. This is to create a two-dimensional "grid" grating pattern (such as shown in FIG. 40) by performing the same grating/etching operation while the waveguide/die is in a different orientation (namely, turned 90 degrees from the first bonded position on the carrier wafer). After the (first) de-bonding, there are die cleanings and coatings before the (second) pick-and-placement for the bonding in the new orientation on the carrier wafer. With the subsequent (second) wafer processing, the second etching/grating is performed, perpendicular to the first, thereby creating the two-dimensional (2D) "grid" grating pattern.

At this point, after the two-dimensional (2D) grating is complete, the flow 4010 may branch in one of two ways: a flow 4010A, indicated by a dotted line, where the waveguide/dies are yet again de-bonded, cleaned and coated, and then the final stage, whether it be coating, storage, binning, or the like, as would be understood by one of ordinary skill in the art; or a flow 4010B, indicated by a dashed line, where the waveguide/dies, still bonded thereto the carrier wafer, are first cleaned and coated, and then de-bonded, before the final stage, whether it be coating, storage, binning, or the like, as would be understood by one of ordinary skill in the art.

As mentioned above, each of the flows in each of FIGS. 38, 39, and 40 show possible flows under the particular constraints in each instance (e.g., a die/waveguide with a one-dimensional (1D) grating on a single side in FIG. 38; a die/waveguide with a one-dimensional (1D) grating on both sides in FIG. 39; and a die/waveguide with a two-dimensional (2D) grating on a single side in FIG. 40), but examples of this portion of the present disclosure (IV. Collective Die-on-Wafer Processing) are not limited to the steps, stages, flows, orders, sequences, etc., shown in any of FIGS. 38, 39, and 40, as would be understood by one of ordinary skill in the art.

As mentioned above, the bonding agent which may be employed to temporarily attach the waveguide/dies to the carrier wafer may need to meet certain requirements and deal with specific challenges, as listed in Table 1 below.

TABLE 1

Bonding Agent Requirements & Challenges

| Requirements | Challenges |
|---|---|
| ≤400° C. Temperature Stability | Stress induced by: |
| Superior Adhesion | Extensive Thermal Cycling |
| Compatibility with Water & Panel Processing | Coefficient of Thermal Expansion (CTE) |
| Enable Substrate Thinning ≤ 50 um | Mechanical Grinding Metal Deposition |
| Chemical resistance | Procedures |
| Excellent TTV | Chemical Resistance to: |

TABLE 1-continued

Bonding Agent Requirements & Challenges

| Requirements | Challenges |
| --- | --- |
| Compatibility with Downstream Processes (No Material Movement) High Throughput, Easy Processing Low Cost | Photolithographic Solutions Metal Etch Chemistries General Cleaning Solvents Chemical Compatibility with: Metals, EMCs, Polyamides . . . |

According to examples, methods of manufacturing a waveguide for a near-eye display device are described herein. According to examples, systems and apparatuses for manufacturing a waveguide for a near-eye display device are also described herein. A non-transitory computer-readable storage medium may have an executable stored thereon, which when executed instructs a processor to perform the methods described herein.

In the foregoing description, various inventive examples are described, including devices, systems, methods, and the like. For the purposes of explanation, specific details are set forth in order to provide a thorough understanding of examples of the disclosure. However, it will be apparent that various examples may be practiced without these specific details. For example, devices, systems, structures, assemblies, methods, and other components may be shown as components in block diagram form in order not to obscure the examples in unnecessary detail. In other instances, well-known devices, processes, systems, structures, and techniques may be shown without necessary detail in order to avoid obscuring the examples.

The figures and description are not intended to be restrictive. The terms and expressions that have been employed in this disclosure are used as terms of description and not of limitation, and there is no intention in the use of such terms and expressions of excluding any equivalents of the features shown and described or portions thereof. The word "example" is used herein to mean "serving as an example, instance, or illustration." Any embodiment or design described herein as an "example" is not necessarily to be construed as preferred or advantageous over other embodiments or designs.

IV.5

In one aspect, this portion of the present disclosure (IV. Collective Die-on-Wafer Processing) is directed to a method of manufacturing waveguides by fabricating one or more waveguides in a first wafer of a first substrate, the first substrate being of optical grade; singulating the one or more waveguides from the first wafer; bonding the one or more waveguides to a second wafer of a second substrate different from the first substrate; and forming surface gratings in the one or more waveguides bonded to the second wafer. In some examples, the first substrate has a high index, such as, e.g., about 1.5 to about 2.8. In some examples, the first substrate may include lithium niobate (LN), zinc sulfide (ZnS), titanium oxide ($TiO_2$) rutile (plate), silicon carbide (SiC), zinc selenide (ZnSe), N-BK7, and/or N-F2. In some examples, the first substrate may be between about 75 mm to about 2000 mm in size.

In some examples, the second substrate is thicker than the first. In some examples, the thickness of the second substrate is about 300 mm or greater. In some examples, the second substrate is not optical grade. In some examples, the bonding is made with a temporary adhesive.

In some examples, the method of manufacturing further includes de-bonding the one or more waveguides from the second wafer. In some examples, the method of manufacturing further includes at least one of surface activation, cleaning, coating, cleaning, etching, nanoimprinting, and/or the like, as described above.

The invention claimed is:

1. A near-eye display device, comprising:
   a frame;
   a projector disposed in the frame to project light onto an eye;
   a photodetector disposed in the frame to receive a reflection from a tear film of the eye of the light projected onto the eye by the projector;
   a processor and a non-transitory computer-readable storage medium having an executable stored thereon, which when executed instructs the processor to perform one or more reflectometric measurements of ocular hydration of the eye using the received reflection as input from the photodetector; and
   an eye tracking system to re-calibrate eye tracking parameters based on the one or more reflectometric measurements,
   wherein the eye tracking parameters comprise at least one of an intensity of an eye tracking illumination source or an exposure time of an eye tracking photosensor.

2. The near-eye display device of claim 1, wherein the eye tracking system comprises the projector.

3. The near-eye display device of claim 1, wherein the eye tracking system comprises the photodetector.

4. The near-eye display device of claim 1, wherein the eye tracking system comprises the processor.

5. The near-eye display device of claim 1, wherein the photodetector comprises a polarization sensitive photodetector to de-couple specular reflections from the tear film of the eye and diffuse reflections from a sub-surface of the eye to separate out measurements of the tear film and measurements of the sub-surface of the eye.

6. The near-eye display device of claim 1, wherein the projector comprises a projector to project at least one of an augmented reality (AR) or a virtual reality (VR) image.

7. The near-eye display device of claim 1, wherein the projector comprises a laser scanning source to project images on a retina of the eye.

8. The near-eye display device of claim 1, wherein the projector is integrated into at least one of an augmented reality (AR) image display projector or a virtual reality (VR) image display projector.

9. The near-eye display device of claim 1, wherein the projector comprises one or more diffuse light sources.

10. The near-eye display device of claim 1, wherein the projector is further to project at least one of polarized light or unpolarized light onto the eye.

11. A method for a near-eye display device, comprising:
    receiving light reflected from a tear film of an eye;
    measuring ocular hydration using the received light reflected from the tear film; and
    re-calibrating eye tracking parameters of an eye tracking system of the near-eye display device based on the measuring,
    wherein the eye tracking parameters comprise at least one of an intensity of an eye tracking illumination source or an exposure time of an eye tracking photosensor.

12. The method of claim 11, further comprising:
    projecting light to be reflected from the tear film of the eye.

13. The method of claim 11, wherein the measuring ocular hydration comprises:
measuring glints from the tear film of the eye.

14. The method of claim 11, wherein the receiving light reflected from the tear film of the eye comprises:
de-coupling specular reflections from the tear film of the eye and diffuse reflections from a sub-surface of the eye to separate out measurements of the tear film and measurements of the sub-surface of the eye.

15. The method of claim 14, further comprising:
projecting at least one of polarized light or unpolarized light to be reflected from the tear film of the eye,
wherein the de-coupling specular reflections from the tear film of the eye and diffuse reflections from a sub-surface of the eye is based on a polarization state of the specular reflections and the diffuse reflections.

16. The method of claim 11, further comprising:
determining, using the measuring, whether to prompt a user to take remedial action concerning the eye.

17. A method for a near-eye display device, comprising:
receiving light reflected from a tear film of an eye;
determining whether the eye is open and stationary for a sufficient length of time for measuring ocular hydration using the received reflected light;
measuring ocular hydration using the received light reflected from the tear film; and
re-calibrating eye tracking parameters of an eye tracking system of the near-eye display device based on the measuring.

18. The method of claim 17, further comprising:
determining, using the measuring, whether to prompt a user to take remedial action concerning hydration of the eye.

19. The method of claim 18, wherein the determining comprises:
determining, using the measuring and input from one or more sensors on the near-eye display device, whether to prompt the user to take remedial action concerning hydration of the eye.

20. The method of claim 17, further comprising:
projecting at least one of polarized light or unpolarized light to be reflected from the tear film of the eye,
wherein the receiving light reflected from the tear film of the eye comprises de-coupling specular reflections from the tear film of the eye and diffuse reflections from a sub-surface of the eye to separate out measurements of the tear film and measurements of the sub-surface of the eye, and
wherein the de-coupling specular reflections from the tear film of the eye and diffuse reflections from the sub-surface of the eye is based on a polarization state of the specular reflections and the diffuse reflections.

* * * * *